(12) United States Patent
Sibbesen et al.

(10) Patent No.: US 9,249,403 B2
(45) Date of Patent: Feb. 2, 2016

(54) POLYPEPTIDES WITH XYLANASE ACTIVITY

(71) Applicant: DuPont Nutrition Biosciences ApS, Copenhagen K (DK)

(72) Inventors: Ole Sibbesen, Bagsvaerd (DK); Jens Frisbaek Sorensen, Arhus N (DK)

(73) Assignee: DUPONT NUTRITION BIOSCIENCES APS (DK)

( * ) Notice: Subject to any disclaimer, the term of this patent is extended or adjusted under 35 U.S.C. 154(b) by 0 days.

(21) Appl. No.: 14/579,980

(22) Filed: Dec. 22, 2014

(65) Prior Publication Data

US 2015/0175992 A1 Jun. 25, 2015

Related U.S. Application Data

(63) Continuation of application No. 13/141,493, filed as application No. PCT/DK2009/050351 on Dec. 23, 2009, now Pat. No. 8,951,751.

(60) Provisional application No. 61/146,155, filed on Jan. 21, 2009.

(30) Foreign Application Priority Data

Dec. 23, 2008 (EP) .................................... 08172749

(51) Int. Cl.
| | |
|---|---|
| *C12N 15/00* | (2006.01) |
| *C12Q 1/34* | (2006.01) |
| *C07K 1/00* | (2006.01) |
| *C12N 9/24* | (2006.01) |
| *A23L 1/03* | (2006.01) |
| *A61K 38/47* | (2006.01) |

(52) U.S. Cl.
CPC .............. *C12N 9/2482* (2013.01); *A23L 1/034* (2013.01); *A61K 38/47* (2013.01); *C12N 9/248* (2013.01); *C12Y 302/01008* (2013.01)

(58) Field of Classification Search
CPC ................ C12N 9/2482; C12N 9/248; C12Y 302/01008

USPC ..................... 435/183, 320.1, 252.3; 530/350
See application file for complete search history.

(56) References Cited

U.S. PATENT DOCUMENTS

| | | | |
|---|---|---|---|
| 5,306,633 | A | 4/1994 | Gottschalk et al. |
| 5,817,500 | A | 10/1998 | Hansen et al. |
| 6,682,923 | B1 | 1/2004 | Bentzien et al. |
| 7,314,743 | B2 | 1/2008 | Clarkson et al. |
| 8,623,629 | B2 | 1/2014 | Sibbesen et al. |
| 2003/0180895 | A1 | 9/2003 | Sibbesen et al. |
| 2009/0155413 | A1 | 6/2009 | Sibbesen et al. |
| 2012/0021092 | A1 | 1/2012 | Sibbesen et al. |
| 2012/0028306 | A1 | 2/2012 | Sibbesen et al. |

FOREIGN PATENT DOCUMENTS

| | | |
|---|---|---|
| WO | WO 97/43409 A2 | 11/1997 |
| WO | WO 00/68396 A2 | 11/2000 |
| WO | WO 02/38746 A2 | 5/2002 |
| WO | WO 03/020923 A1 | 3/2003 |

OTHER PUBLICATIONS

Genbank Accession No. ABX42471.1, "Endo-1,4-beta-xylanase [Clostridium phytofermentans ISDg]," 2007, 1 page.
Genbank Accession No. ABR35180.1, "Endo-1,4-beta-xylanase [Clostridium beijerinckii NCIMB 8052]," 2007, 1 page.
Genbank Accession No. ACT03278.I, "Endo-1,4-beta-xylanase [*Paenibacillus* sp. JDR-2]," 2009, 1 page.
NCBI reference sequence YP_003013364.1, "Endo-1, 4-beta-xylanase [*Paenibacillus* sp. JDR-2]," 2009, 2 pages.
Hancock, S., et al., "Engineering of glycosidases and glycosyltransfereases," *Current Opinion in Chemical Biology*, 2006, vol. 10(5), pp. 509-519.
Kulkarni, N., et al., "Molecular and biotechnological aspects of xylanases," *FEMS Microbiology Reviews*, 1999, vol. 23(4) pp. 411-456.
Lee, et al., Uniprot database, accession No. Q9F9B9, Mar. 2001.
Kumar, P., et al., "The Tertiary Structure at 1.59 Å Resolution and the Proposed Amino Acid Sequence of a Family-11 Xylanase from the Thermophilic Fungus *Paecilomyes varioti* Bainier," *J. Mol. Biol.*, 2000, vol. 295, pp. 581-593.

*Primary Examiner* — Maryam Monshipouri

(57) ABSTRACT

The present invention relates to polypeptides with xylanase activity and uses thereof. The present invention also relates to method of modifying polypeptides with xylanase activity to affect, preferably to increase, xylanase activity and/or bran solubility.

21 Claims, 3 Drawing Sheets

```
            1                                                              60
 1    (1)   --------------------------------------------ASTDYWQNWTDGGGIVN
10    (1)   --------------MFKFVTKVLTVVIAATISFCLSAVPAS--ANTYWQYWTDGGGTVN
18    (1)   ---------------------------------------------NTYWQYWTDGGGTVN
11    (1)   ------MRQKKLTFILAFLVCFALTLPAEIIQAQIVTDNSIGNHDGYDYEFWKDSGGSGT
 6    (1)   ------MRQKKLTLILAFLVCFALTLPAEIIQAQIVTDNSIGNHDGYDYEFWKDSGGSGT
15    (1)   ----------------------------QIVTDNSIGNHDGYDYEFWKDSGGSGT
19    (1)   ----------------------------QIVTDNSIGNHDGYDYEFWKDSGGSGT
13    (1)   ------MNLRKLRLLFVMCIGLTLILTAVPAHARTITNNEMGNHSGYDYELWKDYG-NTS
21    (1)   ------------------------RTITNNEMGNHSGYDYELWKDYG-NTS
14    (1)   MKLFLAAIVLCATAATAFPSELAQRAAGDLSKRQSITTSQTGTNNGYYYSFWTNGGGEVT
22    (1)   ---------------AFPSELAQRAAGDLSKRQSITTSQTGTNNGYYYSFWTNGGGEVT
16    (1)   -------------------------------Q-TIQPGTGYNNGYFYSYWNDGHGGVT
 7    (1)   -MVSFTSLLAASPPSRASCRPAAEVESVAVEKRQ-TIQPGTGYNNGYFYSYWNDGHGGVT
 2    (1)   -------------------------------Q-CIQPGTGYNNGYFYSYWNDGHGGVT
 3    (1)   -------------------------------Q-TTPNSEGWHDGYYYSWWSDGGAQAT
 8    (1)   --MVGFTPVALAALAATGALAFPAGNATELEKRQ-TTPNSEGWHDGYYYSWWSDGGAQAT
 4    (1)   ------------------------------------------------WTDAQGTVS
17    (1)   --------------------------------------------TDYWQNWTDGGGTVN
 9    (1)   --------------MFKFGKKLLTVVLAASMSFGVFAATT--GATDYWQNWTDGGGTVN
12    (1)   --------------MFKFKKKFLVGLTAAFMSISMFSATASAAGTDYWQNWTDGGGTVN
20    (1)   -----------------------------------------AGTDYWQNWTDGGGTVN
 5    (1)   --------------MFKFKKNFLVGLSAALMSISLFSATASAASTDYWQNWTDGGGIVN 61                                                             120
 1   (18)   AVNGSGGNYSVNWSNTGNFVVGKG-------WTTGSPFRTINYNAGVWAPNGNGYLTLYG
10   (44)   ATNGPGGNYSVTWRDTGNFVVGKG-------WEIGSPNRTIHYNAGVWEPSGNGYLTLYG
18   (16)   ATNGPGGNYSVTWRDTGNFVVGKG-------WEIGSPNRTIHYNAGVWEPSGNGYLTLYG
11   (55)   MILNHGGTFSAQWNNVNNILFRKGKKFNETQTHQQVGNMSINYGANFQ-PNGNAYLCVYG
 6   (55)   MILNHGGTFSAQWNNVNNILFRKGKKFNETQTHQQVGNMSINYGANFQ-PNGNAYLCVYG
15   (28)   MILNHGGTFSAQWNNVNNILFRKGKKFNETQTHQQVGNMSINYGANFQ-PNGNAYLCVYG
19   (28)   MILNHGGTFSAQWNNVNNILFRKGKKFNETQTHQQVGNMSINYGANFQ-PNGNAYLCVYG
13   (54)   MTLNNGGAFSAGWNNIGNALFRKGKKFDSTRTHHQLGNISINYNASFN-PGGNSYLCVYG
21   (27)   MTLNNGGAFSAGWNNIGNALFRKGKKFDSTRTHHQLGNISINYNASFN-PGGNSYLCVYG
14   (61)   YTNGDNGEYSVTWVDCGDFTSGKG-------WNP-ANAQTVTYSGEFN-PSGNAYLAVYG
22   (45)   YTNGDNGEYSVTWVDCGDFTSGKG-------WNP-ANAQTVTYSGEFN-PSGNAYLAVYG
16   (27)   YTNGPGGQFSVNWSNSGNFVGGKG-------WQPGTKNKVINFSGSYN-PNGNSYLSVYG
 7   (59)   YTNGPGGQFSVNWSNSGNFVGGKG-------WQPGTKNKVINFSGSYN-PNGNSYLSVYG
 2   (27)   YCNGPGGQFSVNWSNSGNFVGGKG-------WQPGTKNRVINFSGSYN-PNGNSYLSVYG
 3   (27)   YTNLEGGTYEISWGDGGNLVGGKG-------WNPGLNARAIHFEGVYQ-PNGNSYLAVYG
 8   (58)   YTNLEGGTYEISWGDGGNLVGGKG-------WNPGLNARAIHFEGVYQ-PNGNSYLAVYG
 4   (10)   MDLGSGGTYSTQWRNTGNFVAGKG-------WSTGG-RKTVNY-SGTFNPSGNAYLTLYG
17   (16)   AVNGSGGNYSVNWQNTGNFVVGKG-------WTYGTPNRVVNYNAGVFSPSGNGYLTFYG
 9   (44)   AVNGSGGNYSVNWQNTGNFVVGKG-------WTYGTPNRVVNYNAGVFSPSGNGYLTFYG
12   (46)   AVNGSGGNYSVNWSNTGNFVVGKG-------WTTGSPFRTINYNAGVWAPNGNGYLTLYG
20   (18)   AVNGSGGNYSVNWSNTGNFVVGKG-------WTTGSPFRTINYNAGVWAPNGNGYLTLYG
 5   (46)   AVNGSGGNYSVNWSNTGNFVVGKG-------WTTGSPFRTINYNAGVWAPNGNGYLTLYG 121                                                            180
 1   (71)   WTRSPLIEYYVVDSWGTYRPTG--TYKGTVKSDGGTYDIYTTTRYNAPSIDGDRTTFTQY
10   (97)   WTRNQLIEYYVVDNWGTYRPTG--THRGTVVSDGGTYDIYTTMRYNAPSIDG-TQTFQQF
18   (69)   WTRNQLIEYYVVDNWGTYRPTG--THRGTVVSDGGTYDIYTTMRYNAPSIDG-TQTFQQF
11  (114)   WTVDPLVEYYIVDSWGNWRPPG-ATPKGTITVDGGTYDIYETLRVNQPSIKG-IATFKQY
 6  (114)   WTVDPLVEYYIVDSWGNWRPPG-ATPKGTITVDGGTYDIYETLRVNQPSIKG-IATFKQY
15   (87)   WTVDPLVEYYIVDSWGNWRPPG-ATPKGTITVDGGTYDIYETLRVNQPSIKG-IATFKQY
19   (87)   WTVDPLVEYYIVDSWGNWRPPG-ATPKGTITVDGGTYDIYETLRVNQPSIKG-IATFKQY
13  (113)   WTQSPLAEYYIVDSWGTYRPTG-AY-KGSFYADGGTYDIYETTRVNQPSIIG-IATFKQY
21   (86)   WTQSPLAEYYIVDSWGTYRPTG-AY-KGSFYADGGTYDIYETTRVNQPSIIG-IATFKQY
14  (112)   WTTDPLVEYYILESYGTYNPSSGLTSLGQVTSDGGTYDIYSTQRVNQPSIEG-TSTFNQY
22   (96)   WTTDPLVEYYILESYGTYNPSSGLTSLGQVTSDGGTYDIYSTQRVNQPSIEG-TSTFNQY
```

Fig. 2A

```
16   (79)  WSRNPLIEYYIVENFGTYNPSTGATKLGEVTSDGSVYDIYRTQRVNQPSIIG-TATFYQY
 7  (111)  WSRNPLIEYYIVENFGTYNPSTGATKLGEVTSDGSVYDIYRTQRVNQPSIIG-TATFYQY
 2   (79)  WSRNPLIEYYIVENFGTYNPSTGATKLGEVTSDGSVYDIYRTQRVNQPSIIG-TATFYQY
 3   (79)  WTRNPLVEYYIVENFGTYDPSSGATDLGTVECDGSIYRLGKTTRVNAPSIDG-TQTFDQY
 8  (110)  WTRNPLVEYYIVENFGTYDPSSGATDLGTVECDGSIYRLGKTTRVNAPSIDG-TQTFDQY
 4   (61)  WTTGPLIEYYIVDNWGTYRPTG--KYKGTVTSDGGTYDIYKTTRYNAPSIEG-TKTFDQY
17   (69)  WTRNALIEYYVVDNWGTYRPTG--TYKGTVTSDGGTYDIYTTMRYNQPSIDG-YSTFPQY
 9   (97)  WTRNALIEYYVVDNWGTYRPTG--TYKGTVTSDGGTYDIYTTMRYNQPSIDG-YSTFPQY
12   (99)  WTRSPLIEYYVVDSWGTYRPTG--TYKGTVKSDGGTYDIYTTTRYNAPSIDGDNTTFTQY
20   (71)  WTRSPLIEYYVVDSWGTYRPTG--TYKGTVKSDGGTYDIYTTTRYNAPSIDGDNTTFTQY
 5   (99)  WTRSPLIEYYVVDSWGTYRPTG--TYKGTVKSDGGTYDIYTTTRYNAPSIDGDRTTFTQY
            181                                                       240
 1  (129)  WSVRQSKRPTGSNATITFSNHVNAWKSHGMNLGSNWAYQVMATEGYQSSGSSNVTVW---
10  (154)  WSVRQSKRPTGNNVSITFSNHVNAWRNAGMNLGSSWSYQVLATEGYQSSGRSNVTVW---
18  (126)  WSVRQSKRPTGNNVSITFSNHVNAWRNAGMNLGSSWSYQVLATEGYQSSGRSNVTVW---
11  (172)  WSVRRSKR---TSGTISVSNHFRAWENLGMNMG-KMYEVALTVEGYQSSGSANVYSNTLR
 6  (172)  WSVRRSKR---TSGTISVSNHFRAWENLGMNMG-KMYEVALTVEGYQSSGSANVYSNTLR
15  (145)  WSVRRSKR---TSGTISVSNHFRAWENLGMNMG-KMYEVALTVEGYQSSGSANVYSNTLR
19  (145)  WSVRRSKR---TSGTISVSNHFRAWENLGMNMG-KMYEVALTVEGYQSSGSANVYSNTLR
13  (170)  WSVRQTKR---TSGTVSVSAHFRKWESLGMPMG-KMYETAFTVEGYQSSGSANVMTNQLF
21  (143)  WSVRQTKR---TSGTVSVSAHFRKWESLGMPMG-KMYETAFTVEGYQSSGSANVMTNQLF
14  (171)  WSVRTEKR---VGGTVTTANHFAAWKALGLEMG-TYNYMIVSTEGYESSGSSTITVS---
22  (155)  WSVRTEKR---VGGTVTTANHFAAWKALGLEMG-TYNYMIVSTEGYESSGSSTITVS---
16  (138)  WSVRRNHR---SSGSVNTANHFNAWAQQGLTLG-TMDYQIVAVEGYFSSGSASITVS---
 7  (170)  WSVRRNHR---SSGSVNTANHFNAWAQQGLTLG-TMDYQIVAVEGYFSSGSASITVS---
 2  (138)  WSVRRNHR---SSGSVNTANHFNAWAQQGLTLG-TMDYQIVAVEGYFSSGSASITVSD--
 3  (138)  WSVRQDKR---TSGTVQTGCHFDAWARAGLNVNGDHYYQIVATEGYFSSGYARITVADVG
 8  (169)  WSVRQDKR---TSGTVQTGCHFDAWARAGLNVNGDHYYQIVATEGYFSSGYARITVADVG
 4  (118)  WSVRQSKR---TGGTITSGNHFDAWARNGMNLG-NHNYMIMATEGYQSSGSSTITV----
17  (126)  WSVRQSKRPIGVNSQITFQNHVNAWASKGMYLGNSWSYQVMATEGYQSSGSSNVTVW---
 9  (154)  WSVRQSKRPIGVNSQITFQNHVNAWASKGMYLGNSWSYQVMATEGYQSSGSSNVTVW---
12  (157)  WSVRQSKRPTGSNAAITFSNHVNAWKSHGMNLGSNWAYQVLATEGYKSSGSSNVTVW---
20  (129)  WSVRQSKRPTGSNAAITFSNHVNAWKSHGMNLGSNWAYQVLATEGYKSSGSSNVTVW---
 5  (157)  WSVRQSKRPTGSNATITFSNHVNAWKSHGMNLGSNWAYQVMATEGYQSSGSSNVTVW---

241         261
 1  (186)  --------------------
10  (211)  --------------------
18  (183)  --------------------
11  (228)  INGNPLSTISNDKSITLDKNN
 6  (228)  INGNPLSTISNDESITLDKNN
15  (201)  INGNPLSTISNDESITLDKNN
19  (201)  INGNPLSTISNDKSITLDKNN
13  (226)  IGN-----------------
21  (199)  IGN-----------------
14  (224)  --------------------
22  (208)  --------------------
16  (191)  --------------------
 7  (223)  --------------------
 2  (192)  --------------------
 3  (195)  --------------------
 8  (226)  --------------------
 4  (170)  --------------------
17  (183)  --------------------
 9  (211)  --------------------
12  (214)  --------------------
20  (186)  --------------------
 5  (214)  --------------------
```

Fig. 2B

POLYPEPTIDES WITH XYLANASE ACTIVITY

CROSS-REFERENCE TO RELATED APPLICATIONS

This application is a continuation of U.S. patent application Ser. No. 13/141,493, filed Sep. 6, 2011, which was a national stage filing under 35 U.S.C. 371 of PCT/DK2009/050351, filed Dec. 23, 2009, which International Application was published by the International Bureau in English on Jul. 1, 2010, which claims benefit of U.S. Provisional Application No. 61/146,155, filed Jan. 21, 2009 and EP 08172749.7 filed Dec. 23, 2009, each of which are incorporated herein by reference.

FIELD OF THE INVENTION

The present invention relates to polypeptides with xylanase activity and uses thereof. The present invention also relates to method of modifying polypeptides with xylanase activity to affect, preferably to increase, xylanase activity and/or bran solubility.

BACKGROUND OF THE INVENTION

For many years, endo-β-1,4-xylanases (EC 3.2.1.8) (referred to herein as xylanases) have been used for the modification of complex carbohydrates derived from plant cell wall material. It is well known in the art that the functionality of different xylanases (derived from different micro organisms or plants) differs enormously. Based on structural and genetic information, xylanases have been classified into different Glycoside Hydrolase families (GH's) (Henrissat, 1991; Coutinho and Henrissat, 1999). Until recently, all known and characterized xylanases were belonging to the families GH10 or GH11. Recent work has identified numerous other types of xylanases belonging to the families GH5, GH7, GH8 and GH43 (Coutinho and Henrissat, 1999; Collins et al., 2005). Until now the GH11 family differs from all other GH's, being the only family solely consisting of xylan specific xylanases. The structure of the GH11 xylanases can be described as a β-Jelly roll structure (see FIG. 1, discussed herein).

U.S. Pat. No. 6,682,923 relates to xylanase activity proteins and nucleic acids.

Comprehensive studies characterising the functionality of xylanases have been done on well characterised and pure substrates (Kormelink et al., 1992). These studies show that different xylanases have different specific requirements with respect to substitution of the xylose backbone of the arabinoxylan (AX). Some xylanases require three un-substituted xylose residues to hydrolyse the xylose backbone; others require only one or two. The reasons for these differences in specificity are thought to be due to the three dimensional structure within the catalytic domains, which in turn is dependent on the primary structure of the xylanase, i.e. the amino acid sequence. However, the translation of these differences in the amino acid sequences into differences in the functionality of the xylanases, has up until now not been documented when the xylanase acts in a complex environment, such as plant material.

The xylanase substrates found in wheat (wheat flour), have traditionally been divided into two fractions: The water un-extractable AX (WU-AX) and the water extractable AX (WE-AX). The WU-AX:WE-AX ratio is approx. 70:30 in wheat flour. There have been numerous explanations as to why there are two different fractions of AX. The older literature (D'Appolonia and MacArthur (1976) and Montgomery and Smith (1955)) describes quite high differences in the substitution degree between WE-AX and WU-AX. The highest degree of substitution was found in WE-AX. This was used to explain why some of the AX was extractable. The high degree of substitution made the polymer soluble, compared to a lower substitution degree, which would cause hydrogen bonding between polymers and consequently precipitation.

The difference between the functionality of different xylanases has been thought to be due to differences in xylanase specificity and thereby their preference for the WU-AX or the WE-AX substrates.

However, more recent literature does not find the same huge differences between the substitution degree of the WE-AX and the WU-AX. Hence other parameters than the xylanases substrate specificity might be of importance. These parameters may be the xylanases preference for WE-AX versus WU-AX, determined by other means than classical substrate specificity. This parameter can be found described in literature as substrate selectivity.

In some applications (e.g. bakery) it is desirable to produce high molecular weight (HMW) soluble polymers from the WU-AX fraction. Such polymers have been correlated to a volume increase in bread making (Rouau, 1993; Rouau et al., 1994 and Courtin et al., 1999).

In other applications it is desirable to modify both the WU-AX and WE-AX, solubilising the WU-AX, making the molecular weight lower, reducing their hydrocolloid effect, produce arabinoxylan oligosaccharides, giving access to further degradation of other cell wall components (such as in crackers production, flour separation, feed application, Bio-ethanol production, Prebiotics, etc.).

All the above mentioned characteristics of xylanases used in various applications are directed to the xylanases performance and are of great importance to achieve the functionality needed. However, selection of xylanases having the right characteristics for a certain application or engineering known xylanases to achieve it, often results in a less efficient xylanase molecule, e.g., a molecule with low catalytic activity (i.e., specific activity characterised by the molecules units/mg xylanase protein). Since these molecules are to be used in commercial applications it is therefore of great importance to have as high a catalytic activity as possible. Improvement of this characteristic will be of more and more importance to achieve commercial application of these enzymes in the future, due to the increased use of agricultural by-products such as cereal bran or the use in cellulosic bio-ethanol production.

SUMMARY OF THE INVENTION

The present invention is predicated on the surprising finding that it is possible—by modifying a polypeptide with xylanase activity at position 110 compared to the B. subtilis xylanase polypeptide sequence shown as SEQ ID No. 1 to increase the bran solubilisation and/or xylanase activity of the enzyme.

Thus, it is has been shown by the inventors of the present invention that is possible to produce xylanase polypeptides having increased xylanase activity and/or bran solubilisation. This will, for example, make it feasible to hydrolyse the hemicellulosic fraction during cereal processing related to cellulosic bioethanol production, or allow a reduction in the amount of xylanase required in a number of applications such as animal feed, starch liquefaction, bakery, flour separation (wetmilling), production of prebiotics, and paper and pulp production.

In a first aspect, the present invention relates to a polypeptide having xylanase activity and comprising an amino acid sequence having at least 88% identity with SEQ ID No. 1 or having at least 75% identity with an amino acid sequence selected from SEQ ID No. 2-22, and which polypeptide has an amino acid modification in position 110, wherein said position 110 is determined as the position corresponding to position 110 of *B. subtilis* xylanase sequence shown as SEQ ID No. 1 by alignment.

In a second aspect, the present invention relates to a polypeptide having xylanase activity and comprising an amino acid sequence having at least 88% identity with SEQ ID No. 1 and which polypeptide has an amino acid modification in position 110, wherein said position 110 is determined as the position corresponding to position 110 of *B. subtilis* xylanase sequence shown as SEQ ID No. 1 by alignment.

In a third aspect, the present invention relates to a polypeptide having xylanase activity and comprising an amino acid sequence having at least 75% identity with SEQ ID No. 2 and which polypeptide has an amino acid modification in position 110, wherein said position 110 is determined as the position corresponding to position 110 of *B. subtilis* xylanase sequence shown as SEQ ID No. 1 by alignment.

In a further aspect, the present invention relates to a polypeptide having xylanase activity and comprising an amino acid sequence having at least 75% identity with SEQ ID No. 3 and which polypeptide has an amino acid modification in position 110, wherein said position 110 is determined as the position corresponding to position 110 of *B. subtilis* xylanase sequence shown as SEQ ID No. 1 by alignment.

In a further aspect, the present invention relates to a method of identifying a polypeptide according to the invention, said method comprising:
(i) preparing a polypeptide having at least 88% identity with SEQ ID No. 1 or having at least 75% identity with an amino acid sequence selected from SEQ ID No. 2-22, and which polypeptide has an amino acid modification in position 110, wherein said position 110 is determined as the position corresponding to position 110 of *B. subtilis* xylanase sequence shown as SEQ ID No. 1 by alignment;
(ii) comparing the bran solubilisation and/or xylanase activity of said polypeptide with the bran solubilisation and/or xylanase activity of the amino acid sequence selected among SEQ ID NOs: 1-22 with which is has the highest percentage of identity; and
(iii) selecting the polypeptide if it has improved bran solubilisation and/or improved xylanase activity compared to the amino acid sequence selected among SEQ ID NOs: 1-22 with which is has the highest percentage of identity.

In a further aspect, the present invention relates to a method of preparing a polypeptide according to the invention, said method comprising expressing a nucleotide sequence encoding said polypeptide; and optionally isolating and/or purifying the polypeptide after expression.

In some embodiments the polypeptide is prepared by modifying either a polypeptide amino acid sequence at position 110 or a codon that encodes an amino acid residue at position 110 in a nucleotide sequence encoding a polypeptide amino acid sequence, wherein position 110 is determined with reference to the *B. subtilis* xylanase sequence shown as SEQ ID No. 1.

In a further aspect, the present invention relates to a nucleotide sequence encoding a polypeptide according to the invention.

In a further aspect, the present invention relates to a vector comprising the nucleotide sequence encoding a polypeptide according to the invention.

In a further aspect, the present invention relates to a cell that has been transformed with the nucleotide sequence encoding a polypeptide according to the invention or the vector comprising the nucleotide sequence encoding a polypeptide according to the invention.

In a further aspect, the present invention relates to a host organism that has been transformed with the nucleotide sequence encoding a polypeptide according to the invention or the vector comprising the nucleotide sequence encoding a polypeptide according to the invention.

In a further aspect, the present invention relates to a composition comprising the polypeptide according to the invention.

In a further aspect, the present invention relates to a composition comprising a polypeptide identified according to the methods of the invention In a further aspect, the present invention relates to a composition comprising a polypeptide prepared according to the invention.

In a further aspect, the present invention relates to a composition comprising the nucleotide sequence encoding a polypeptide according to the invention.

In a further aspect, the present invention relates to a composition comprising the vector comprising the nucleotide sequence encoding a polypeptide according to the invention In a further aspect, the present invention relates to a composition comprising the cell that has been transformed with the nucleotide sequence encoding a polypeptide according to the invention.

In a further aspect, the present invention relates to a composition comprising the vector comprising the nucleotide sequence encoding a polypeptide according to the invention In a further aspect, the present invention relates to a composition comprising the organism that has been transformed with the nucleotide sequence encoding a polypeptide according to the invention or the vector comprising the nucleotide sequence encoding a polypeptide according to the invention admixed with a non toxic component.

In a further aspect, the present invention relates to a dough comprising the polypeptide according to the invention or a polypeptide identified according to the invention or a polypeptide prepared according to the invention or the nucleotide sequence according to the invention or the vector according to the invention or the cell according to the invention or the organism according to the invention admixed with a non toxic component or a composition according to the invention.

In a further aspect, the present invention relates to a bakery product comprising the polypeptide according to the invention or a polypeptide identified according to the invention or a polypeptide prepared according to the invention or the nucleotide sequence according to the invention or the vector according to the invention or the cell according to the invention or the organism according to the invention admixed with a non toxic component or a composition according to the invention or a dough according to the invention.

In a further aspect, the present invention relates to an animal feed comprising the polypeptide according to the invention or a polypeptide identified according to the invention or a polypeptide prepared according to the invention or the nucleotide sequence according to the invention or the vector according to the invention or the cell according to the invention or the organism according to the invention admixed with a non toxic component or a composition according to the invention.

In a further aspect, the present invention relates to a cleaning composition comprising xylanase. In some embodiments, the cleaning compositions are laundry detergent compositions, while in other embodiments the cleaning compositions are dishwashing detergents. In some further embodiments, the dishwashing detergents are automatic dishwashing detergents. In some additional embodiments, the xylanase-containing cleaning compositions further comprise one or more additional enzymes. In some embodiments, the additional enzymes are selected from hemicellulases, cellulases, peroxidases, proteases, xylanases, lipases, phospholipases, esterases, cutinases, pectinases, pectate lyases, mannanases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, and amylases, or mixtures thereof. In some embodiments, a combination of enzymes finds use (i.e., a "cocktail").

In a further aspect, the present invention relates to a method of degrading or modifying a plant cell wall which method comprises contacting said plant cell wall with the polypeptide according to the invention or a polypeptide identified according to the invention or a polypeptide prepared according to the invention or the nucleotide sequence according to the invention or the vector according to the invention or the cell according to the invention or the organism according to the invention admixed with a non toxic component or a composition according to the invention.

In a further aspect, the present invention relates to a method of processing a plant material which method comprises contacting said plant material with the polypeptide according to any one of the invention or a polypeptide identified according to the invention or a polypeptide prepared according to the invention or the nucleotide sequence according to the invention or the vector according to the invention or the cell according to the invention or the organism according to the invention admixed with a non toxic component or a composition according to the invention.

In a further aspect, the present invention relates to the use of the polypeptide according to the invention or a polypeptide identified according to the invention or a polypeptide prepared according to the invention or the nucleotide sequence according to the invention or the vector according to the invention or the cell according to the invention or the organism according to the invention admixed with a non toxic component or a composition according to the invention in a method of modifying plant materials.

In a further aspect, the present invention relates to the use of the polypeptide according to the invention or a polypeptide identified according to the invention or a polypeptide prepared according to the invention or the nucleotide sequence according to the invention or the vector according to the invention or the cell according to the invention or the organism according to the invention admixed with a non toxic component or a composition according to the invention in any one or more of: baking, processing cereals, starch liquefaction, production of Bio-ethanol from cellulosic material, animal feed, in processing wood, enhancing the bleaching of wood pulp.

In a further aspect, the present invention relates to a polypeptide or fragment thereof substantially as hereinbefore described with reference to the Examples and drawings.

In a further aspect, the present invention relates to a method substantially as hereinbefore described with reference to the Examples and drawings.

In a further aspect, the present invention relates to a composition substantially as hereinbefore described with reference to the Examples and drawings.

In a further aspect, the present invention relates to the use substantially as hereinbefore described with reference to the Examples and drawings.

LEGENDS TO THE FIGURE

Reference shall be made herein to the following Figure.

FIGS. 2A and 2B show a multiple sequence alignment of SEQ ID NO:1-22 in the AlignX program (part of the vectorNTI suite) with default parameters for multiple alignment (Gap opening penalty: 10 og Gap extension penalty 0.05). Numbers on the left of the sequence represent the SEQ ID NOs.

DETAILED DISCLOSURE OF THE INVENTION

Figure 1:
FIG. 1 shows the *Bacillus subtilis* XynA variant xylanase (T110A) (black), the *Trichoderma reesei* Xyn2 variant xylanase (T120A) (dark grey) and the *Thermomyces lanuginosus* XynA variant xylanase (T120A) (light grey) superimposed. The residues mutated, T110 and T120 respectively are highlighted.

Xylanase enzymes have been reported from nearly 100 different organisms, including plants, fungi and bacteria. The xylanase enzymes are classified into several of the more than 40 families of glycosyl hydrolase enzymes. The glycosyl hydrolase enzymes, which include xylanases, mannanases, amylases, β-glucanases, cellulases, and other carbohydrases, are classified based on such properties as the sequence of amino acids, the three dimensional structure and the geometry of the catalytic site (Gilkes, et al., 1991, Microbiol. Reviews 55: 303-315).

In one aspect, the present invention relates to a polypeptide having xylanase activity and comprising at least three, such as five, six, seven, eight, nine or ten amino acid substitutions relative to any one amino acid sequence of SEQ ID NO:1-22, and which polypeptide has an amino acid substitution in position 110, wherein said position 110 is determined as the position corresponding to position 110 of *B. subtilis* xylanase sequence shown as SEQ ID No. 1 by alignment.

In one aspect, the present invention relates to a polypeptide having xylanase activity and comprising an amino acid sequence, said amino acid sequence having at least 88% identity with SEQ ID No. 1 or having at least 75% identity with an amino acid sequence selected from 2-22 and which polypeptide has an amino acid modification in position 110, wherein said position 110 is determined as the position corresponding to position 110 of *B. subtilis* xylanase sequence shown as SEQ ID No. 1 by alignment.

The position of a particular amino acid within a polypeptide according to the present invention is determined by alignment of the amino acid sequence of said polypeptide with SEQ ID No. 1 using the a standard sequence alignment tool such as a by alignment of two sequences using the Smith-Waterman algorithm, or with the CLUSTALW2 algorithms, wherein the sequences are said to be aligned when the alignment score is highest. Alignment scores may be calculated according to the methods described by Wilbur, W. J. and Lipman, D. J. (1983) Rapid similarity searches of nucleic acid and protein data banks. Proc. Natl. Acad. Sci. USA, 80: 726-730. Preferably default parameters are used in the ClustalW2 (1.82) algorithm: Protein Gap Open Penalty=10.0; Protein Gap Extension Penalty=0.2; Protein matrix=Gonnet; Protein/DNA ENDGAP=−1; Protein/DNA GAPDIST=4.

Preferably a position of a particular amino acid within a polypeptide according to the present invention is determined by alignment of the amino acid sequence of the polypeptide with SEQ ID No. 1 using the AlignX program (part of the vectorNTI suite) with default parameters for multiple alignment (Gap opening penalty: 10 og Gap extension penalty 0.05). For some embodiments according to the present invention, alignment may be made by using FIG. 2 as described herein.

In a further aspect, the present invention relates to a polypeptide having xylanase activity and having an amino acid sequence having at least 88% identity with SEQ ID No. 1 and which polypeptide has an amino acid modification in position 110, wherein said position 110 is determined as the position corresponding to position 110 of *B. subtilis* xylanase sequence shown as SEQ ID No. 1 by alignment.

In a further aspect, the present invention relates to a polypeptide having xylanase activity and having at least 75% identity with SEQ ID No. 2 and which polypeptide has an amino acid modification in position 110, wherein said position 110 is determined as the position corresponding to position 110 of *B. subtilis* xylanase sequence shown as SEQ ID No. 1 by alignment.

In a further aspect, the present invention relates to a polypeptide having xylanase activity and having at least 75% identity with SEQ ID No. 3 and which polypeptide has an amino acid modification in position 110, wherein said position 110 is determined as the position corresponding to position 110 of *B. subtilis* xylanase sequence shown as SEQ ID No. 1 by alignment.

In a further aspect, the present invention relates to a polypeptide having xylanase activity and having at least 75% identity with SEQ ID No. 4 and which polypeptide has an amino acid modification in position 110, wherein said position 110 is determined as the position corresponding to position 110 of *B. subtilis* xylanase sequence shown as SEQ ID No. 1 by alignment.

In a further aspect, the present invention relates to a polypeptide having xylanase activity and comprising an amino acid sequence having at least 75% identity with SEQ ID No. 1, and which polypeptide has an amino acid substitution in position 110 to any one different amino acid residue selected from the group consisting of: glutamic acid, tryptophan, alanine and cysteine, wherein said position 110 is determined as the position corresponding to position 110 of *B. subtilis* xylanase sequence shown as SEQ ID No. 1 by alignment.

Unless otherwise stated the term "Sequence identity" for amino acids as used herein refers to the sequence identity calculated as $(n_{ref}-n_{dif}) \cdot 100/n_{ref}$, wherein $n_{dif}$ is the total number of non-identical residues in the two sequences when aligned and wherein $n_{ref}$ is the number of residues in one of the sequences. Hence, the amino acid sequence ASTDYWQNWT will have a sequence identity of 80% with the sequence ASTGYWQAWT ($n_{dif}=2$ and $n_{ref}=10$).

In some embodiments the sequence identity is determined by conventional methods, e.g., Smith and Waterman, 1981, Adv. Appl. Math. 2:482, by the search for similarity method of Pearson & Lipman, 1988, Proc. Natl. Acad. Sci. USA 85:2444, using the CLUSTAL W algorithm of Thompson et al., 1994, Nucleic Acids Res 22:467380, by computerized implementations of these algorithms (GAP, BESTFIT, FASTA, and TFASTA in the Wisconsin Genetics Software Package, Genetics Computer Group). The BLAST algorithm (Altschul et al., 1990, Mol. Biol. 215:403-10) for which software may be obtained through the National Center for Biotechnology Information www.ncbi.nlm.nih.gov/) may also be used. When using any of the aforementioned algorithms, the default parameters for "Window" length, gap penalty, etc., are used.

The term "modification" as used herein means any chemical modification to any one amino acid or to the amino acid sequence of the polypeptide selected from SEQ ID NO: 1-22, as well as genetic manipulation of the DNA encoding that polypeptide. The modification can be substitutions, deletions and/or insertions of one or more amino acids as well as replacements of one or more amino acid side chains. In some embodiments, the polypeptides have xylanase activity only have amino acid substitutions relative to SEQ ID No.1-22.

It is to be understood that "modification" in a given polypeptide is relative to the polypeptide selected from SEQ ID NO: 1-22 with the highest percentage sequence identity to this given polypeptide.

The terminology for amino acid substitutions used in this description is as follows. The first letter represents the amino acid naturally present at a position of a particular sequence. The following number represents the position relative to SEQ ID No. 1. The second letter represents the different amino acid substituting for the natural amino acid. An example is D11F/R122D/T110A, wherein the aspartic acid at position 11 of SEQ ID NO:1 is replaced by a phenylalanine and the arginine at position 122 of SEQ ID NO:1 is replaced by an aspartic acid, and the threonine at position 110 is replaced by an alanine, all three mutations being in the same polypeptide having xylanase activity.

Apart from the amino acid modifications in the polypeptides with xylanase activity according to the invention, the polypeptides may have further amino acid modifications of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In, The Proteins, Academic Press, New York. The most commonly occurring exchanges are Ala to Ser, Val to Ile, Asp to Glu, Thr to Ser, Ala to Gly, Ala to Thr, Ser to Asn, Ala to Val, Ser to Gly, Tyr to Phe, Ala to Pro, Lys to Arg, Asp to Asn, Leu to Ile, Leu to Val, Ala to Glu, and Asp to Gly.

In addition to the 20 standard amino acids, non-standard amino acids (such as 4-hydroxyproline, 6-/V-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

The term "host organism", as used herein, includes any cell type which is susceptible to transformation, transfection, transduction, and the like with a nucleic acid construct or expression vector comprising a polynucleotide encoding the polypeptides of the present invention.

For the present purposes, a xylanase means a protein or a polypeptide having xylanase activity.

The phrase "a polypeptide having xylanase activity" as used herein refers to any protein or polypeptide that has activity in a xylanase assay such as described herein.

Xylanase activity can be measured using any assay, in which a substrate is employed that includes 1,4-beta-D-xylosidic endo-linkages in xylans. The pH and the temperature used in the assay are to be adapted to the xylanase in question. Examples of suitable pH values are 4, 5, 6, 7, 8, 9, 10 or 11. Examples of suitable temperatures are 30, 35, 37, 40, 45, 50, 55, 60, 65, 70 or 80° C. Different types of substrates are available for the determination of xylanase activity e.g. Xylazyme tablets (crosslinked, dyed xylan substrate, Megazyme, Bray, Ireland).

Preferably, xylanase activity is measured using the following assay.

Xylanase Assay (Endo-β-1,4-Xylanase Activity)

Samples were diluted in citric acid (0.1 M)-di-sodium-hydrogen phosphate (0.2 M) buffer, pH 5.0, to obtain approx. $OD_{590}$=0.7 in this assay. Three different dilutions of the sample were pre-incubated for 5 minutes at 40° C. At time=5 minutes, 1 Xylazyme tablet (crosslinked, dyed xylan substrate, Megazyme, Bray, Ireland) was added to the enzyme solution in a reaction volume of 1 ml. At time=15 minutes the reaction was terminated by adding 10 ml of 2% TRIS/NaOH, pH 12. Blanks were prepared using 1000 µl buffer instead of enzyme solution. The reaction mixture was centrifuged (1500×g, 10 minutes, 20° C.) and the OD of the supernatant was measured at 590 nm. One xylanase unit (XU) is defined as the xylanase activity increasing $OD_{590}$ with 0.025 per minute.

The substrate (cross-linked and dyed arabinoxylan extracted from wheat) used in the above assay is a good approximate to the corresponding substrate in commercial applications.

Enzymes can furthermore be classified on the basis of the handbook Enzyme Nomenclature from NC-IUBMB, 1992), see also the ENZYME site at the internet: www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB) and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

In one aspect of the invention, the xylanase is an enzyme classified as EC 3.2.1.8. The official name is endo-1,4-beta-xylanase. The systematic name is 1,4-beta-D-xylan xylanohydrolase. Other names may be used, such as endo-(1-4)-beta-xylanase; (1-4)-beta-xylan 4-xylanohydrolase; endo-1, 4-xylanase; xylanase; beta-1,4-xylanase; endo-1,4-xylanase; endo-beta-1,4-xylanase; endo-1,4-beta-D-xylanase; 1, 4-beta-xylan xylanohydrolase; beta-xylanase; beta-1, 4-xylan xylanohydrolase; endo-1,4-beta-xylanase; beta-D-xylanase. The reaction catalyzed is the endohydrolysis of 1, 4-beta-D-xylosidic linkages in xylans.

Another classification of certain glycoside hydrolase enzymes, such as endoglucanase, xylanase, galactanase, mannanase, dextranase and alpha-galactosidase, in families based on amino acid sequence similarities has been proposed a few years ago. They currently fall into 90 different families: See the CAZy(ModO) internet site (Coutinho, P. M. & Henrissat, B. (1999) Carbohydrate-Active Enzymes server at: afmb.cnrs-mrs.fr/~cazy/CAZY/index.html (corresponding papers: Coutinho, P. M. & Henrissat, B. (1999) Carbohydrate-active enzymes: an integrated database approach. In "Recent Advances in Carbohydrate Bioengineering", H J. Gilbert, G. Davies, B. Henrissat and B. Svensson eds., The Royal Society of Chemistry, Cambridge, pp. 3-12; Coutinho, P. M. & Henrissat, B. (1999) The modular structure of cellulases and other carbohydrate-active enzymes: an integrated database approach. In "Genetics, Biochemistry and Ecology of Cellulose Degradation", K. Ohmiya, K. Hayashi, K. Sakka, Y. Kobayashi, S. Karita and T. Kimura eds., Uni Publishers Co., Tokyo, pp. 15-23).

In one aspect of the invention, the xylanase of the invention is a xylanase of Glycoside Hydrolyase (GH) Family 11. The term "of Glycoside Hydrolyase (GH) Family 11" means that the xylanase in question is or can be classified in the GH family 11.

It is to be understood that protein similarity searches (like ProteinBlast at e.g. toolkit.tuebingen.mpg.de/prot_blast) may not necessarily determine whether an unknown sequence actually falls under the term of a GH11 xylanase family member. Proteins sequences found using a blast search might have relatively high identity/homology and still not be actual xylanases, and furthermore, not be xylanases belonging to GH11. Alternatively, protein sequences may have a relatively low primary amino acid sequence identity and still be a GH11 xylanase family member. To determine whether an unknown protein sequence actually is a xylanase protein within the GH11 family, the evaluation will have to be done, not only on sequence similarity, but also on 3D—structure similarity, since the classification within GH-families rely on the 3D fold. A software that will predict the 3D fold of an unknown protein sequence is HHpred (toolkit.tuebingen.mpg.de/hhpred). The power of this software for protein structure prediction relies on identifying homologous sequences with known structure to be used as template. This works so well because structures diverge much more slowly than primary sequences. Proteins of the same family may have very similar structures even when their sequences have diverged beyond recognition.

In practice, an unknown sequence can be pasted into the software (toolkit.tuebingen.mpg.de/hhpred) in FASTA format. Having done this, the search can be submitted. The output of the search will show a list of sequences with known 3D structures. To confirm that the unknown sequence indeed is a GH11 xylanase, GH11 xylanases should be found within the list of homologues having a probability of >90. Not all proteins identified as homologues will be characterised as GH11 xylanases, but some will. The latter proteins are proteins with a known structure and biochemically characterisation identifying them as xylanases. The former have not been biochemically characterised as GH11 xylanases. Several references describes this protocol such as Söding J. (2005) Protein homology detection by HMM-HMM comparison. Bioinformatics 21, 951-960 (doi:10.1093/bioinformatics/bti125) and Söding J, Biegert A, and Lupas A N. (2005) The HHpred interactive server for protein homology detection and structure prediction. Nucleic Acids Research 33, W244-W248 (Web Server issue) (doi:10.1093/nar/gki40).

According to the Cazy(ModO) site, Family 11 glycoside hydrolases can be characterised as follows:
Known Activities: xylanase (EC 3.2.1.8)
Mechanism: Retaining
Catalytic Nucleophile/Base: Glu (experimental)
Catalytic Proton Donor: Glu (experimental)
3D Structure Status: Fold: β-jelly roll
Clan: GH-C As used herein, "Clan C" refers to groupings of families which share a common three-dimensional fold and identical catalytic machinery (see, for example, Henrissat, B. and Bairoch, A., (1996) Biochem. J., 316, 695-696).

As used herein, "Family 11" refers to a family of enzymes as established by Henrissat and Bairoch (1993) Biochem J., 293,781-788 (see, also, Henrissat and Davies (1997) Current Opinion in Structural Biol. 1997, &: 637-644). Common features for family 11 members include high genetic homology, a size of about 20 kDa and a double displacement catalytic mechanism (see Tenkanen et al., 1992; Wakarchuk et al., 1994). The structure of the family 11 xylanases includes two large β-sheets made of β-strands and α-helices.

Family 11 xylanases include but are not limited to the following: *Aspergillus niger* XynA, *Aspergillus kawachii* XynC, *Aspergillus tubigensis* XynA, *Bacillus circulans* XynA, *Bacilluspunzilus* XynA, *Bacillus subtilis* XynA, *Neocalliniastix patriciarum* XynA, *Streptomyces lividans* XynB, *Streptomyces lividans* XynC, *Streptomyces therinoviolaceus* XynII, *Thermomonospora fusca* XynA, *Trichoderma harzianum* Xyn, *Tyichoderma reesei* XynI, *Trichoderma reesei* XynII, *Trichodermaviride* Xyn.

As used herein, "wild-type" refers to a sequence or a protein that is native or naturally occurring.

In another particular embodiment, the xylanase of the invention is derived from a bacterial xylanase, such as from a bacterium of (i) the phylum of Firmicutes; (ii) the class of Bacilli; (iii) the order of Bacillales; (iv) the family of Paenibacillaceae; or (v) the genus of *Paenibacillus*; such as from a bacterium of (vi) the species of *Paenibacillus pabuli, Paenibacillus polymyxa*, or *Paenibacillus* sp.; such as from (vii) strains of *Paenibacillus pabuli*, or *Paenibacillus polymyxa*.

The expression "xylanase derived from a bacterial xylanase" as used herein above includes any wild-type xylanase isolated from the bacterium in question, as well as variants or fragments thereof which retain xylanase activity.

In a further particular embodiment, the xylanase of the invention is derived from a fungal xylanase.

The above definition of "derived from" (in the context of bacterial xylanases) is applicable by analogy also to fungal xylanases.

Examples of fungal xylanases of family 11 glycoside hydrolase are those which can be derived from the following fungal genera: *Aspergillus, Aureobasidium, Emericella, Fusarium, Gaeumannomyces, Humicola, Lentinula, Magnaporthe, Neocallimastix, Nocardiopsis, Orpinomyces, Paecilomyces, Penicillium, Pichia, Schizophyllum, Talaromyces, Thermomyces, Trichoderma*.

Fungal xylanases include yeast and filamentous fungal xylanases. In some embodiments, the xylanase is derived from a fungus of (i) the phylum of Ascomycota; (ii) the class of Pezizomycotina; (iii) the order of Eurotiomycetes; (iv) the sub-order of Eurotiales; (v) the family of Trichocomaceae, such as the mitosporic Trichocomaceae; or from a fungus of (vi) the genus *Aspergillus*; such as from (vii) strains of *Aspergillus niger*. It will be understood that the definition of the aforementioned species includes both the perfect and imperfect states, and other taxonomic equivalents e.g., anamorphs, regardless of the species name by which they are known. Those skilled in the art will readily recognize the identity of appropriate equivalents.

Strains of the abovementioned bacteria and fungi are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

Questions relating to taxonomy can be solved by consulting a taxonomy data base, such as the NCBI Taxonomy Browser which is available at the following internet site: www.ncbi.nlm.nih.gov/Taxonomy/taxonomyhome.html/.
However, preferably reference is to the following handbooks: Dictionary of the Fungi, 9th edition, edited by Kirk, P. M., P. F. Cannon, J. C. David & J. A. Stalpers, CAB Publishing, 2001; and Bergey's Manual of Systematic Bacteriology, Second edition (2005).

The present invention relates to modification(s) at certain amino acid position(s). These position(s) are listed with reference to the *B. subtilis* amino acid sequence shown as SEQ ID No. 1. In the present invention, the polypeptides with xylanase activity have a modification at least in position 110 compared to the *B. subtilis* sequence shown as SEQ ID No. 1. Equivalent positions in other family 11 xylanases may be found by aligning other Family 11 xylanases with SEQ ID No. 1 and determining which amino acid aligns with the specific amino acid of SEQ ID No. 1 (e.g., see Example 5). Such alignment and use of one sequence as a first reference is simply a matter of routine for one of ordinary skill in the art.

In one aspect, a variant xylanase according to the invention has an improved bran solubilisation activity which is higher than what may be obtained by use of the corresponding wild-type xylanase, or any one xylanase comprising an amino acid sequence selected from SEQ ID No. 2-22 as measured in a "bran solubilisation assay".

In one aspect, the xylanase according to the invention has an improved bran solubilisation activity as a result of the modification in position 110.

Suitably, xylanase bran solubilising activity may be measured using the bran solubilising assay provided herein. Thus, polypeptides having increased xylanase activity and/or increased bran solubilising activity may be provided. The requirement for specificity towards the WU-AX is increasingly more and more important, since many applications are using elevated concentration of cereal bran. The bread making industry increases the bran concentration in many products, due to health and nutritional issues, the feed industry incorporates increasing amount of bran material (fibre, Distillers Dried Grains with Solubles (DDGS)) due to the use of cereal in Bioethanol production, for example. It is therefore advantageous to provide new xylanases with increased specificity, and hence efficacy in solubilising this bran material.

Bran Solubilisation Assay

Preferably, bran solubility is measured using the following assay.

A suspension of wheat bran in (0.1 M)-di-sodium-hydrogen phosphate (0.2 M) buffer, pH 5.0 is prepared to an concentration of 1.33% bran (w/w). From this suspension, aliquots of 750 µl are transferred into eppendorph tubes under stirring. Each substrate tube is pre-heated for 5 minutes at 40° C. Hereto, 250 µl enzyme solution is added, making the end concentration of substrate 1%. Three dilutions (in duplicate) are made from each xylanases, with increasing enzyme concentration (0.33; 1.0 and 3.0 µg xylanase/gram bran) to each time of determination (0, 30, 60 and 240 minutes). As blank, a heat denatured solution of the xylanase is used. The reaction is terminated to the given times, by transferring the tubes to a incubator set at 95° C. Heat denaturated samples are kept at 4° C. until all enzyme reactions are terminated. When all enzyme reactions are terminated, Eppendorph tubes are centrifuged to obtain a clear supernatant. The enzymes capability to solubilise bran is expressed as the increase in reducing end groups as determined using PAHBAH (Lever, 1972).

Since side activities, such as amylase activity, may interfere with the above assay, bran solubilisation assay should only be carried out on purified xylanase samples (see Ex. 2).

In one aspect, the xylanase according to the invention has a reduced sensitivity to a xylanase inhibitor as compared to any one wild type xylanase, or any one xylanase comprising an amino acid sequence selected from SEQ ID No. 2-22.

In a further aspect, the polypeptide having xylanase activity according to the invention has a reduced sensitivity to a xylanase inhibitor as a result of the modification in position 110 in combination with one or more modification(s) at any one or more of amino acid positions: 11, 12, 13, 34, 54, 77, 81, 99, 104, 113, 114, 118, 122, 141, 154, 159, 162, 164, 166 and 175.

The inhibitor may be an inhibitor found naturally in plant tissues.

As used herein, the term "xylanase inhibitor" refers to a compound, typically a protein, whose role is to control the depolymerisation of complex carbohydrates, such as arabinoxylan, found in plant cell walls. These xylanase inhibitors are capable of reducing the activity of naturally occurring xylanase enzymes as well as those of fungal or bacterial origin. Although the presence of xylanase inhibitors have been reported in cereal seeds (see for example McLauchlan et al 1999a; Rouau and Suget 1998).

McLauchlan et al (1999a) disclose the isolation and characterisation of a protein from wheat that binds to and inhibits two family-11 xylanases. Likewise, WO 98/49278 demonstrates the effect of a wheat flour extract on the activity of a group of microbial xylanases all of which are classified as family 11 xylanases. Debyser et al. (1999) also disclose that endoxylanases from *Aspergillus niger* and *Bacillus subtilis*, which are both members of the family 11 xylanases were inhibited by a wheat xylanase inhibitor called TAXI. McLauchlan et al (1999b) teach that extracts from commercial flours such as wheat, barley, rye and maize are capable of inhibiting both family 10 and 11 xylanases.

The xylanase inhibitor may be any suitable xylanase inhibitor. By way of example, the xylanase inhibitor may be the inhibitor described in WO-A-98/49278 and/or the xylanase inhibitor described by Rouau, X. and Surget, A. (1998), McLauchlan, R., et al. (1999) and/or the xylanase inhibitor described in UK patent application number 9828599.2 (filed 23 Dec. 1998), UK patent application number 9907805.7 (filed 6 Apr. 1999) and UK patent application number 9908645.6 (filed 15 Apr. 1999).

The inhibitors described in the prior art may also be used in assays to determine the sensitivity of a variant polypeptide of the invention to xylanase inhibitors. They may also be used as described below to modulate the functionality of a xylanase.

Xylanase Inhibitor Assay

Preferably, xylanase inhibition activity is measured using the following assay.

100 μl inhibitor preparation (containing various concentrations of xylanase inhibitor (for quantification see Xylanase inhibitor quantification below)), 250 μl xylanase solution (containing 12 XU xylanase/ml) and 650 μl buffer (0.1 M citric acid—0.2M di-sodium hydrogen phosphate buffer, 1% BSA (Sigma-Aldrich, USA), pH 5.0) was mixed. The mixture was thermostated for 5 minutes at 40.0° C. At time=5 minutes one Xylazyme tablet was added. At time=15 minutes reaction was terminated by adding 10 ml 2% TRIS/NaOH, pH 12. The reaction mixture was centrifuged (1500×g, 10 minutes, 20° C.) and the supernatant measured at 590 nm. The xylanase inhibition was calculated as residual activity in %, compared to the blank.

The endogenous endo-β-1,4-xylanase inhibitor used is obtainable from wheat flour. The inhibitor is a di-peptide, having a MW of about 40 kDa (as measured by SDS-PAGE or mass spectrometry) and a pI of about 8 to about 9.5. Sequence analysis to date has revealed that the inhibitor has the sequence presented as SEQ ID No. 24 or is highly homologous thereto.

A method to quantify the inhibitor concentration in a give inhibitor preparation can be found in Ex. 3

Blanks were prepared the same way, but substituting the inhibitor solution with water.

The present invention also relates to nucleotide sequence encoding a polypeptide according to the invention comprising a nucleotide sequence operably linked to one or more control sequences that direct the expression of the coding sequence in a suitable host cell under conditions compatible with the control sequences. A polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence which is recognized by a host cell for expression of a polynucleotide encoding a polypeptide of the present invention. The promoter sequence contains transcriptional control sequences which mediate the expression of the polypeptide. The promoter may be any nucleotide sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene {amyM), *Bacillus amyloliquefaciens* alpha-amylase gene {amyQ), *Bacillus licheniformis* penicillinase gene (penP), *Bacillus subtilis* xylA and xylB genes, and prokaryotic beta-lactamase gene (Villa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase {glaA), *Rhizomucor miehei* lipase, *Aspergillus oryzae* alkaline protease, *Aspergillus oryzae* triose phosphate isomerase,

*Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* those phosphate isomerase (TPI), *Saccharomyces cerevisiae* metallothionine (CUP1), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator which is functional in the host cell of choice may be used in the present invention.

Terminators for filamentous fungal host cells may be obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease. Terminators for yeast host cells may be obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleotide sequence encoding the polypeptide. Any leader sequence that is functional in the host cell of choice may be used in the present invention.

Leaders for filamentous fungal host cells may be obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and which, when transcribed, is recognized by the host cell as a signal to add polyadenosine residues to transcribed mRNA. Any polyadenylation sequence which is functional in the host cell of choice may be used in the present invention.

Polyadenylation sequences for filamentous fungal host cells may be obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus* n/geralpha-glucosidase.

Useful polyadenylation sequences for yeast host cells are described by Guo and Sherman, 1995, Molecular Cellular Biology 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleotide sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice, i.e., secreted into a culture medium, may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprf), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tec, and tip operator systems. In yeast, the ADH2 system or GAL1 system may be used. In filamentous fungi, the TAKA alpha-amylase promoter, Aspergillus niger glucoamylase promoter, and Aspergillus oryzae glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleotide sequence encoding the polypeptide would be operably linked with the regulatory sequence.

The present invention also relates to recombinant expression vectors comprising a polynucleotide encoding the polypeptide of the present invention, a promoter, and transcriptional and translational stop signals. The various nucleic acids and control sequences described herein may be joined together to produce a recombinant expression vector which may include one or more convenient restriction sites to allow for insertion or substitution of the nucleotide sequence encoding the polypeptide at such sites. Alternatively, a nucleotide sequence encoding the polypeptide of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from Bacillus subtilis or Bacillus licheniformis, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. In some embodiments the amdS and pyrG genes of Aspergillus nidulans or Aspergillus oryzae and the bar gene of Streptomyces hygroscopicus are used in an Aspergillus cell.

The vectors of the present invention preferably contain an element(s) that permits integration of the vector into the host cell's genome or autonomous replication of the vector in the cell independent of the genome. For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination. For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in E. coli, and pUB1 10, pE194, pTA1060, and pAMβi permitting replication in Bacillus.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et a/., 1991, Gene 98: 61-67; Cullen et al., 1987, Nucleic Acids Research 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

The present invention also relates to recombinant host cells, comprising a polynucleotide encoding the polypeptide of the present invention, which are advantageously used in the recombinant production of the polypeptides. A vector comprising a polynucleotide encoding the polypeptide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote. Useful unicellular microorganisms are bacterial cells such as gram positive bacteria including, but not limited to, a *Bacillus* cell, e.g., *Bacillus alkalophilus, Bacillus amyloliquefaciens. Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In one aspect, the bacterial host cell is a *Bacillus lentus, Bacillus licheniformis, Bacillus stearothermophilus*, or *Bacillus subtilis* cell. In another aspect, the *Bacillus* cell is an alkalophilic *Bacillus*. The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizen, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278).

The host cell may also be a eukaryote, such as a mammalian, insect, plant, or fungal cell.

In one aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra). In another aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, F. A., Passmore, S. M., and Davenport, R. R., eds, Soc. App. Bacteriol. Symposium Series No. 9, 1980).

In an even further aspect, the yeast host cell is a *Candida, Hansenula, Kluyveromyces, Pichia, Saccharomyces, Schizosaccharomyces*, or *Yarrowia* cell.

In one particular aspect, the yeast host cell is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* cell. In another aspect, the yeast host cell is a *Kluyveromyces lactis* cell. In another aspect, the yeast host cell is a *Yarrowia lipolytica* cell.

In another aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In another aspect, the filamentous fungal host cell is an *Acremonium, Aspergillus, Aureobasidium, Bjerkandera, Ceriporiopsis, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

In another aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In another aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell. Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, Proceedings of the National Academy of Sciences USA 81: 1470-1474. Suitable methods for transforming *Fusarium* species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, Journal of Bacteriology 153: 163; and Hinnen et a/., 1978, Proceedings of the National Academy of Sciences USA 75; 1920.

The present invention also relates to methods for producing a polypeptide of the present invention, comprising: (a) cultivating a cell, which in its wild-type form is capable of producing the polypeptide, under conditions conducive for production of the polypeptide; and (b) recovering the polypeptide. Preferably, the cell is of the genus *Aspergillus* and more preferably *Aspergillus fumigatus*.

The present invention also relates to methods for producing a polypeptide of the present invention, comprising: (a) cultivating a host cell under conditions conducive for production of the polypeptide; and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate.

For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation. The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J.-C. Janson and Lars Ryden, editors, VCH Publishers, New York, 1989) to obtain substantially pure polypeptides.

In one aspect, the amino acid modification in position 110 is an amino acid substitution.

In one aspect, the amino acid modification in position 110 is an amino acid deletion.

In one aspect, the amino acid modification in position 110 is an amino acid insertion.

In some embodiments, the sequence identity is measured relative to SEQ ID No. 1, wherein the amino acid sequence according to SEQ ID No. 1 further comprises a signal peptide sequence, such as its natural signal peptide sequence.

In some embodiments, the polypeptide according to the invention has at least 90, 92 or 95% identity with SEQ ID No. 1.

In some embodiments, the polypeptide according to the invention has at least 76, 78, 80, 85, 90, 95, 98 or 95% identity with the sequence with which is has the highest percentage of identity selected from SEQ ID No. 2-22.

In some embodiments, the polypeptide according to the invention has at least 76, 78, 80, 85, 90, 95, 98 or 95% identity with SEQ ID No. 2.

In some embodiments, the polypeptide according to the invention has at least 76, 78, 80, 85, 90, 95, 98 or 95% identity with SEQ ID No. 3.

In some embodiments, the polypeptide according to the invention has a J-jelly roll fold.

In some embodiments according to the invention the amino acid modification in position 110 is an amino acid substitution.

In some embodiments according to the invention the amino acid modification in position 110 is a substitution to any one different amino acid residue selected from the group consisting of: alanine, arginine, asparagine, aspartic acid, cysteine, glutamic acid, glutamine, glycine, histidine, isoleucine, leucine, lysine, methionine, phenylalanine, proline, serine, tryptophan, tyrosine and valine.

In some embodiments according to the invention the amino acid modification in position 110 is a substitution to any one different amino acid residue selected from the group consisting of: alanine, arginine, asparagine, cysteine, glutamic acid, glutamine, glycine, histidine, isoleucine, leucine, lysine, methionine, phenylalanine, proline, serine, tryptophan, tyrosine and valine.

In some embodiments according to the invention the amino acid modification in position 110 is a substitution to any one different amino acid residue selected from the group consisting of: glutamic acid, tryptophan, alanine and cysteine.

In some embodiments according to the invention the amino acid modification in position 110 is a substitution to alanine.

In some embodiments, the polypeptide according to the invention has a total number of amino acids of less than 250, such as less than 240, such as less than 230, such as less than 220, such as less than 210, such as less than 200 amino acids, such as in the range of 160 to 240, such as in the range of 160 to 220 amino acids.

In some embodiments, the polypeptide according to the invention comprises one or more modification(s) at any one or more of amino acid positions: 11, 12, 13, 34, 54, 77, 81, 99, 104, 113, 114, 118, 122, 141, 154, 159, 162, 164, 166 and 175, the position(s) being determined as the corresponding position of B. subtilis amino acid sequence shown as SEQ ID No. 1.

In some embodiments, the polypeptide according to the invention comprises one or more amino acid substitutions selected from the group consisting of: 11F, 12F, 54Q, 54W, 122D, 113A, 13Y, 113D, 175L, 122F, 34K, 99Y, 104W, 141Q, 154R, 159D, 175K, 81I, 166F, 162E, 162D, 164F, 114D, 114Y, 114F, 118V, 175K, 77L, 77M, 77S, 77V, and 77Y, the position(s) being determined as the corresponding position of B. subtilis amino acid sequence shown as SEQ ID No. 1.

In some embodiments, the polypeptide according to the invention comprises one or more amino acid substitutions selected from the group consisting of: D11F, G12F, N54Q, R122D, Y113A, G13Y, Y113D, N141Q, Q175L, R122F, G34K, K99Y, T104W, K154R, N159D, Q175K, V81I, Y166F, S162E, S162D, W164F, N114D, N114Y, N114F, I118V, I77L, I77M, I77S, I77V, and I77Y, the position(s) being determined as the corresponding position of B. subtilis amino acid sequence shown as SEQ ID No. 1.

In some embodiments, the polypeptide according to the invention comprises one or more modification(s) at any one or more of amino acid positions: 13, 99, 104, 113, 122, 154, 159 and 175, the position(s) being determined as the corresponding position of B. subtilis amino acid sequence shown as SEQ ID No. 1.

In some embodiments, the polypeptide according to the invention comprises substitution(s) at the amino acid positions: 13, 99, 104, 113, 122, 154, 159 and 175, the position(s) being determined as the corresponding position of B. subtilis amino acid sequence shown as SEQ ID No. 1.

In some embodiments, the polypeptide according to the invention further comprises one or more modification(s) at any one or more of amino acid positions: 114 and 166, the position(s) being determined as the corresponding position of *B. subtilis* amino acid sequence shown as SEQ ID No. 1.

In some embodiments, the polypeptide according to the invention further comprises one or more substitution(s) at any one or more of amino acid positions: 114 and 166, the position(s) being determined as the corresponding position of *B. subtilis* amino acid sequence shown as SEQ ID No. 1.

In some embodiments, the polypeptide according to the invention comprises substitution(s) in at least at four of the following amino acid positions: 13, 99, 104, 113, 114, 122, 154, 159, 166, and 175, the position(s) being determined as the corresponding position of *B. subtilis* amino acid sequence shown as SEQ ID No. 1.

In some embodiments, the polypeptide according to the invention comprises substitution(s) at the amino acid positions: 13, 99, 104, 113, 114, 122, 154, 159 and 175, the position(s) being determined as the corresponding position of *B. subtilis* amino acid sequence shown as SEQ ID No. 1.

In some embodiments, the polypeptide according to the invention comprises substitution(s) at the amino acid positions: 13, 99, 104, 113, 122, 154, 159, 166 and 175, the position(s) being determined as the corresponding position of *B. subtilis* amino acid sequence shown as SEQ ID No. 1.

In some embodiments, the polypeptide according to the invention comprises substitution(s) at the amino acid positions: 13, 99, 104, 113, 122, 154, 159, and 175, the position(s) being determined as the corresponding position of *B. subtilis* amino acid sequence shown as SEQ ID No. 1.

In some embodiments, the polypeptide according to the invention comprises one or more amino acid substitutions selected from the group consisting of: 13Y, 99Y, 104W, 110A, 113D, 114D, 114F, 122F, 154R, 159D, 166F, 175K, and 175L, the position(s) being determined as the corresponding position of *B. subtilis* amino acid sequence shown as SEQ ID No. 1.

In some embodiments, the polypeptide according to the invention has at least five, six, seven, eight, nine or ten amino acid substitutions compared to the sequence selected among SEQ ID No. 1-22 with which it has the highest identity.

In some embodiments, the polypeptide according to the invention has at least nine or ten amino acid substitutions.

In some embodiments, the polypeptide according to the invention comprises one or more amino acid substitutions selected from the group consisting of:
a. D11F, R122D and T110A;
b. D11F, R122D, T110A and Y113A;
c. G13Y, T110A, Y113D, R122D and Q175L;
d. G13Y, T110A, Y113D, R122F and Q175L;
e. G13Y, G34K, T110A, Y113D, R122D and Q175L;
f. G13Y, K99Y, T104W, T110A, Y113D, N114D, R122F, K154R, N159D and Q175K;
g. G13Y, K99Y, T104W, T110A, Y113D, R122F, K154R, N159D, Q175 and V81I;
h. G13Y, K99Y, T104W, T110A, Y113D, R122F, K154R, N159D, Y166F and Q175L;
i. G13Y, T110A, Y113D, R122D, K154R, N159D and Q175L;
j. G13Y, K99Y, T104W, T110A, Y113D, R122F, K154R, N159D and Q175L;
k. G13Y, T110A, Y113D, R122D, S162E and Q175L;
l. G13Y, T110A, Y113D, R122D, S162D and Q175L;
m. G13Y, T110A, Y113D, R122D, W164F and Q175L;
n. G13Y, K99Y, T104W, T110A, Y113D, N114D, R122F, K154R, N159D and Q175L;
o. G13Y, K99Y, T104W, T110A, Y113D, N114Y, R122F, K154R, N159D and Q175L;
p. G13Y, K99Y, T104W, T110A, Y113D, N114F, R122F, K154R, N159D and Q175L;
q. G13Y, K99Y, T104W, T110A, Y113D, I118V, R122F, K154R, N159D and Q175L;
r. G13Y, K99Y, T104W, T110A, Y113D, N114Y, R122F, K154R, N159D and Q175K;
s. G13Y, K99Y, T104W, T110A, Y113D, N114D, R122F, K154R, N159D and Q175K;
t. G13Y, I77L, K99Y, T104W, T110A, Y113D, R122F, K154R, N159D and Q175L;
u. G13Y, I77M, K99Y, T104W, T110A, Y113D, R122F, K154R, N159D and Q175L;
v. G13Y, I77S, K99Y, T104W, T110A, Y113D, R122F, K154R, N159D and Q175L;
w. G13Y, I77V, K99Y, T104W, T110A, Y113D, R122F, K154R, N159D and Q175L;
x. G13Y, I77Y, K99Y, T104W, T110A, Y113D, R122F, K154R, N159D and Q175L
y. G13Y, K99Y, T104W, T110A, Y113D, R122F, N141Q, K154R, N159D, Q175L;
z. G13Y, N54Q, K99Y, T104W, T110A, Y113D, R122F, N141Q, K154R, N159D, Q175;
aa. G13Y, N54W, K99Y, T104W, T110A, Y113D, R122F, 141Q, K154R, N159D, 175L;
bb. G13Y, N54Q, K99Y, T104W, T110A, Y113D, N114F, R122F, K154R, N159D, Q175L;
cc. G13Y, K99Y, T104W, T110A, Y113D, N114F, R122F, 141Q, K154R, N159D, Q175L; and
dd. G13Y, 54Q, K99Y, T104W, T110A, Y113D, N114F, R122F, 141Q, K154R, N159D, Q175L;
the position(s) being determined as the corresponding position of *B. subtilis* amino acid sequence shown as SEQ ID No. 1.

In some embodiments, the polypeptide according to the invention comprises one or more amino acid substitutions selected from the group consisting of:
a. G13Y, K99Y, T104W, T110A, Y113D, N114D, R122F, K154R, N159D and Q175K;
b. G13Y, K99Y, T104W, T110A, Y113D, R122F, K154R, N159D, Y166F and Q175L;
c. G13Y, K99Y, T104W, T110A, Y113D, R122F, K154R, N159D and Q175L;
d. G13Y, K99Y, T104W, T110A, Y113D, N114D, R122F, K154R, N159D and Q175L;
e. G13Y, K99Y, T104W, T110A, Y113D, N114F, R122F, K154R, N159D and Q175L;
the position(s) being determined as the corresponding position of *B. subtilis* amino acid sequence shown as SEQ ID No. 1.

In some embodiments, the polypeptide according to the invention has bran solubilisation activity.

In some embodiments, the polypeptide according to the invention is in isolated form.

The term "isolated" as used herein means that the polypeptide is at least substantially free from at least one other component with which the sequence is naturally associated in nature.

In some embodiments according to the invention the amino acid modification in position 110 is not T110D.

In some embodiments the polypeptide having xylanase activity does not have an aspartic acid in position 110.

In some embodiments, the polypeptide according to the invention has improved xylanase activity compared to the *B. subtilis* amino acid sequence shown as SEQ ID No. 1 as measured in a xylanase activity assay.

In some embodiments, the polypeptide according to the invention has improved xylanase activity as a result of the modification in position 110.

In some embodiments, the polypeptide according to the invention has improved bran solubilisation activity compared to the *B. subtilis* amino acid sequence shown as SEQ ID No. 1 as measured in a bran solubilisation activity assay.

In some embodiments, the polypeptide according to the invention has improved bran solubilisation activity as a result of the modification in position 110.

In some embodiments, the polypeptide according to the invention has reduced sensitivity to a xylanase inhibitor.

In some embodiments, the polypeptide according to the invention has an amino acid sequence comprising modifications at positions selected from the list consisting of:

a) 13/110/113/122/154/159/175;
b) 13/99/104/110/113/122/154/159/166/175;
c) 13/99/104/110/113/114/122/154/159/175;
d) 13/110/113/122/175;
e) 13/99/104/110/113/122/154/159/175;
f) 13/99/104/110/113/122/154/159/175;
g) 13/99/104/110/113/114/122/154/159/175;
h) 13/99/104/110/113/114/122/154/159/175;
i) 13/99/104/110/113/114/122/154/159/175;
j) 13/99/104/110/113/114/122/154/159/175;
k) 13/77/99/104/110/113/122/154/159/175;
l) 13/81/99/104/110/113/122/154/159/175;
m) 13/110/113/122/164/175;
n) 13/110/113/122/162/175;
o) 13/110/113/122/175;
p) 11/122/110/113;
q) 13/77/99/104/110/113/122/154/159/175;
r) 11/122/110;
s) 13/34/110/113/122/175;
t) 13/77/99/104/110/113/122/154/159/175;
u) 13/77/99/104/110/113/122/154/159/175;
v) 13/99/104/110/113/118/122/154/159/175;
w) 13/110/113/122/162/175;
x) 13/77/99/104/110/113/122/154/159/175;
y) 13/99/104/110/113/122/141/154/159/175;
z) 13/54/99/104/110/113/122/141/154/159/175;
aa) 13/54/99/104/110/113/122/141/154/159/175;
bb) 13/54/99/104/110/113/114/122/154/159/175;
cc) 13/99/104/110/113/114/122/141/154/159/175; and
dd) 13/54/99/104/110/113/114/122/141/154/159/175;

the position(s) being determined as the corresponding position of *subtilis* amino acid sequence shown as SEQ ID No. 1.

In some embodiments, the polypeptide according to the invention has an amino acid sequence comprising amino acid substitutions selected from the list consisting of:

a) 13Y/110A/113D/122D/154R/159D/175L;
b) 13Y/99Y/104W/110A/113D/122F/154R/159D/166F/175L;
c) 13Y/99Y/104W/110A/113D/114F/122F/154R/159D/175L;
d) 13Y/110A/113D/122F/175L;
e) 13Y/99Y/104W/110A/113D/122F/154R/159D/175L;
f) 13Y/99Y/104W/110A/113D/122F/154R/159D/175K;
g) 13Y/99Y/104W/110A/113D/114D/122F/154R/159D/175K;
h) 13Y/99Y/104W/110A/113D/114Y/122F/154R/159D/175L;
i) 13Y/99Y/104W/110A/113D/114D/122F/154R/159D/175L;
j) 13Y/99Y/104W/110A/113D/114Y/122F/154R/159D/175K;
k) 13Y/77L/99Y/104W/110A/113D/122F/154R/159D/175L;
l) 13Y/81I/99Y/104W/110A/113D/122F/154R/159D/175L;
m) 13Y/110A/113D/122D/164F/175L;
n) 13Y/110A/113D/122D/162D/175L;
o) 13Y/110A/113D/122D122D/175L;
p) 11F/122D/110A/113A;
q) 13Y/77Y/99Y/104W/110A/113D/122F/154R/159D/175L;
r) 11F/122D/110A;
s) 13Y/34K/110A/113D/122D122D/175L;
t) 13Y/77V/99Y/104W/110A/113D/122F/154R/159D/175L;
u) 13Y/77M/99Y/104W/110A/113D/122F/154R/159D/175L;
v) 13Y/99Y/104W/110A/113D/118V/122F/154R/159D/175L;
w) 13Y/110A/113D/122D122D/162E/175L;
x) 13Y/77S/99Y/104W/110A/113D/122F/154R/159D/175L;
y) 13Y/99Y/104W/110A/113D/122F/141Q/154R/159D/175L;
z) 13Y/54Q/99Y/104W/110A/113D/122F/141Q/154R/159D/175L;
aa) 13Y/54W/99Y/104W/110A/113D/122F/141Q/154R/159D/175L;
bb) 13Y/54Q/99Y/104W/110A/113D/114F/122F/154R/159D/175L;
cc) 13Y/99Y/104W/110A/113D/114F/122F/141Q/154R/159D/175L; and
dd) 13Y/54Q/99Y/104W/110A/113D/114F/122F/141Q/154R/159D/175L;

the position(s) being determined as the corresponding position of *subtilis* amino acid sequence shown as SEQ ID No. 1.

In some embodiments, the polypeptide according to the invention has an amino acid sequence of SEQ ID No. 1 comprising amino acid substitutions selected from the list consisting of a) G13Y/T110A/Y113D/R122D/K154R/N159D/Q175L;
b) G13Y/K99Y/T104W/T110A/Y113D/R122F/K154R/N159D/Y166F/Q175L;
c) G13Y/K99Y/T104W/T110A/Y113D/N114F/R122F/K154R/N159D/Q175L;
d) G13Y/T110A/Y113D/R122F/Q175L;
e) G13Y/K99Y/T104W/T110A/Y113D/R122F/K154R/N159D/Q175L;
f) G13Y/K99Y/T104W/T110A/Y113D/R122F/K154R/N159D/Q175K;
g) G13Y/K99Y/T104W/T110A/Y113D/N114D/R122F/K154R/N159D/Q175K;
h) G13Y/K99Y/T104W/T110A/Y113D/N114Y/R122F/K154R/N159D/Q175L;
i) G13Y/K99Y/T104W/T110A/Y113D/N114D/R122F/K154R/N159D/Q175L;
j) G13Y/K99Y/T104W/T110A/Y113D/N114Y/R122F/K154R/N159D/Q175K;
k) G13Y/I77L/K99Y/T104W/T110A/Y113D/R122F/K154R/N159D/Q175L;
l) G13Y/V81I/K99Y/T104W/T110A/Y113D/R122F/K154R/N159D/Q175L;
m) G13Y/T110A/Y113D/R122D/W164F/Q175L;
n) G13Y/T110A/Y113D/R122D/S162D/Q175L;
o) G13Y/T110A/Y113D/R122D/Q175L;
p) D11F/R122D/T110A/Y113A;
q) G13Y/I77Y/K99Y/T104W/T110A/Y113D/R122F/K154R/N159D/Q175L;

r) D11F/R122D/T110A;
s) G13Y/G34K/T110A/Y113D/R122D/Q175L;
t) G13Y/I77V/K99Y/T104W/T110A/Y113D/R122F/K154R/N159D/Q175L;
u) G13Y/I77M/K99Y/T104W/T110A/Y113D/R122F/K154R/N159D/Q175L;
v) G13Y/K99Y/T104W/T110A/Y113D/I118V/R122F/K154R/N159D/Q175L;
w) G13Y/T110A/Y113D/R122D/S162E/Q175L; and
x) G13Y/I77S/K99Y/T104W/T110A/Y113D/R122F/K154R/N159D/Q175L
y) G13Y/K99Y/T104W/T110A/Y113D/R122F/N141Q/K154R/N159D/Q175L;
z) G13Y/N54Q/K99Y/T104W/T110A/Y113D/R122F/N141Q/K154R/N159D/Q1 75L;
aa) G13Y/N54W/K99Y/T104W/T110A/Y113D/R122F/141Q/K154R/N159D/17 5L.
bb) G13Y/N54Q/K99Y/T104W/T110A/Y113D/N114F/R122F/K154R/N159D/Q 175L;
cc) G13Y/K99Y/T104W/T110A/Y113D/N114F/R122F/141Q/K154R/N159D/Q17 5L; and
dd) G13Y/54Q/K99Y/T104W/T110A/Y113D/N114F/R122F/141Q/K154R/N159 D/Q175L.

In some embodiments, the polypeptide according to the invention has an amino acid sequence, which consists of amino acid substitutions selected from the list consisting of:
a) 13Y/110A/113D/122D/154R/159D/175L;
b) 13Y/99Y/104W/110A/113D/122F/154R/159D/166F/175L; c) 13Y/99Y/104W/110A/113D/114F/122F/154R/159D/175L;
d) 13Y/110A/113D/122F/175L;
e) 13Y/99Y/104W/110A/113D/122F/154R/159D/175L;
f) 13Y/99Y/104W/110A/113D/122F/154R/159D/175K;
g) 13Y/99Y/104W/110A/113D/114D/122F/154R/159D/175K;
h) 13Y/99Y/104W/110A/113D/114Y/122F/154R/159D/175L;
i) 13Y/99Y/104W/110A/113D/114D/122F/154R/159D/175L;
j) 13Y/99Y/104W/110A/113D/114Y/122F/154R/159D/175K;
k) 13Y/77L/99Y/104W/110A/113D/122F/154R/159D/175L;
l) 13Y/81I/99Y/104W/110A/113D/122F/154R/159D/175L;
m) 13Y/110A/113D/122D/164F/175L;
n) 13Y/110A/113D/122D/162D/175L;
o) 13Y/110A/113D/122D/175L;
p) 11F/122D/110A/113A;
q) 13Y/77Y/99Y/104W/110A/113D/122F/154R/159D/175L;
r) 11F/122D/110A;
s) 13Y/34K/110A/113D/122D122D/175L;
t) 13Y/77V/99Y/104W/110A/113D/122F/154R/159D/175L;
u) 13Y/77M/99Y/104W/110A/113D/122F/154R/159D/175L;
v) 13Y/99Y/104W/110A/113D/118V/122F/154R/159D/175L;
w) 13Y/110A/113D/122D122D/162E/175L;
x) 13Y/77S/99Y/104W/110A/113D/122F/154R/159D/175L;
y) 13Y/99Y/104W/110A/113D/122F/141Q/154R/159D/175L;
z) 13Y/54Q/99Y/104W/110A/113D/122F/141Q/154R/159D/175L;
aa) 13Y/54W/99Y/104W/110A/113D/122F/141Q/154R/159D/175L;
bb) 13Y/54Q/99Y/104W/110A/113D/114F/122F/154R/159D/175L;
cc) 13Y/99Y/104W/110A/113D/114F/122F/141Q/154R/159D/175L; and
dd) 13Y/54Q/99Y/104W/110A/113D/114F/122F/141Q/154R/159D/175L, the position(s) being determined as the corresponding position of *subtilis* amino acid sequence shown as SEQ ID No. 1.

In some embodiments, the polypeptide according to the invention has an amino acid sequence of SEQ ID No. 1, which consists of amino acid substitutions selected from the list consisting of
a) G13Y/T110A/Y113D/R122D/K154R/N159D/Q175L;
b) G13Y/K99Y/T104W/T110A/Y113D/R122F/K154R/N159D/Y166F/Q175L;
c) G13Y/K99Y/T104W/T110A/Y113D/N114F/R122F/K154R/N159D/Q175L;
d) G13Y/T110A/Y113D/R122F/Q175L;
e) G13Y/K99Y/T104W/T110A/Y113D/R122F/K154R/N159D/Q175L;
f) G13Y/K99Y/T104W/T110A/Y113D/R122F/K154R/N159D/Q175K;
g) G13Y/K99Y/T104W/T110A/Y113D/N114D/R122F/K154R/N159D/Q175K;
h) G13Y/K99Y/T104W/T110A/Y113D/N114Y/R122F/K154R/N159D/Q175L;
i) G13Y/K99Y/T104W/T110A/Y113D/N114D/R122F/K154R/N159D/Q175L;
j) G13Y/K99Y/T104W/T110A/Y113D/N114Y/R122F/K154R/N159D/Q175K;
k) G13Y/I77L/K99Y/T104W/T110A/Y113D/R122F/K154R/N159D/Q175L;
l) G13Y/V81I/K99Y/T104W/T110A/Y113D/R122F/K154R/N159D/Q175L;
m) G13Y/T110A/Y113D/R122D/W164F/Q175L;
n) G13Y/T110A/Y113D/R122D/S162D/Q175L;
o) G13Y/T110A/Y113D/R122D/Q175L;
p) D11F/R122D/T110A/Y113A;
q) G13Y/I77Y/K99Y/T104W/T110A/Y113D/R122F/K154R/N159D/Q175L;
r) D11F/R122D/T110A;
s) G13Y/G34K/T110A/Y113D/R122D/Q175L;
t) G13Y/I77V/K99Y/T104W/T110A/Y113D/R122F/K154R/N159D/Q175L;
u) G13Y/I77M/K99Y/T104W/T110A/Y113D/R122F/K154R/N159D/Q175L;
v) G13Y/K99Y/T104W/T110A/Y113D/I118V/R122F/K154R/N159D/Q175L;
w) G13Y/T110A/Y113D/R122D/S162E/Q175L; and
x) G13Y/I77S/K99Y/T104W/T110A/Y113D/R122F/K154R/N159D/Q175L
y) G13Y/K99Y/T104W/T110A/Y113D/R122F/N141Q/K154R/N159D/Q175L;
z) G13Y/N54Q/K99Y/T104W/T110A/Y113D/R122F/N141Q/K154R/N159D/Q1 75L;
aa) G13Y/N54W/K99Y/T104W/T110A/Y113D/R122F/141Q/K154R/N159D/175 L;
bb) G13Y/N54Q/K99Y/T104W/T110A/Y113D/N114F/R122F/K154R/N159D/Q1 75L;
cc) G13Y/K99Y/T104W/T110A/Y113D/N114F/R122F/141Q/K154R/N159D/Q17 5L; and
dd) G13Y/54Q/K99Y/T104W/T110A/Y113D/N114F/R122F/141Q/K154R/N159D/Q175L.

In some embodiments, the polypeptide according to the invention is not SEQ ID No. 25.

In some embodiments, the polypeptide according to the invention does not have a sequence selected from the list consisting of:
SEQ ID No. 57 of International Patent Application WO0238746;
SEQ ID No. 62 of International Patent Application WO0238746;
SEQ ID No. 59 of International Patent Application WO0238746;
SEQ ID No. 53 of International Patent Application WO0238746;
SEQ ID No. 65 of International Patent Application WO0238746;
SEQ ID No. 56 of International Patent Application WO0238746;
SEQ ID No. 64 of International Patent Application WO0238746:
SEQ ID No. 52 of International Patent Application WO0238746;
SEQ ID No. 63 of International Patent Application WO0238746;
SEQ ID No. 61 of International Patent Application WO0238746;
SEQ ID No. 60 of International Patent Application WO0238746;
SEQ ID No. 58 of International Patent Application WO0238746;
SEQ ID No. 55 of International Patent Application WO0238746;
SEQ ID No. 12 of International Patent Application WO0238746;
SEQ ID No. 11 of International Patent Application WO0238746;
SEQ ID No. 21 of International Patent Application WO0068396; and
SEQ ID No. 22 of International Patent Application WO0068396.

In some embodiments of the present invention, the amino acid sequence is used for large scale applications.

Preferably the amino acid sequence is produced in a quantity of from 1 g per liter to about 100 g per liter of the total cell culture volume after cultivation of the host organism.

The present invention also relates to a composition comprising amino acid sequences and/or nucleotide sequences encoding a xylanase as described herein.

The composition of the present invention can lead to improved aroma, flavour, mildness, consistency, texture, body, mouth feel, firmness, viscosity, gel fracture, structure and/or organoleptic properties and nutrition of products for consumption containing said composition. Furthermore, the composition of the present invention can also be used in combination with other components of products for consumption to deliver said improvements.

Although it is preferred that the composition of the present invention is used to improve the aroma, flavour, mildness, consistency, texture, body, mouth feel, firmness, viscosity, gel fracture, structure, smoothness of the surface and/or organoleptic properties and nutrition of products for consumption containing said composition—the present invention also covers using the composition of the present invention as a component of pharmaceutical combinations with other components to deliver medical or physiological benefit to the consumer.

Accordingly, the composition of the present invention may be used in combination with other components.

Examples of other components include one or more of: thickeners, gelling agents, emulsifiers, binders, crystal modifiers, sweetners (including artificial sweeteners), rheology modifiers, stabilisers, anti-oxidants, dyes, enzymes, carriers, vehicles, excipients, diluents, lubricating agents, flavouring agents, colouring matter, suspending agents, disintegrants, granulation binders etc. These other components may be natural. These other components may be prepared by use of chemical and/or enzymatic techniques.

As used herein the term "thickener or gelling agent" as used herein refers to a product that prevents separation by slowing or preventing the movement of particles, either droplets of immiscible liquids, air or insoluble solids. Thickening occurs when individual hydrated molecules cause an increase in viscosity, slowing the separation. Gelation occurs when the hydrated molecules link to form a three-dimensional network that traps the particles, thereby immobilizing them.

The term "stabiliser" as used here is defined as an ingredient or combination of ingredients that keeps a product (e.g. a food product) from changing over time.

The term "emulsifier" as used herein refers to an ingredient (e.g. a food product ingredient) that prevents the separation of emulsions. Emulsions are two immiscible substances, one present in droplet form, contained within the other. Emulsions can consist of oil-in-water, where the droplet or dispersed phase is oil and the continuous phase is water; or water-in-oil, where the water becomes the dispersed phase and the continuous phase is oil. Foams, which are gas-in-liquid, and suspensions, which are solid-in-liquid, can also be stabilised through the use of emulsifiers. Aeration can occur in a three phase system where air is entrapped by liquid oil then stabilised by agglomerated fat crystals stabilised with an emulsifier. Emulsifiers have a polar group with an affinity for water (hydrophilic) and a non-polar group which is attracted to oil (lipophilic). They are absorbed at the interfaces of the two substances, providing an interfacial film acting to stabilise the emulsion. The hydrophilic/lipophilic properties of emulsifiers are affected by the structure of the molecule. These properties are identified by the hydrophilic/lipophilic balance (HLB) value. Low HLB values indicate greater lipophilic tendencies which are used to stabilise water-in-oil emulsions. High HLB values are assigned to hydrophilic emulsifiers, typically used in oil-in-water emulsions. These values are derived from simple systems. Because foods often contain other ingredients that affect the emulsification properties, the HLB values may not always be a reliable guide for emulsifier selection.

As used herein the term "binder" refers to an ingredient (e.g. a food ingredient) that binds the product together through a physical or chemical reaction. During "elation" for instance, water is absorbed, providing a binding effect. However, binders can absorb other liquids, such as oils, holding them within the product. In the context of the present invention binders would typically be used in solid or low-moisture products for instance baking products: pastries, doughnuts, bread and others.

The term "crystal modifier" as used herein refers to an ingredient (e.g. a food ingredient) that affects the crystallisation of either fat or water. Stabilisation of ice crystals is important for two reasons. The first is directly related to the product stability from a separation standpoint. The more freeze/thaw cycles a product encounters, the larger the ice crystals become. These large crystals can break down product structure, either naturally occurring, as in the case of cell walls, or that which is created by "elation". Because the water is no longer held in place, the product may exhibit syneresis, or weeping, after thawing.

Secondly, in the case of a product which is consumed frozen, these large crystals result in an undesirable, gritty mouth feel.

"Carriers" or "vehicles" mean materials suitable for compound administration and include any such material known in the art such as, for example, any liquid, gel, solvent, liquid diluent, solubilizer, or the like, which is non-toxic and which does not interact with any components of the composition in a deleterious manner.

Examples of nutritionally acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Examples of excipients include one or more of: microcrystalline cellulose and other celluloses, lactose, sodium citrate, calcium carbonate, dibasic calcium phosphate, glycine, starch, milk sugar and high molecular weight polyethylene glycols.

Examples of disintegrants include one or more of: starch (preferably corn, potato or tapioca starch), sodium starch glycollate, croscarmellose sodium and certain complex silicates.

Examples of granulation binders include one or more of: polyvinylpyrrolidone, hydroxypropylmethylcellulose (HPMC), hydroxypropylcellulose (HPC), sucrose, maltose, gelatin and acacia.

Examples of lubricating agents include one or more of: magnesium stearate, stearic acid, glyceryl behenate and talc.

Examples of diluents include one or more of: water, ethanol, propylene glycol and glycerin, and combinations thereof.

The other components may be used simultaneously (e.g when they are in admixture together or even when they are delivered by different routes) or sequentially (e.g they may be delivered by different routes).

As used herein the term "component suitable for animal or human consumption" means a compound which is or can be added to the composition of the present invention as a supplement which may be of nutritional benefit, a fibre substitute or have a generally beneficial effect to the consumer. The ingredients can be used in a wide variety of products that require gelling, texturising, stabilising, suspending, film-forming and structuring, retention of juiciness, without adding unnecessary viscosity. Preferably, the ingredients will be able to improve the shelf live and stability of the viable culture.

By way of example, the components may be prebiotics such as alginate, xanthan, pectin, locust bean gum (LBG), inulin, guar gum, galacto-oligosaccharide (GOS), fructo-oligosaccharide (FOS), lactosucrose, soybean oligosaccharides, palatinose, isomalto-oligosaccharides, gluco-oligosaccharides and xylo-oligosaccharides.

The composition of the present invention may be used as—or in the preparation of—a food. Here, the term "food" is used in a broad sense—and covers food for humans as well as food for animals (i.e. a feed). In a preferred aspect, the food is for human consumption.

The food may be in the form of a solution or as a solid—depending on the use and/or the mode of application and/or the mode of administration.

When used as—or in the preparation of—a food—such as functional food—the composition of the present invention may be used in conjunction with one or more of: a nutritionally acceptable carrier, a nutritionally acceptable diluent, a nutritionally acceptable excipient, a nutritionally acceptable adjuvant, a nutritionally active ingredient.

The composition of the present invention may be used as a food ingredient.

As used herein the term "food ingredient" includes a formulation which is or can be added to functional foods or foodstuffs as a nutritional supplement and/or fiber supplement. The term food ingredient as used here also refers to formulations which can be used at low levels in a wide variety of products that require gelling, texturising, stabilising, suspending, film-forming and structuring, retention of juiciness and improved mouthfeel, without adding viscosity.

The food ingredient may be in the from of a solution or as a solid—depending on the use and/or the mode of application and/or the mode of administration.

The composition of the present invention may be—or may be added to—food supplements.

The composition of the present invention may be—or may be added to—functional foods.

As used herein, the term "functional food" means food which is capable of providing not only a nutritional effect and/or a taste satisfaction, but is also capable of delivering a further beneficial effect to consumer.

Accordingly, functional foods are ordinary foods that have components or ingredients (such as those described herein) incorporated into them that impart to the food a specific functional—e.g. medical or physiological benefit—other than a purely nutritional effect.

Although there is no legal definition of a functional food, most of the parties with an interest in this area agree that they are foods marketed as having specific health effects.

Some functional foods are nutraceuticals. Here, the term "nutraceutical" means a food which is capable of providing not only a nutritional effect and/or a taste satisfaction, but is also capable of delivering a therapeutic (or other beneficial) effect to the consumer. Nutraceuticals cross the traditional dividing lines between foods and medicine.

Surveys have suggested that consumers place the most emphasis on functional food claims relating to heart disease. Preventing cancer is another aspect of nutrition which interests consumers a great deal, but interestingly this is the area that consumers feel they can exert least control over. In fact, according to the World Health Organization, at least 35% of cancer cases are diet-related. Furthermore claims relating to osteoporosis, gut health and obesity effects are also key factors that are likely to incite functional food purchase and drive market development.

The composition of the present invention can be used in the preparation of food products such as one or more of: jams, marmalades, jellies, dairy products (such as milk or cheese), meat products, poultry products, fish products and bakery products.

By way of example, the composition of the present invention can be used as ingredients to soft drinks, a fruit juice or a beverage comprising whey protein, health teas, cocoa drinks, milk drinks and lactic acid bacteria drinks, yoghurt and drinking yoghurt, cheese, ice cream, water ices and desserts, confectionery, biscuits cakes and cake mixes, snack foods, breakfast cereals, instant noodles and cup noodles, instant soups and cup soups, balanced foods and drinks, sweeteners, texture improved snack bars, fibre bars, bake stable fruit fillings, care glaze, chocolate bakery filling, cheese cake flavoured filling, fruit flavoured cake filling, cake and doughnut icing, heat stable bakery filling, instant bakery filling creams, filing for cookies, ready-to-use bakery filling, reduced calorie filling, adult nutritional beverage, acidified soy/juice beverage, aseptic/retorted chocolate drink, bar mixes, beverage powders, calcium fortified soy/plain and chocolate milk, calcium fortified coffee beverage.

A composition according to the present invention can further be used as an ingredient in food products such as American cheese sauce, anti-caking agent for grated & shredded cheese, chip dip, cream cheese, dry blended whip topping fat free sour cream, freeze/thaw dairy whipping cream, freeze/thaw stable whipped tipping, low fat & lite natural cheddar cheese, low fat Swiss style yoghurt, aerated frozen desserts, and novelty bars, hard pack ice cream, label friendly, improved economics & indulgence of hard pack ice cream, low fat ice cream: soft serve, barbecue sauce, cheese dip sauce, cottage cheese dressing, dry mix Alfredo sauce, mix cheese sauce, dry mix tomato sauce and others.

For certain aspects, preferably the foodstuff is a beverage.

For certain aspects, preferably the foodstuff is a bakery product—such as bread, Danish pastry, biscuits or cookies.

The present invention also provides a method of preparing a food or a food ingredient, the method comprising xylanase produced by the process of the present invention or the composition according to the present invention with another food ingredient. The method for preparing or a food ingredient is also another aspect of the present invention.

In a general sense, a polypeptide having xylanase activity of the invention may be used to solubilise and/or degrade insoluble plant cell wall material containing arabinoxylan, alter, for example reduce, the viscosity derived from the presence of hemicellulose or arabinoxylan in a solution or system comprising plant cell wall material. Typically said plant cell wall materials will comprise one or more xylanase inhibitors.

Specifically, a polypeptide having xylanase activity of the invention may be used in processing plant materials for use as foodstuffs, such as animal feed, in starch production, in baking, in production of Bio-ethanol from cellulosic material and in the processing of wood pulp to make paper.

A polypeptide having xylanase activity of the invention may be used to process plant materials such as cereals that are used in foodstuffs including animal feed. As used herein, the term "cereal" means any kind of grain used for food and/or any grass producing this grain such as but not limited to any one of wheat, milled wheat, barley, maize, sorghum, rye, oats, triticale and rice or combinations thereof. In one preferred embodiment, the cereal is a wheat cereal.

The xylan in the food and/or feed supplement is modified by contacting the xylan with the polypeptide having xylanase activity of the present invention.

As used herein, the term "contacting" includes but is not limited to spraying, coating, impregnating or layering the food and/or feed supplement with the polypeptide having xylanase activity of the present invention.

In one embodiment, the food and/or feed supplement of the present invention may be prepared by mixing the polypeptide having xylanase activity directly with a food and/or feed supplement. By way of example, the polypeptide having xylanase activity may be contacted (for example, by spraying) onto a cereal-based food and/or feed supplement such as milled wheat, maize or soya flour.

It is also possible to incorporate the polypeptide having xylanase activity it into a second (and different) food and/or feed or drinking water which is then added to the food and/or feed supplement of the present invention. Accordingly, it is not essential that the polypeptide having xylanase activity provided by the present invention is incorporated into the cereal-based food and/or feed supplement itself, although such incorporation forms a particularly preferred aspect of the present invention.

In one embodiment of the present invention, the food and/or feed supplement may be combined with other food and/or feed components to produce a cereal-based food and/or feed. Such other food and/or feed components may include one or more other (preferably thermostable) enzyme supplements, vitamin food and/or feed supplements, mineral food and/or feed supplements and amino acid food and/or feed supplements. The resulting (combined) food and/or feed supplement comprising possibly several different types of compounds can then be mixed in an appropriate amount with the other food and/or feed components such as cereal and protein supplements to form a human food and/or an animal feed.

In one preferred embodiment, the food and/or feed supplement of the present invention can be prepared by mixing different enzymes having the appropriate activities to produce an enzyme mix. By way of example, a cereal-based food and/or feed supplement formed from e.g. milled wheat or maize may be contacted (e.g. by spraying) either simultaneously or sequentially with the xylanase enzyme and other enzymes having appropriate activities. These enzymes may include but are not limited to any one or more of an amylase, a glucoamylase, a mannanase, a galactosidase, a phytase, a lipase, a phospholipase, a galactolipase, a glucanase, an-arabinofuranosidase, a ferulyol esterase, a pectinase, a protease, a glucose oxidase, a hexose oxidase and a xylanase. Enzymes having the desired activities may for instance be mixed with the xylanase of the present invention either before contacting these enzymes with a cereal-based food and/or feed supplement or alternatively such enzymes may be contacted simultaneously or sequentially on such a cereal based supplement. The food and/or feed supplement is then in turn mixed with a cereal-based food and/or feed to prepare the final food and/or feed. It is also possible to formulate the food and/or feed supplement as a solution of the individual enzyme activities and then mix this solution with a food and/or feed material prior to processing the food and/or feed supplement into pellets or as a mash.

The present invention provides the use of a polypeptide having xylanase activity of the invention in a process for preparing a foodstuff. Typical bakery (baked) products in accordance with the present invention include bread—such as loaves, rolls, buns, pizza bases etc.—pretzels, tortillas, cakes, cookies, biscuits, crackers etc. The preparation of foodstuffs such as bakery products is well know in the art. Dough production, for example, is described in example 4. The use of a polypeptide having xylanase activity of the invention to alter the baking performance is described in example 4.

A polypeptide having xylanase activity of the invention may also be used in starch production from plant materials derived from cereals and tubers, such as potatoes.

A polypeptide having xylanase activity of the invention may also be used in processing wood pulp, for example in the preparation of paper.

Processing of cellulosic material for bio-ethanol production

A polypeptide having xylanase activity of the invention may also be used in the hydrolysis of cellulosic plant material for production of sugars fermentable to bio-ethanol.

In some particular embodiments the polypeptide having xylanase activity according to the invention has an optimal xylanase activity at dough processing temperatures, such as in the range of about 20 to about 40° C. In some embodiments the polypeptide having xylanase activity according to the invention are inactivated during a baking process.

In some alternative embodiments the polypeptide having xylanase activity according to the invention has increased thermostability and/or temperature optimum as compared to the corresponding wild type enzyme to retain activity after heat treatment. Both characteristics are known to persons skilled in the art.

EXAMPLES

Example 1

Site-Directed Mutagensis of Xylanases and Expression

Specific mutants of the *Bacillus subtilis* xylanase were obtained using a construct comprising the ribosome binding site from pET24a (ctagaaataattttgtttaactttaagaaggagatatacat) fused to the wild type xylanase gene without signal sequence (atggctagcacagactactggcaa--------tggtaa) was transferred to the vector pCRBlunt (InVitrogen, Carlsbad, Calif., USA). This resulted in constitutive expression of xylanase in TOP10 cells (InVitrogen) after transformation with the constructed vector, provided that the orientation of the gene is in a "clockwise" direction. Site directed mutation in the gene was then obtained by the use of the "QuickChange" mutagenesis kit (Stratagene, La Jolla, Calif., USA) according to the manufacturers protocol. Mutants were verified by sequencing. Sufficient production of the verified mutants was obtained by growing the transformed TOP10 cells in 1 L scale.

Example 2

Bran Solubilisation Studies of Xylanase Mutants

We used wheat bran as substrate to evaluate the specific activity of the xylanase variants since this is used in commercial applications.

Bran Substrate:

By means of example, bran could be wheat bran obtained from dry milling of wheat using a lab scale Chopin CD Auto Mill (Chopin Technologies, France), using the setting and conditions provided by the supplier, for milling wheat into wheat flour and bran. The obtained bran fraction may be used as substrate in the bran solubilisation assay. In this Example wheat was used as the cereal source.

Bran Solubilisation Assay:

A suspension of wheat bran in (0.1 M)-di-sodium-hydrogen phosphate (0.2 M) buffer, pH 5.0 is prepared to an concentration of 1.33% bran (w/w). From this suspension, aliquots of 750 l are transferred into eppendorph tubes under stirring. Each substrate tube is pre-heated for 5 minutes at 40° C. Hereto, 250 µl enzyme solution is added, making the end concentration of substrate 1%. Three dilutions (in duplicate) are made from each xylanases, with increasing enzyme concentration (0.33; 1.0 and 3.0 µg xylanase/gram bran) to each time of determination (0, 30, 60 and 240 minutes). As blank, a heat denaturated solution of the xylanase is used. The reaction is terminated to the given times, by transferring the tubes to an incubator set at 95° C. Heat denaturated samples are kept at 4° C. until all enzyme reactions are terminated. When all enzyme reactions are terminated, Eppendorph tubes are centrifuged to obtain a clear supernatant. The enzymes capability to solubilise bran is expressed as $OD_{410}$ increase, determined by the increase in reducing end groups using PAHBAH reagens (Lever, 1972).

In short, reducing end groups are reacted with PAHBAH forming a colored reaction product, which can be quantified at OD $OD_{410}$.

The above bran solubilisation assay is sensitive to side activity of enzymes active on residual starch in the bran substrate.

*Bacillus subtilis* Xylanase Purification Protocol:

*E. coli* TOP10 cells having expressed the xylanase were harvested by centrifugation (20 minutes, 3500×g, 20° C.) and resuspended in 50 mM Tris, 2 mM EDTA, pH 7.4. Cells were opened by addition of 1 mg/ml lysozyme (ICN Biomedicals, Costa Mesa, Calif., US, cat. No. 100831), stirring of the slurry for 2 hours at ambient temperature, freezing and thawing followed by sonication. pH was adjusted to 4.0 using 1M HCl followed by centrifugation (20 minutes, 3500×g, 20° C.). The supernatant containing the xylanase was desalted using disposable PD-10 desalting columns (Amersham Bioscience, Sweden) equilibrated in and eluted with 50 mM sodium acetate, pH 4.5. The desalted sample was loaded onto a 10 ml SOURCE 15S column (Amersham Bioscience, Sweden) pre-equilibrated with 50 mM sodium acetate, pH 4.5. The column was then washed with equilibration buffer and eluted with a linear NaCl gradient (50 mM sodium acetate, 0-0.35M NaCl, pH 4.5). Fractions containing xylanase activity were pooled and used for further analysis.

Similar protocols may be adapted to non-*Bacillus subtilis* XynA derived xylanase variants having a pI significantly different from *Bacillus subtilis* XynA

TABLE 1

Xylanases bran solubilising activity expressed as, maximum optical density, slope index of xylanase mutants, relative optical density and slope compared to the xylanase BS1 (the *Bacillus subtilis* enzyme shown as SEQ ID No. 1) and the xylanase BS3 (*Bacillus subtilis* variant shown as SEQ ID No. 23)

| Modifications made to SEQ ID No. 1 | Slope OD/hr | Maximum OD | Relative Slope to BS1 | Relative Max. OD to BS1 | Relative Slope to BS3 | Relative Max. OD to BS3 |
|---|---|---|---|---|---|---|
| None (BS1) | 0.23 | 0.69 | 100 | 100 | 140 | 140 |
| D11F/R122D (BS3) | 0.16 | 0.49 | 72 | 72 | 100 | 100 |
| D11F/R122D/T110A | 0.25 | 0.75 | 110 | 110 | 154 | 154 |
| D11F/R122D/T110A/Y113A | 0.27 | 0.80 | 117 | 117 | 163 | 163 |
| G13Y/T110A/Y113D/R122D/Q175L | 0.27 | 0.82 | 119 | 119 | 167 | 167 |
| G13Y/T110A/Y113D/R122F/Q175L | 0.37 | 1.12 | 164 | 164 | 229 | 229 |
| G13Y/G34K/T110A/Y113D/R122D/Q175L | 0.25 | 0.74 | 108 | 108 | 150 | 150 |
| G13Y/K99Y/T104W/T110A/Y113D/R122F/K154R/N159D/Q175K | 0.37 | 1.11 | 162 | 162 | 226 | 226 |

TABLE 1-continued

Xylanases bran solubilising activity expressed as, maximum optical density, slope index of xylanase mutants, relative optical density and slope compared to the xylanase BS1 (the *Bacillus subtilis* enzyme shown as SEQ ID No. 1) and the xylanase BS3 (*Bacillus subtilis* variant shown as SEQ ID No. 23)

| Modifications made to SEQ ID No. 1 | Slope OD/hr | Maximum OD | Relative Slope to BS1 | Relative Max. OD to BS1 | Relative Slope to BS3 | Relative Max. OD to BS3 |
|---|---|---|---|---|---|---|
| G13Y/K99Y/T104W/ T110A/Y113D/R122F/ K154R/N159D/ Q175/V81I | 0.29 | 0.87 | 128 | 128 | 178 | 178 |
| G13Y/K99Y/T104W/ T110A/Y113D/R122F/ K154R/N159D/Y166F/ Q175L | 0.39 | 1.18 | 172 | 172 | 241 | 241 |
| G13Y/T110A/Y113D/ R122D/K154R/N159D/ Q175L | 0.40 | 1.19 | 173 | 173 | 242 | 242 |
| G13Y/K99Y/T104W/ T110A/Y113D/R122F/ K154R/N159D/ Q175L | 0.37 | 1.11 | 162 | 162 | 226 | 226 |
| G13Y/T110A/Y113D/ R122D/S162E/Q175L | 0.18 | 0.53 | 78 | 78 | 109 | 109 |
| G13Y/T110A/Y113D/ R122D/S162D/Q175L | 0.28 | 0.83 | 121 | 121 | 169 | 169 |
| G13Y/T110A/Y113D/ R122D/W164F/Q175L | 0.28 | 0.83 | 121 | 121 | 169 | 169 |
| G13Y/K99Y/T104W/ T110A/Y113D/N114D/ R122F/K154R/ N159D/Q175L | 0.34 | 1.02 | 149 | 149 | 208 | 208 |
| G13Y/K99Y/T104W/ T110A/Y113D/N114Y/ R122F/K154R/N159D/ Q175L | 0.35 | 1.04 | 152 | 152 | 212 | 212 |
| G13Y/K99Y/T104W/ T110A/Y113D/N114F/ R122F/K154R/N159D/ Q175L | 0.38 | 1.15 | 169 | 169 | 235 | 235 |
| G13Y/K99Y/T104W/ T110A/Y113D/I118V/ R122F/K154R/N159D/ Q175L | 0.21 | 0.63 | 92 | 92 | 128 | 128 |
| G13Y/K99Y/T104W/ T110A/Y113D/N114Y/ R122F/K154R/N159D/ Q175K | 0.33 | 0.98 | 144 | 144 | 201 | 201 |
| G13Y/K99Y/T104W/ T110A/Y113D/N114D/ R122F/K154R/ N159D/Q175K | 0.35 | 1.05 | 153 | 153 | 214 | 214 |
| G13Y/I77L/K99Y/T104W/ T110A/Y113D/ R122F/K154R/N159D/ Q175L | 0.31 | 0.93 | 136 | 136 | 190 | 190 |
| G13Y/I77M/K99Y/T104W/ T110A/Y113D/ R122F/K154R/N159D/ Q175L | 0.22 | 0.67 | 98 | 98 | 137 | 137 |
| G13Y/I77V/K99Y/T104W/ T110A/Y113D/ R122F/K154R/N159D/ Q175L | 0.23 | 0.69 | 101 | 101 | 141 | 141 |
| G13Y/I77Y/K99Y/T104W/ T110A/Y113D/ R122F/K154R/N159D/ Q175L | 0.27 | 0.80 | 117 | 117 | 163 | 163 |

Example 3

Testing of Xylanase Activity and Relative Inhibition by Cereal Xylanase Inhibitors The mutants of Example 2 were tested for xylanase activity and relative sensitivity to a xylanase inhibitor by the protocols presented below and in accordance with the following teachings.

Xylanase Assay (Endo-β-1,4-Xylanase Activity)

Samples were diluted in citric acid (0.1 M)-di-sodium-hydrogen phosphate (0.2 M) buffer, pH 5.0, to obtain approx. $OD_{590}=0.7$ in this assay. Three different dilutions of the sample were pre-incubated for 5 minutes at 40° C. At time=5 minutes, 1 Xylazyme tablet (crosslinked, dyed xylan substrate, Megazyme, Bray, Ireland) was added to the enzyme solution in a reaction volume of 1 ml. At time=15 minutes the reaction was terminated by adding 10 ml of 2% TRIS/NaOH, pH 12. Blanks were prepared using 1000 μl buffer instead of enzyme solution. The reaction mixture was centrifuged (1500×g, 10 minutes, 20° C.) and the OD of the supernatant was measured at 590 nm. One xylanase unit (XU) is defined as the xylanase activity increasing $OD_{590}$ with 0.025 per minute.

Specific Activity Determination:

Optical density at 280 nm of the purified samples was measured for determining xylanase protein concentration. A theoretically calculated, specific $OD_{280}$ (Gasteiger et al., 2003) of 0.25 units/mg×ml was used for the specific activity calculation of the *Bacillus subtilis* XynA derived variants. Xylanase activity was determined as described above.

Xylanase Inhibitor Assay

100 μl inhibitor preparation (containing various concentrations of xylanase inhibitor (for quantification see Xylanase inhibitor quantification below)), 250 μl xylanase solution (containing 12 XU xylanase/ml) and 650 μl buffer (0.1 M citric acid—0.2M di-sodium hydrogen phosphate buffer, 1% BSA (Sigma-Aldrich, USA), pH 5.0) was mixed. The mixture was thermostated for 5 minutes at 40.0° C. At time=5 minutes one Xylazyme tablet (crosslinked, dyed xylan substrate, Megazyme, Bray, Ireland) was added. At time=15 minutes reaction was terminated by adding 10 ml 2% TRIS/NaOH, pH 12. The reaction mixture was centrifuged (1500×g, 10 minutes, 20° C.) and the supernatant measured at 590 nm. The xylanase inhibition was calculated as residual activity in %, compared to the blank. Blanks were prepared the same way, but substituting the inhibitor solution with water.

Xylanase Inhibitor Quantification:

1 XIU (Xylanase Inhibitor Unit) is defined as the amount of inhibitor that decreases 1 XU of the *Bacillus subtilis* XynA xylanase (Seq ID No 1) to 0.5 XU under the conditions described below.

250 μl xylanase solution containing 12 XU/ml, approx. 100 μl xylanase inhibitor solution and McIlvaine buffer, pH 5, to reach a reaction volume of 1000 μl is pre-incubated for 5 minutes at 40° C. At t=5 minutes, 1 Xylazyme tablet is added to the reaction mixture. At t=15 minutes the reaction is terminated, by addition of 10 ml 2% TRIS/NaOH, pH 12. The solution is filtered and the absorbance of the supernatant is measured at 590 nm. By choosing several different concentrations of inhibitor in the above assay, it is possible to create a plot of OD versus inhibitor concentration. Using the slope (a) and intercept (b) from this plot and the concentration of the xylanase it is possible to calculate the amount of XIU in a given inhibitor solution (equation 1).

$$XIU=((b/2)/-a)/x \quad \text{Equation 1}$$

X=Xylanase units (XU) in the assay

Inhibitor Preparation:

A crude inhibitor preparation (containing both TAXI and XIP, hereafter referred to as inhibitor preparation) was prepared from 1 kg wheat (*Triticum aestivum*) flour. The inhibitor preparation was extracted from the flour using water in a 1:3 ratio (w/w) followed by centrifugation (3500×g, 20 minutes, 4° C.). The extract was kept at 65° C. for 40 minutes, centrifuged (3500×g, 20 minutes, 4° C.) and desalted using disposable PD-10 desalting columns (Amersham Bioscience, Sweden) pre-equilibrated with 20 mM sodium phosphate buffer, pH 7. TAXI concentration in the inhibitor preparation was determined by as described above. The protocol for purification and quantification of TAXI is described elsewhere (Sibbesen and Sørensen, 2001). By mean of example only, the TAXI in the preparation could be SEQ ID No. 24 or a sequence having 90% identity thereto.

TABLE 2

Xylanase activity (XU/mg) and xylanase inhibitor sensitivity of mutants indicated as residual xylanase activity at increasing xylanase inhibitor concentrations (XIU/ml assay).

| Modifications made to SEQ ID No. 1 | Specific Activity XU/mg | % Activity @ 5.6 XIU/ml | % Activity @ 33.5 XIU/ml | % Activity @ 50 XIU/ml |
|---|---|---|---|---|
| None (BS1) | 23,000 | 29 | | |
| D11F R122D (BS3) | 8,400 | 100 | 100 | 95 |
| D11F/R122D/T110A | 14,992 | 98 | 100 | |
| D11F/R122D/T110A/Y113A | 13,362 | 99 | | |
| G13Y/T110A/Y113D/R122D/Q175L | 59,571 | | 50 | |
| G13Y/T110A/Y113D/R122F/Q175L | 53,855 | | 65 | |
| G13Y/G34K/T110A/Y113D/R122D/Q175L | 15,876 | | 97 | |
| G13Y/K99Y/T104W/T110A/Y113D/R122F/K154R/N159D/Q175K | 47,975 | | 72 | |
| G13Y/K99Y/T104W/T110A/Y113D/R122F/K154R/N159D/Q175/V81I | 41,791 | | 46 | |
| G13Y/K99Y/T104W/T110A/Y113D/R122F/K154R/N159D/Y166F/Q175L | 53,331 | | 68 | |
| G13Y/T110A/Y113D/R122D/K154R/N159D/Q175L | 54,924 | | 32 | |
| G13Y/K99Y/T104W/T110A/Y113D/R122F/K154R/N159D/Q175L | 54,811 | | 64 | |
| G13Y/T110A/Y113D/R122D/S162E/Q175L | 55,249 | | 44 | |
| G13Y/T110A/Y113D/R122D/S162D/Q175L | 52,735 | | 40 | |
| G13Y/T110A/Y113D/R122D/W164F/Q175L | 51,884 | | 29 | |
| G13Y/K99Y/T104W/T110A/Y113D/N114D/R122F/K154R/N159D/Q175L | 47,445 | | 79 | |
| G13Y/K99Y/T104W/T110A/Y113D/N114Y/R122F/K154R/N159D/Q175L | 46,263 | | 78 | |
| G13Y/K99Y/T104W/T110A/Y113D/N114F/R122F/K154R/N159D/Q175L | 42,077 | | 79 | |

TABLE 2-continued

Xylanase activity (XU/mg) and xylanase inhibitor sensitivity of mutants indicated as residual xylanase activity at increasing xylanase inhibitor concentrations (XIU/ml assay).

| Modifications made to SEQ ID No. 1 | Specific Activity XU/mg | % Activity @ 5.6 XIU/ml | % Activity @ 33.5 XIU/ml | % Activity @ 50 XIU/ml |
|---|---|---|---|---|
| G13Y/K99Y/T104W/T110A/Y113D/I118V/R122F/K154R/N159D/Q175L | 27,363 | | | 79 |
| G13Y/K99Y/T104W/T110A/Y113D/N114Y/R122F/K154R/N159D/Q175K | 35,906 | | | 84 |
| G13Y/K99Y/T104W/T110A/Y113D/N114D/R122F/K154R/N159D/Q175K | 46,939 | | | 79 |
| G13Y/I77L/K99Y/T104W/T110A/Y113D/R122F/K154R/N159D/Q175L | 48,177 | | | 75 |
| G13Y/I77M/K99Y/T104W/T110A/Y113D/R122F/K154R/N159D/Q175L | 28,412 | | | 46 |
| G13Y/I77S/K99Y/T104W/T110A/Y113D/R122F/K154R/N159D/Q175L | 12,003 | | | 20 |
| G13Y/I77V/K99Y/T104W/T110A/Y113D/R122F/K154R/N159D/Q175L | 35,907 | | | 45 |
| G13Y/I77Y/K99Y/T104W/T110A/Y113D/R122F/K154R/N159D/Q175L | 33,236 | | | 37 |

Example 4

Baking Performance of Mutants

Baking was done using a scale-down of the Danish Roll recipe (Table 3), using either wheat flour or wheat whole meal flour.

TABLE 3

Recipe used for production of bread.

| Ingredients | Mini skala ml or g |
|---|---|
| Flour | 50 |
| Dry yeast | 1 |
| Salt | 0.8 |
| Sugar | 0.8 |
| Water | 400 BU - 2% |

Note:
Water is the water absorption @ 400BU determined by Farinograph analysis of flour (i.e, 400 bakers absorbance - water added according to water absorbtion determination using a Brabrender Farinograph, Brabrender, Germany). If enzymes are added to the dough, they are added as liquid solution and by substitution of the same amount of water.

Dough Making and Baking

The flour and dry ingredients were mixed for one minute in a 50 gram Farinograph (Brabender, Duisburg, Germany), hereafter water was added and mixing was continued for another five minutes.

After mixing, four dough lumps were weighed out, each containing 10-grams of flour. These were moulded into bread using a hand moulder. Loaves were put into baking pans and placed in a sealed container (with a lid) and left to rest at room temperature for 10 minutes. Hereafter, breads were proofed at 34° C., 85% relative humidity (RH), for 45 minutes and finally baked at 230° C. for five minutes in a Bago oven (Bago-line, Fåborg, Denmark).

The breads were cooled for 20 minutes before evaluation (weighing, volume measurement, crumb and crust evaluation).

TABLE 4

Baking performance of mutants - bread volume (ml/g) and relative volume increase compared to control (no enzyme added) and BS3 (SEQ ID No. 1 with the modifications D11F and R122D) which show superior baking performance compared to the *Bacillus sub.* XynA wildtype xylanase (SEQ ID No. 1).

| Modifications made to Seq ID No 1 | Bread vol @ 0.04 mg/kg flour | Relative vol. Increase vs control, % | Relative volume increase vs. BS3, % |
|---|---|---|---|
| G13Y/G34K/T110A/Y113D/R122D/Q175L | 4.22 | 41.89 | 20 |
| G13Y/K99Y/T104W/T110A/Y113D/R122F/K154R/N159D/Q175K | 2.90 | 21.93 | 7.54 |
| G13Y/V81I/K99Y/T104W/T110A/Y113D/R122F/K154R/N159D/Q175L | 2.80 | 18.02 | 4.09 |
| G13Y/K99Y/T104W/T110A/Y113D/R122F/K154R/N159D/Y166F/Q175L | 2.82 | 18.86 | 4.83 |
| G13Y/T110A/Y113D/R122D/K154R/N159D/Q175L | 2.81 | 18.08 | 4.15 |
| G13Y/K99Y/T104W/T110A/Y113D/R122F/K154R/N159D/Q175L | 2.89 | 21.74 | 7.24 |
| G13Y/T110A/Y113D/R122D/S162E/Q175L | 2.75 | 13.55 | 1.99 |
| G13Y/T110A/Y113D/R122D/S162D/Q175L | 2.82 | 15.54 | 4.48 |
| G13Y/T110A/Y113D/R122D/W164F/Q175L | 2.78 | 14.02 | 3.10 |
| G13Y/K99Y/T104W/T110A/Y113D/N114D/R122F/K154R/N159D/Q175L | 2.81 | 16.44 | 4.11 |
| G13Y/K99Y/T104W/T110A/Y113D/N114Y/R122F/K154R/N159D/Q175L | 2.73 | 13.26 | 1.26 |
| G13Y/K99Y/T104W/T110A/Y113D/N114F/R122F/K154R/N159D/Q175L | 2.80 | 16.22 | 3.74 |
| G13Y/K99Y/T104W/T110A/Y113D/I118V/R122F/K154R/N159D/Q175L | 2.83 | 17.58 | 4.95 |
| G13Y/K99Y/T104W/T110A/Y113D/N114Y/R122F/K154R/N159D/Q175K | 2.89 | 20.65 | 7.34 |
| G13Y/K99Y/T104W/T110A/Y113D/N114D/R122F/K154R/N159D/Q175K | 2.77 | 14.73 | 2.63 |
| G13Y/I77L/K99Y/T104W/T110A/Y113D/R122F/K154R/N159D/Q175L | 2.81 | 15.08 | 4.32 |
| G13Y/I77M/K99Y/T104W/T110A/Y113D/R122F/K154R/N159D/Q175L | 2.70 | 12.43 | 0.17 |

TABLE 4-continued

Baking performance of mutants - bread volume (ml/g) and relative volume increase compared to control (no enzyme added) and BS3 (SEQ ID No. 1) with the modifications D11F and R122D) which show superior baking performance compared to the *Bacillus sub.* XynA wildtype xylanase (SEQ ID No. 1).

| Modifications made to Seq ID No 1 | Bread vol @ 0.04 mg/kg flour | Relative vol. Increase vs control, % | Relative volume increase vs. BS3, % |
|---|---|---|---|
| G13Y/I77S/K99Y/ T104W/T110A/Y113D/ R122F/K154R/N159D/ Q175L | 2.53 | 5.40 | (6.09) |
| G13Y/I77V/K99Y/ T104W/T110A/Y113D/ R122F/K154R/N159D/ Q175L | 2.60 | 8.19 | (3.63) |
| G13Y/I77Y/K99Y/ T104W/T110A/Y113D/ R122F/K154R/N159D/ Q175L | 2.73 | 13.81 | 1.38 |

Example 5

Effect of Modification to Residue 110 in the *Bacillus subtilis* XynA Xylanase (SEQ ID NO. 1) or Equivalent Position in Other Family 11 Xylanases Xylanases:

Xylanases mutated in this example are the *Bacillus subtilis* XynA wildtype xylanase (SEQ ID No. 1), a variant of the *Trichoderma reesei* Xyn2 xylanase (SEQ ID No. 2) and the *Thermomyces lanuginosus* XynA wildtype xylanase (SEQ ID No. 3).

The residue mutated is T110 in the *Bacillus subtilis* XynA wildtype xylanase (SEQ ID No. 1), the equivalent position, T120, in *Trichoderma reesei* xylanase (SEQ ID No. 2) and the equivalent position, T120, in *Thermomyces lanuginosus* XynA wildtype xylanase (SEQ ID No. 3). The following mutations were made in *Bacillus subtilis* XynA wildtype xylanase (SEQ ID No. 1): T110H, T110Y, T110S, T110R, T110F, T110Q, T110G, T110K, T110L, T110M, T110I, T110T, T110N, T110E, T110W, T110A and T110C. In both *Trichoderma reesei* xylanase (SEQ ID No. 2) and *Thermomyces lanuginosus* XynA wildtype xylanase (SEQ ID No. 3) the equivalent position, T120, was mutated. The mutations made is to the amino acid alanine.

Mutations, expression, purification and determination of specific activity of the wildtype xylanases or their variants are carried out as described in Examples 1, 2 and 3. Except for the purification of the *Trichoderma reesei* variant xylanase, the *Thermomyces lanuginosus* XynA wildtype xylanase and their T120A variant, here the purification protocol was modified to reflect their pI.

TABLE 5

Specific activity determined as XU/mg xylanase protein of the *Bacillus subtilis* XynA wildtype xylanase (SEQ ID No. 1), the *Bacillus subtilis* XynA variant xylanase (T110A), the *Trichoderma reesei* xylanase (SEQ ID No. 2), the *Trichoderma reesei* Xyn2 variant xylanase (T120A), the *Thermomyces lanuginosus* XynA wildtype xylanase (SEQ ID NO. 3) and the *Thermomyces lanuginosus* XynA variant xylanase (T120A).

| Xylanase | Specific activity, XU/mg |
|---|---|
| *Bacillus subtilis* XynA wildtype xylanase (SEQ ID No. 1) | 23,000 |
| *Bacillus subtilis* XynA variant xylanase (T110A) | 25874 |
| *Bacillus subtilis* XynA variant xylanase (T110N) | 23104 |

TABLE 5-continued

Specific activity determined as XU/mg xylanase protein of the *Bacillus subtilis* XynA wildtype xylanase (SEQ ID No. 1), the *Bacillus subtilis* XynA variant xylanase (T110A), the *Trichoderma reesei* xylanase (SEQ ID No. 2), the *Trichoderma reesei* Xyn2 variant xylanase (T120A), the *Thermomyces lanuginosus* XynA wildtype xylanase (SEQ ID NO. 3) and the *Thermomyces lanuginosus* XynA variant xylanase (T120A).

| Xylanase | Specific activity, XU/mg |
|---|---|
| *Bacillus subtilis* XynA variant xylanase (T110E) | 24782 |
| *Bacillus subtilis* XynA variant xylanase (T110W) | 25478 |
| *Bacillus subtilis* XynA variant xylanase (T110C) | 26390 |
| *Trichoderma reesei* xylanase (SEQ ID No. 2) | 17,500 |
| *Trichoderma reesei* variant xylanase (T120A) | 36797 |
| *Thermomyces lanuginosus* XynA wildtype xylanase (SEQ ID No 3) | 31,300 |
| *Thermomyces lanuginosus* XynA variant xylanase (T120A) | 36066 |

In all cases, the mutation T110A in the *Bacillus subtilis* XynA wildtype xylanase (SEQ ID No. 1) or the equivalent position (T120) in the *Trichoderma reesei* xylanase (SEQ ID No. 2) or the *Thermomyces lanuginosus* XynA wildtype xylanase (SEQ ID No 3) results in a significant increased specific activity.

In *Bacillus subtilis* XynA wildtype xylanase (SEQ ID No. 1) also the mutations T110E, T110N, T110W, and T110C results in an increased specific activity. All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

Example 6

Activity of Xylanase Variants on Water-Insoluble Substrate Versus Insoluble Substrate Xylanase variants of the BACSU_XynA and TRIR-E_Xyn2 was generated using site-directed mutagensis of xylanases and expression in *E. coli*.

Assay to determine activity on Water unextractable substrate, WU-AX act. (insoluble substrate):

Samples were diluted in citric acid (0.1 M)-di-sodium-hydrogen phosphate (0.2 M) buffer, pH 5.0, to obtain approx. $OD_{590}$=0.7 in this assay. Three different dilutions of the sample were pre-incubated for 5 minutes at 40° C. At time=5 minutes, 1 Xylazyme tablet (crosslinked, dyed xylan substrate, Megazyme, Bray, Ireland) was added to the enzyme solution in a reaction volume of 1 ml. At time=15 minutes the reaction was terminated by adding 10 ml of 2% TRIS/NaOH, pH 12. Blanks were prepared using 1000 µl buffer instead of enzyme solution. The reaction mixture was centrifuged (1500×g, 10 minutes, 20° C.) and the OD of the supernatant was measured at 590 nm. One xylanase unit (WU-AX act) is defined as the xylanase activity increasing $OD_{590}$ with 0.025 per minute.

The substrate (cross-linked and dyed arabinoxylan extracted from wheat) used in the above assay is a good approximate to the corresponding substrate in commercial applications.

The following assay was used to determine activity on Water extractable substrate, WE-AX act (soluble substrate).

The method used is a modified version of the method described by Lever (Lever, M. Analytical Biochemistry. 47, 273-279, 1972). Soluble wheat arabinoxylan (medium viscosity, obtainable from Megazyme, Bray, Ireland) was used as substrate in a buffersystem containing 50 mM NaOAc, pH 5. Substrate concentration was 0.5%. Xylanase activity was measured by quantifying the formation of reducing ends using PAHBAH reagens. The amount of reducing ends formed and hereby the xylanase activity was determined from a xylose standard curve. Here referred to as WE-AX act.

Backbones Used for Developing New Variants:

Table 6 show xylanase variants backbones used. Y5 corresponds to SEQ ID NO. 2.

| ID | Variant |
|---|---|
| #154 | BACSU_XynA-G13Y/K99Y/T104W/T110A/Y113D/R122F/K154R/N159D/Q175L |
| #160 | BACSU_XynA-G13Y/K99Y/T104W/T110A/Y113D/N114F/R122F/K154R/N159D/Q175L |
| Y5 | TRIRE_Xyn2-T2C/T28C/K58R/+191D |
| Y5-T120A | TRIRE_Xyn2-T2C/T28C/K58R/T120A/+191D |

The mutations introduced and the results obtained are illustrated in table 7

TABLE 7

Mutations introduced and results obtained. The backbones used are in bold.

| Mutant | WU-AX act | WE-AX act | WU-AX/WE-AX |
|---|---|---|---|
| #154/N141Q | 1.965 | 13 | 146 |
| #154/N54Q/N141Q | 1.611 | 10 | 159 |
| #160/N54Q | 1.203 | 7 | 161 |
| #160/N141Q | 1.785 | 10 | 175 |
| #154/N54W/N141Q | 824 | 7 | 118 |
| #160/N54W/N141Q | 1.005 | 6 | 169 |
| Y5/S63W | 918 | 25 | 36 |
| Y5 | 35.550 | 1.487 | 24 |
| #154 | 10.350 | 106 | 98 |
| #160 | 5.400 | 34 | 157 |

SEQUENCE LISTING (amino acids in bold are the amino acid, which corresponds to T110 of SEQ ID No. 1):

The amino acid sequence of the mature Bacillus subtilis wildtype xylanase (SEQ ID No 1):
ASTDYWQNWTDGGGIVNAVNGSGGNYSVNWSNTGNFVVGKGWTTGSPFRT
INYNAGVWAPNGNGYLTLYGWTRSPLIEYYVVDSWGTYRPTGTYKGTVKSDGGTYDIYTT
TRYNAPSIDGDRTTFTQYWSVRQSKRPTGSNATITFSNHVNAWKSHGMNLGSNWAYQV
MA TEGYQSSGSSNVTVW The amino acid sequence of the mature Trichoderma reesei xylanase (SEQ ID No 2), also referred to herein as Y5:
QCIQPGTGYNNGYFYSYWNDGHGGVTYCNGPGGQFSVNWSNSGNFVGGKGWQPGTKN
RVINFSGSYNPNGNSYLSVYGWSRNPLIEYYIVENFGTYNPSTGATKLGEVTSDGSVYDIY
RTQRVNQPSIIGTATFYQYWSVRRNHRSSGSVNTANHFNAWAQQGLTLGTMDYQIVAVE
GYFSSGSASITVSD The amino acid sequence of the mature Thermomyces lanuginosus XynA wildtype xylanase (SEQ ID No. 3):
QTTPNSEGWHDGYYYSWWSDGGAQATYTNLEGGTYEISWGDGGNLVGGKGWNPGLNA
RAIHFEGVYQPNGNSYLAVYGWTRNPLVEYYIVENFGTYDPSSGATDLGTVECDGSIYRLG
KTTRVNAPSIDGTQTFDQYWSVRQDKRTSGTVQTGCHFDAWARAGLNVNGDHYYQIVA
TEGYFSSGYARITVADVG The amino acid sequence of the mature Streptomyces viridosporus xylanase (Seq ID No 4):
WTDAQGTVSMDLGSGGTYSTQWRNTGNFVAGKGWSTGGRKTVNYSGTFNPSGNAYLT
LYGWTTGPLIEYYIVDNWGTYRPTGKYKGTVTSDGGTYDIYKTTRYNAPSIEGTKTFDQYW
SVRQSKRTGGTITSGNHFDAWARNGMNLGNHNYMIMATEGYQSSGSSTITV Seq ID No 5 (gi|139868|sp|P18429.1|XYNA BACSU RecName: Full = Endo-1,4-beta-xylanase A; Short = Xylanase A; AltName: Full = 1,4-beta-D-xylan xylanohydrolase A):
MFKFKKNFLVGLSAALMSISLFSATASAASTDYWQNWTDGGGIVNAVNGSGGNYSVNW
SNTGNFVVGKGWTTGSPFRTINYNAGVWAPNGNGYLTLYGWTRSPLIEYYVVDSWGTYR
PTGTYKGTVKSDGGTYDIYTTTRYNAPSIDGDRTTFTQYWSVRQSKRPTGSNATITFSNH
VNAWKSHGMNLGSNWAYQVMATEGYQSSGSSNVTVW Seq ID No 6 (gi|2302074|emb|CAA03092.1| unnamed protein product [unidentified]):
MRQKKLTLILAFLVCFALTLPAEIIQAQIVTDNSIGNHDGYDYEFWKDSGGSGTMILNHGG
TFSAQWNNVNNILFRKGKKFNETQTHQQVGNMSINYGANFQPNGNAYLCVYGWTVDPLV
EYYIVDSWGNWRPPGATPKGTITVDGGTYDIYETLRVNQPSIKGIATFKQYWSVRRSKRT SEQUENCE LISTING (amino acids in bold are the amino acid, which corresponds to T110 of SEQ ID No. 1):

SGTISVSNHFRAWENLGMNMGKMYEVALTVEGYQSSGSANVYSNTLRINGNPLSTISND
ESITLDKNN

Seq ID No 7 (gi|167246404|gb|ABZ24364.1| Sequence 5 from U.S.
Pat. No. 7,314,743):
MVSFTSLLAASPPSRASCRPAAEVESVAVEKRQTIQPGTGYNNGYFYSYWNDGHGGVTYT
NGPGGQFSVNWSNSGNFVGGKGWQPGTKNKVINFSGSYNPNGNSYLSVYGWSRNPLIE
YYIVENFGTYNPSTGATKLGEVTSDGSVYDIYRTQRVNQPSIIGTATFYQYWSVRRNHRSS
GSVNTANHFNAWAQQGLTLGTMDYQIVAVEGYFSSGSASITVS Seq ID No 8 (gi|5969551|gb|AAE10889.1| Sequence 2 from U.S.
Pat. No. 5,817,500):
MVGFTPVALAALAATGALAFPAGNATELEKRQTTPNSEGWHDGYYYSWWSDGGAQATYT
NLEGGTYEISWGDGGNLVGGKGWNPGLNARAIHFEGVYQPNGNSYLAVYGWTRNPLVEY
YIVENFGTYDPSSGATDLGTVECDGSIYRLGKTTRVNAPSIDGTQTFDQYWSVRQDKRTS
GTVQTGCHFDAWARAGLNVNGDHYYQIVATEGYFSSGYARITVADVG Seq ID No 9 (gi|76059070|emb|CAJ30753.1| unnamed protein product
[*Paenibacillus pabuli*]):
MFKFGKKLLTVVLAASMSFGVFAATTGATDYWQNWTDGGGTVNAVNGSGGNYSVNWQ
NTGNFVVGKGWTYGTPNRVVNYNAGVFSPSGNGYLTFYGWTRNALIEYYVVDNWGTYRP
TGTYKGTVTSDGGTYDIYTTMRYNQPSIDGYSTFPQYWSVRQSKRPIGVNSQITFQNHVN
AWASKGMYLGNSWSYQVMATEGYQSSGSSNVTVW Seq ID No 10 (gi|74197761|emb|CAJ29666.1| unnamed protein product
[*Bacillus halodurans*]):
MFKFVTKVLTVVIAATISFCLSAVPASANTYWQYWTDGGGTVNATNGPGGNYSVTWRDT
GNFVVGKGWEIGSPNRTIHYNAGVWEPSGNGYLTLYGWTRNQLIEYYVVDNWGTYRPTG
THRGTVVSDGGTYDIYTTMRYNAPSIDGTQTFQQFWSVRQSKRPTGNNVSITFSNHVNA
WRNAGMNLGSSWSYQVLATEGYQSSGRSNVTVW Seq ID No 11 (gi|4756811|emb|CAB42305.1| unnamed protein product
[unidentified]):
MRQKKLTFILAPLVCFALTLPAEIIQAQIVTDNSIGNHDGYDYEFWKDSGGSGTMILNHGG
TFSAQWNNVNNILFRKGKKFNETQTHQQVGNMSINYGANFQPNGNAYLCVYGWTVDPLV
EYYIVDSWGNWRPPGATPKGTITVDGGTYDIYETLRVNQPSIKGIATFKQYWSVRRSKRT
SGTISVSNHFRAWENLGMNMGKMYEVALTVEGYQSSGSANVYSNTLRINGNPLSTISND
KSITLDKNN Seq ID No 12 (gi|2293951|emb|CAA02246.1| unnamed protein product
[*Bacillus subtilis*] *Bacillus subtilis*: (U.S. Pat. No. 5,306,633)):
MFKFKKKFLVGLTAAFMSISMFSATASAAGTDYWQNWTDGGGTVNAVNGSGGNYSVNW
SNTGNFVVGKGWTTGSPFRTINYNAGVWAPNGNGYLTLYGWTRSPLIEYYVVDSWGTYR
PTGTYKGTVKSDGGTYDIYTTTRYNAPSIDGDNTTFTQYWSVRQSKRPTGSNAAITFSNH
VNAWKSHGMNLGSNWAYQVLATEGYKSSGSSNVTVW Seq ID No 13 (gi|42688917|gb|AAS31735.1| Sequence 14 from U.S.
Pat. No. 6,682,923):
MNLRKLRLLFVMCIGLTLILTAVPAHARTITNNEMGNHSGYDYELWKDYGNTSMTLNNGG
AFSAGWNNIGNALFRKGKKFDSTRTHHQLGNISINYNASFNPGGNSYLCVYGWTQSPLAE
YYIVDSWGTYRPTGAYKGSFYADGGTYDIYETTRVNQPSIIGIATFKQYWSVRQTKRTSGT
VSVSAHFRKWESLGMPMGKMYETAFTVEGYQSSGSANVMTNQLFIGN Seq ID No 14 (gi|10040204|emb|CAC07798.1| unnamed protein product
[*Penicillium funiculosum*]):
MKLFLAAIVLCATAATAFPSELAQRAAGDLSKRQSITTSQTGTNNGYYYSFWTNGGGEVTY
TNGDNGEYSVTWVDCGDFTSGKGWNPANAQTVTYSGEFNPSGNAYLAVYGWTTDPLVE
YYILESYGTYNPSSGLTSLGQVTSDGGTYDIYSTQRVNQPSIEGTSTFNQYWSVRTEKRVG
GTVTTANHFAAWKALGLEMGTYNYMIVSTEGYESSGSSTITVS Seq ID No 15 (gi|2302074|emb|CAA03092.1| unnamed protein product
[unidentified]):
QIVTDNSIGNHDGYDYEFWKDSGGSGTMILNHGGTFSAQWNNVNNILFRKGKKFNETQT
HQQVGNMSINYGANFQPNGNAYLCVYGWTVDPLVEYYIVDSWGNWRPPGATPKGTITVD
GGTYDIYETLRVNQPSIKGIATFKQYWSVRRSKRTSGTISVSNHFRAWENLGMNMGKMY
EVALTVEGYQSSGSANVYSNTLRINGNPLSTISNDESITLDKNN Seq ID No 16 (gi|167246404|gb|ABZ24364.1| Sequence 5 from U.S.
Patent No. 7,314,743):
QTIQPGTGYNNGYFYSYWNDGHGGVTYTNGPGGQFSVNWSNSGNFVGGKGWQPGTKN
KVINFSGSYNPNGNSYLSVYGWSRNPLIEYYIVENFGTYNPSTGATKLGEVTSDGSVYDIY
RTQRVNQPSIIGTATFYQYWSVRRNHRSSGSVNTANHFNAWAQQGLTLGTMDYQIVAVE
GYFSSGSASITVS -continued SEQUENCE LISTING (amino acids in bold are the amino acid, which corresponds to T110 of SEQ ID No. 1):

Seq ID No 17 (gi|76059070|emb|CAJ30753.1| unnamed protein product [Paenibacillus pabuli]):
TDYWQNWTDGGGTVNAVNGSGGNYSVNWQNTGNFVVGKGWTYGTPNRVVNYNAGVF
SPSGNGYLTFYGWTRNALIEYYVVDNWGTYRPTGTYKGTVTSDGGTYDIYTTMRYNQPSI
DGYSTFPQYWSVRQSKRPIGVNSQITFQNHVNAWASKGMYLGNSWSYQVMATEGYQSS
GSSNVTVW Seq ID No 18 (gi|74197761|emb|CAJ29666.1|unnamed protein product [Bacillus halodurans]):
NTYWQYWTDGGGTVNATNGPGGNYSVTWRDTGNFVVGKGWEIGSPNRTIHYNAGVWE
PSGNGYLTLYGWTRNQLIEYYVVDNWGTYRPTGTHRGTVVSDGGTYDIYTTMRYNAPSID
GTQTFQQFWSVRQSKRPTGNNVSITFSNHVNAWRNAGMNLGSSWSYQVLATEGYQSSG
RSNVTVW Seq ID No 19 (gi|4756811|emb|CAB42305.1| unnamed protein product):
QIVTDNSIGNHDGYDYEFWKDSGGSGTMILNHGGTFSAQWNNVNNILFRKGKKFNETQT
HQQVGNMSINYGANFQPNGNAYLCVYGWTVDPLVEYYIVDSWGNWRPPGATPKGTITVD
GGTYDIYETLRVNQPSIKGIATFKQYWSVRRSKRTSGTISVSNHFRAWENLGMNMGKMY
EVALTVEGYQSSGSANVYSNTLRINGNPLSTISNDKSITLDKNN Seq ID No 20 (gi|2293951|emb|CAA02246.1| unnamed protein product [Bacillus subtilis] Bacillus subtilis: (U.S. Pat. No. 5,306,633)):
AGTDYWQNWTDGGGTVNAVNGSGGNYSVNWSNTGNFVVGKGWTTGSPFRTINYNAGV
WAPNGNGYLTLYGWTRSPLIEYYVVDSWGTYRPTGTYKGTVKSDGGTYDIYTTTRYNAPS
IDGDNTTFTQYWSVRQSKRPTGSNAAITFSNHVNAWKSHGMNLGSNWAYQVLATEGYK
SSGSSNVTVW Seq ID No 21 (gi|42688917|gb|AAS31735.1| Sequence 14 from U.S. Pat. No. 6,682,923):
RTITNNEMGNHSGYDYELWKDYGNTSMTLNNGGAFSAGWNNIGNALFRKGKKFDSTRT
HHQLGNISINYNASFNPGGNSYLCVYGWTQSPLAEYYIVDSWGTYRPTGAYKGSFYADGG
TYDIYETTRVNQPSIIGIATFKQYWSVRQTKRTSGTVSVSAHFRKWESLGMPMGKMYETA
FTVEGYQSSGSANVMTNQLFIGN Seq ID No 22 (gi|10040204|emb|CAC07798.1| unnamed protein product [Penicillium funiculosum]):
AFPSELAQRAAGDLSKRQSITTSQTGTNNGYYYSFWTNGGGEVTYTNGDNGEYSVTWVD
CGDFTSGKGWNPANAQTVTYSGEFNPSGNAYLAVYGWTTDPLVEYYILESYGTYNPSSGL
TSLGQVTSDGGTYDIYSTQRVNQPSIEGTSTFNQYWSVRTEKRVGGTVTTANHFAAWKA
LGLEMGTYNYMIVSTEGYESSGSSTITVS SEQ ID No 23 shows the amino acid sequence of the mature Bacillus subtilis xylanase variant, BS3 (wildtype with D11F/R122D mutations):
ASTDYWQNWTFGGGIVNAVNGSGGNYSVNWSNTGNFVVGKGWTTGSPFRTINYNAGV
WAPNGNGYLTLYGWTRSPLIEYYVVDSWGTYRPTGTYKGTVKSDGGTYDIYTTTRYNAPS
IDGDDTTFTQYWSVRQSKRPTGSNATITFSNHVNAWKSHGMNLGSNWAYQVMATEGYQ
SSGSSNVTVW Seq ID No 24 shows the sequence of the mature wheat xylanase inhibitor sequence:
MPPVLLLVLAASLVALPSCQSLPVLAPVTKDPATSLYTIPFHDGASLVLDVAGPLVWSTCDG
GQPPAEIPCSSPTCLLANAYPAPGCPAPSCGSDKHDKPCTAYPYNPVSGACAAGSLSHTRF
VANTTDGSKPVSKVNVGVLAACAPSKLLASLPRGSTGVAGLANSGLALPAQVASAQKVAN
RFLLCLPTGGPGVAIFGGGPVPWPQFTQSMPYTPLVTKGGSPAHYISARSIVVGDTRVPVP
EGALATGGVMLSTRLPYVLLRPDVYRPLMDAFTKALAAQHANGAPVARAVEAVAPFGVCY
DTKTLGNNLGGYAVPNVQLGLDGGSDWTMTGKNSMVDVKQGTACVAFVEMKGVAAGD
GRAPAVILGGAQMEDFVLDFDMEKKRLGFSRLPHFTGCGGL Seq ID No 25 (sequence 11 of U.S. Pat. No. 6,682,923):
ASTDWWENWTIGGGIVNAVNGSGGNYSVNWSNTGNFDVAKGWTTGSPFRTINYNAGV
WAPNGWGELELYGWTRSPLIEYLVVDSWGTNRPTGTYKGTVKSDGGTYDIYTDTRYNYP
SEDGDRTTMTQYSSVRQSKRPTGSNATITFTNHVNAWKSHGMNLGSNWAYQDMATEGY
QSSGSSNVTVW Embodiments of the Invention:

1. A polypeptide having xylanase activity and comprising an amino acid sequence, said amino acid sequence having at least 88% identity with SEQ ID No. 1 or having at least 75% identity with an amino acid sequence selected from SEQ ID No. 2-22, and which polypeptide has an amino acid modification in position 110, wherein said position 110 is determined as the position corresponding to position 110 of B. subtilis xylanase sequence shown as SEQ ID No. 1 by alignment.

2. A polypeptide having xylanase activity and comprising an amino acid sequence, said amino acid sequence having at least 88% identity with SEQ ID No. 1 and which polypeptide has an amino acid modification in position 110, wherein said position 110 is determined as the position corresponding to position 110 of *B. subtilis* xylanase sequence shown as SEQ ID No. 1 by alignment.

3. A polypeptide having xylanase activity and comprising an amino acid sequence, said amino acid sequence having at least 75% identity with SEQ ID No. 2 and which polypeptide has an amino acid modification in position 110, wherein said position 110 is determined as the position corresponding to position 110 of *B. subtilis* xylanase sequence shown as SEQ ID No. 1 by alignment.

4. A polypeptide having xylanase activity and comprising an amino acid sequence, said amino acid sequence having at least 75% identity with SEQ ID No. 3 and which polypeptide has an amino acid modification in position 110, wherein said position 110 is determined as the position corresponding to position 110 of *B. subtilis* xylanase sequence shown as SEQ ID No. 1 by alignment.

5. The polypeptide according to embodiment 2, wherein said polypeptide has at least 90, 92 or 95% identity with SEQ ID No. 1.

6. The polypeptide according to any one of the embodiments 1 and 3-4, wherein said polypeptide has at least 76, 78, 80, 85, 90, 95, 98 or 95% identity with the sequence with which is has the highest percentage of identity selected from SEQ ID No. 2-22.

7. The polypeptide according embodiment 3, wherein said polypeptide has at least 76, 78, 80, 85, 90, 95, 98 or 95% identity with SEQ ID No. 2.

8. The polypeptide according embodiment 4, wherein said polypeptide has at least 76, 78, 80, 85, 90, 95, 98 or 95% identity with SEQ ID No. 3.

9. The polypeptide according to any one of the embodiments 1-6 having a β-jelly roll fold.

10. The polypeptide according to any one of the embodiments 1-9, wherein the amino acid modification in position 110 is an amino acid substitution.

11. The polypeptide according to any one of the embodiments 1-10, wherein the amino acid modification in position 110 is a substitution to any one different amino acid residue selected from the group consisting of: alanine, arginine, asparagine, aspartic acid, cysteine, glutamic acid, glutamine, glycine, histidine, isoleucine, leucine, lysine, methionine, phenylalanine, proline, serine, tryptophan, tyrosine and valine.

12. The polypeptide according to any one of the embodiments 1-11, wherein the amino acid modification in position 110 is a substitution to any one different amino acid residue selected from the group consisting of: glutamic acid, tryptophan, alanine and cysteine.

13. The polypeptide according to embodiment 12, wherein the amino acid modification in position 110 is a substitution to alanine.

14. The polypeptide according to any one of the embodiments 1-13 having a total number of amino acids of less than 250, such as less than 240, such as less than 230, such as less than 220, such as less than 210, such as less than 200 amino acids, such as in the range of 160 to 240, such as in the range of 160 to 220 amino acids.

15. The polypeptide according to any one of the embodiments 1-14, comprising one or more modification(s) at any one or more of amino acid positions: 11, 12, 13, 34, 54, 77, 81, 99, 104, 113, 114, 118, 122, 141, 154, 159, 162, 164, 166 and 175, the position(s) being determined as the corresponding position of *B. subtilis* amino acid sequence shown as SEQ ID No. 1.

16. The polypeptide according to any one of the embodiments 1-15, comprising one or more amino acid substitutions selected from the group consisting of: 11F, 12F, 54Q, 54W, 122D, 113A, 13Y, 113D, 141Q, 175L, 122F, 34K, 99Y, 104W, 154R, 159D, 175K, 81I, 166F, 162E, 162D, 164F, 114D, 114Y, 114F, 118V, 175K, 77L, 77M, 77S, 77V, and 77Y, the position(s) being determined as the corresponding position of *B. subtilis* amino acid sequence shown as SEQ ID No. 1.

17. The polypeptide according to any one of the embodiments 2, 5, 9-16, comprising one or more amino acid substitutions selected from the group consisting of: D11F, G12F, N54Q, R122D, Y113A, G13Y, Y113D, N141Q, Q175L, R122F, G34K, K99Y, T104W, K154R, N159D, Q175K, V81I, Y166F, S162E, S162D, W164F, N114D, N114Y, N114F, I118V, I77L, I77M, I77S, I77V, and I77Y, the position(s) being determined as the corresponding position of *B. subtilis* amino acid sequence shown as SEQ ID No. 1.

18. The polypeptide according to any one of the embodiments 1-17, comprising one or more modification(s) at any one or more of amino acid positions: 13, 99, 104, 113, 122, 154, 159 and 175, the position(s) being determined as the corresponding position of *B. subtilis* amino acid sequence shown as SEQ ID No. 1.

19. The polypeptide according to any one of the embodiments 1-18, comprising substitution(s) at the amino acid positions: 13, 99, 104, 113, 122, 154, 159 and 175, the position(s) being determined as the corresponding position of *B. subtilis* amino acid sequence shown as SEQ ID No. 1.

20. The polypeptide according to any one of the embodiments 18-19, further comprising one or more modification(s) at any one or more of amino acid positions: 114 and 166, the position(s) being determined as the corresponding position of *B. subtilis* amino acid sequence shown as SEQ ID No. 1.

21. The polypeptide according to any one of the embodiments 18-19, further comprising one or more substitution(s) at any one or more of amino acid positions: 114 and 166, the position(s) being determined as the corresponding position of *B. subtilis* amino acid sequence shown as SEQ ID No. 1.

22. The polypeptide according to any one of the embodiments 18-19, comprising substitution(s) in at least at four of the following amino acid positions: 13, 99, 104, 113, 114, 122, 154, 159, 166, and 175, the position(s) being determined as the corresponding position of *B. subtilis* amino acid sequence shown as SEQ ID No. 1.

23. The polypeptide according to any one of the embodiments 18-22, comprising substitution(s) at the amino acid positions: 13, 99, 104, 113, 114, 122, 154, 159 and 175, the position(s) being determined as the corresponding position of *B. subtilis* amino acid sequence shown as SEQ ID No. 1.

24. The polypeptide according to any one of the embodiments 18-22, comprising substitution(s) at the amino acid positions: 13, 99, 104, 113, 122, 154, 159, 166 and 175, the position(s) being determined as the corresponding position of *B. subtilis* amino acid sequence shown as SEQ ID No. 1.

25 The polypeptide according to any one of the embodiments 18-20, comprising substitution(s) at the amino acid positions: 13, 99, 104, 113, 122, 154, 159, and 175, the position(s) being determined as the corresponding position of *B. subtilis* amino acid sequence shown as SEQ ID No. 1.

26. The polypeptide according to any one of the embodiments 22-25, comprising one or more amino acid substitutions selected from the group consisting of: 13Y, 99Y, 104W, 110A, 113D, 114D, 114F, 122F, 154R, 159D, 166F, 175K, and 175L, the position(s) being determined as the corresponding position of *B. subtilis* amino acid sequence shown as SEQ ID No. 1.

27. The polypeptide according to any one of the embodiments 1-26, wherein the amino acid sequence of said polypeptide has at least five, six, seven, eight, nine or ten amino acid substitutions compared to the sequence selected among SEQ ID No. 1-22 with which it has the highest identity.

28. The polypeptide according to embodiment 27, wherein the amino acid sequence of said polypeptide has at least nine or ten amino acid substitutions.

29. The polypeptide according to any one of the embodiments 1-28, comprising one or more amino acid substitutions selected from the group consisting of:
a. D11F, R122D and T110A;
b. D11F, R122D, T110A and Y113A;
c. G13Y, T110A, Y113D, R122D and Q175L;
d. G13Y, T110A, Y113D, R122F and Q175L;
e. G13Y, G34K, T110A, Y113D, R122D and Q175L;
f. G13Y, K99Y, T104W, T110A, Y113D, R122F, K154R, N159D and Q175K;
g. G13Y, K99Y, T104W, T110A, Y113D, R122F, K154R, N159D, Q175 and V81I;
h. G13Y, K99Y, T104W, T110A, Y113D, R122F, K154R, N159D, Y166F and Q175L;
i. G13Y, T110A, Y113D, R122D, K154R, N159D and Q175L;
j. G13Y, K99Y, T104W, T110A, Y113D, R122F, K154R, N159D and Q175L;
k. G13Y, T110A, Y113D, R122D, S162E and Q175L;
l. G13Y, T110A, Y113D, R122D, S162D and Q175L;
m. G13Y, T110A, Y113D, R122D, W164F and Q175L;
n. G13Y, K99Y, T104W, T110A, Y113D, N114D, R122F, K154R, N159D and Q175L;
o. G13Y, K99Y, T104W, T110A, Y113D, N114Y, R122F, K154R, N159D and Q175L;
p. G13Y, K99Y, T104W, T110A, Y113D, N114F, R122F, K154R, N159D and Q175L;
q. G13Y, K99Y, T104W, T110A, Y113D, I118V, R122F, K154R, N159D and Q175L;
r. G13Y, K99Y, T104W, T110A, Y113D, N114Y, R122F, K154R, N159D and Q175K;
s. G13Y, K99Y, T104W, T110A, Y113D, N114D, R122F, K154R, N159D and Q175K;
t. G13Y, I77L, K99Y, T104W, T110A, Y113D, R122F, K154R, N159D and Q175L;
u. G13Y, I77M, K99Y, T104W, T110A, Y113D, R122F, K154R, N159D and Q175L;
v. G13Y, I77S, K99Y, T104W, T110A, Y113D, R122F, K154R, N159D and Q175L;
w. G13Y, I77V, K99Y, T104W, T110A, Y113D, R122F, K154R, N159D and Q175L;
x. G13Y, I77Y, K99Y, T104W, T110A, Y113D, R122F, K154R, N159D and Q175L y. G13Y, K99Y, T104W, T110A, Y113D, R122F, N141Q, K154R, N159D, and Q175L;
z. G13Y, N54Q, K99Y, T104W, T110A, Y113D, R122F, N141Q, K154R, N159D, and Q175;
aa. G13Y, N54W, K99Y, T104W, T110A, Y113D, R122F, 141Q, K154R, N159D, and 175L;
bb. G13Y, N54Q, K99Y, T104W, T110A, Y113D, N114F, R122F, K154R, N159D, and Q175L;
cc. G13Y, K99Y, T104W, T110A, Y113D, N114F, R122F, 141Q, K154R, N159D, and Q175L;
dd. G13Y, 54Q, K99Y, T104W, T110A, Y113D, N114F, R122F, 141Q, K154R, N159D, and Q175L;
the position(s) being determined as the corresponding position of *B. subtilis* amino acid sequence shown as SEQ ID No. 1.

30. The polypeptide according to any one of the embodiments 1-29, comprising one or more amino acid substitutions selected from the group consisting of:
a. G13Y, K99Y, T104W, T110A, Y113D, N114D, R122F, K154R, N159D and Q175K;
b. G13Y, K99Y, T104W, T110A, Y113D, R122F, K154R, N159D, Y166F and Q175L;
c. G13Y, K99Y, T104W, T110A, Y113D, R122F, K154R, N159D and Q175L;
d. G13Y, K99Y, T104W, T110A, Y113D, N114D, R122F, K154R, N159D and Q175L;
e. G13Y, K99Y, T104W, T110A, Y113D, N114F, R122F, K154R, N159D and Q175L;
the position(s) being determined as the corresponding position of *B. subtilis* amino acid sequence shown as SEQ ID No. 1.

31. The polypeptide according to any one of the embodiments 1-30 having bran solubilisation activity.

32. The polypeptide according to any one of the embodiments 1-31 in isolated form.

33. The polypeptide according to any one of the embodiments 1-32, wherein the amino acid modification in position 110 is not T110D.

34. The polypeptide according to any one of embodiments 1-33 having an improved xylanase activity compared to the *B. subtilis* amino acid sequence shown as SEQ ID No. 1 as measured in a xylanase activity assay.

35. The polypeptide according to any one of embodiments 1-34 having an improved xylanase activity as a result of the modification in position 110.

36. The polypeptide according to any one of embodiments 1-35 having an improved bran solubilisation activity compared to the *B. subtilis* amino acid sequence shown as SEQ ID No. 1 as measured in a bran solubilisation activity assay.

37. The polypeptide according to any one of embodiments 1-36 having an improved bran solubilisation activity as a result of the modification in position 110.

38. The polypeptide according to any one of embodiments 1-37 having a reduced sensitivity to a xylanase inhibitor.

39. The polypeptide according to any one of embodiments 1-38, wherein said polypeptide has an amino acid sequence comprising modifications at positions selected from the list consisting of:
a) 13/110/113/122/154/159/175;
b) 13/99/104/110/113/122/154/159/166/175;
c) 13/99/104/110/113/114/122/154/159/175;
d) 13/110/113/122/175;
e) 13/99/104/110/113/122/154/159/175;
f) 13/99/104/110/113/122/154/159/175;
g) 13/99/104/110/113/114/122/154/159/175;
h) 13/99/104/110/113/114/122/154/159/175;
i) 13/99/104/110/113/114/122/154/159/175;
j) 13/99/104/110/113/114/122/154/159/175;
k) 13/77/99/104/110/113/122/154/159/175;
l) 13/81/99/104/110/113/122/154/159/175;
m) 13/110/113/122/164/175;
n) 13/110/113/122/162/175;
o) 13/110/113/122/175;
p) 11/122/110/113;
q) 13/77/99/104/110/113/122/154/159/175;
r) 11/122/110;
s) 13/34/110/113/122/175;
t) 13/77/99/104/110/113/122/154/159/175;
u) 13/77/99/104/110/113/122/154/159/175;
v) 13/99/104/110/113/118/122/154/159/175;
w) 13/110/113/122/162/175;
x) 13/77/99/104/110/113/122/154/159/175;

y) 13/99/104/110/113/122/141/154/159/175;
z) 13/54/99/104/110/113/122/141/154/159/175;
aa) 13/54/99/104/110/113/122/141/154/159/175;
bb) 13/54/99/104/110/113/114/122/154/159/175;
cc) 13/99/104/110/113/114/122/141/154/159/175; and
dd) 13/54/99/104/110/113/114/122/141/154/159/175, the position(s) being determined as the corresponding position of *subtilis* amino acid sequence shown as SEQ ID No. 1.

40. The polypeptide according to any one of embodiments 1-39, wherein said polypeptide has an amino acid sequence comprising amino acid substitutions selected from the list consisting of:
a) 13Y/110A/113D/122D/154R/159D/175L;
b) 13Y/99Y/104W/110A/113D/122F/154R/159D/166F/175L;
c) 13Y/99Y/104W/110A/113D/114F/122F/154R/159D/175L;
d) 13Y/110A/113D/122F/175L;
e) 13Y/99Y/104W/110A/113D/122F/154R/159D/175L;
f) 13Y/99Y/104W/110A/113D/122F/154R/159D/175K;
g) 13Y/99Y/104W/110A/113D/114D/122F/154R/159D/175K;
h) 13Y/99Y/104W/110A/113D/114Y/122F/154R/159D/175L;
i) 13Y/99Y/104W/110A/113D/114D/122F/154R/159D/175L;
j) 13Y/99Y/104W/110A/113D/114Y/122F/154R/159D/175K;
k) 13Y/77L/99Y/104W/110A/113D/122F/154R/159D/175L;
l) 13Y/81I/99Y/104W/110A/113D/122F/154R/159D/175L;
m) 13Y/110A/113D/122D/164F/175L;
n) 13Y/110A/113D/122D/162D/175L;
o) 13Y/110A/113D/122D122D/175L;
p) 11F/122D/110A/113A;
q) 13Y/77Y/99Y/104W/110A/113D/122F/154R/159D/175L;
r) 11F/122D/110A;
s) 13Y/34K/110A/113D/122D122D/175L;
t) 13Y/77V/99Y/104W/110A/113D/122F/154R/159D/175L;
u) 13Y/77M/99Y/104W/110A/113D/122F/154R/159D/175L;
v) 13Y/99Y/104W/11A/113D/118V/122F/154R/159D/175L;
w) 13Y/110A/113D/122D122D/162E/175L;
x) 13Y/77S/99Y/104W/110A/113D/122F/154R/159D/175L;
y) 13Y/99Y/104W/110A/113D/122F/141Q/154R/159D/175L;
z) 13Y/54Q/99Y/104W/110A/113D/122F/141Q/154R/159D/175L;
aa) 13Y/54W/99Y/104W/110A/113D/122F/141Q/154R/159D/175L;
bb) 13Y/54Q/99Y/104W/110A/113D/114F/122F/154R/159D/175L;
cc) 13Y/99Y/104W/110A/113D/114F/122F/141Q/154R/159D/175L; and
dd) 13Y/54Q/99Y/104W/110A/113D/114F/122F/141Q/154R/159D/175L;

the position(s) being determined as the corresponding position of *subtilis* amino acid sequence shown as SEQ ID No. 1.

41. The polypeptide according to any one of embodiments 1-40, wherein said polypeptide has an amino acid sequence of SEQ ID No. 1 comprising amino acid substitutions selected from the list consisting of a) G13Y/T110A/Y113D/R122D/K154R/N159D/Q175L;
b) G13Y/K99Y/T10404W/T110A/Y113D/R122F/K154R/N159D/Y166F/Q175L;
c) G13Y/K99Y/T10404W/T110A/Y113D/N114F/R122F/K154R/N159D/Q175L;
d) G13Y/T110A/Y113D/R122F/Q175L;
e) G13Y/K99Y/T10404W/T110A/Y113D/R122F/K154R/N159D/Q175L;
f) G13Y/K99Y/T104W/T110A/Y113D/R122F/K154R/N159D/Q175K;
g) G13Y/K99Y/T104W/T110A/Y113D/N114D/R122F/K154R/N159D/Q175K;
h) G13Y/K99Y/T10404W/T110A/Y113D/N114Y/R122F/K154R/N159D/Q175L;
i) G13Y/K99Y/T10404W/T110A/Y113D/N114D/R122F/K154R/N159D/Q175L;
j) G13Y/K99Y/T10404W/T110A/Y113D/N114Y/R122F/K154R/N159D/Q175K;
k) G13Y/I77L/K99Y/T10404W/T110A/Y113D/R122F/K154R/N159D/Q175L;
l) G13Y/V81I/K99Y/T104W/T110A/Y113D/R122F/K154R/N159D/Q175L;
m) G13Y/T110A/Y113D/R122D/W164F/Q175L;
n) G13Y/T110A/Y113D/R122D/S162D/Q175L;
o) G13Y/T110A/Y113D/R122D/Q175L;
p) D11F/R122D/T110A/Y113A;
q) G13Y/I77Y/K99Y/T104W/T110A/Y113D/R122F/K154R/N159D/Q175L;
r) D11F/R122D/T110A;
s) G13Y/G34K/T110A/Y113D/R122D/Q175L;
t) G13Y/I77V/K99Y/T104W/T110A/Y113D/R122F/K154R/N159D/Q175L;
u) G13Y/I77M/K99Y/T104W/T110A/Y113D/R122F/K154R/N159D/Q175L;
v) G13Y/K99Y/T104W/T110A/Y113D/I118V/R122F/K154R/N159D/Q175L;
w) G13Y/T110A/Y113D/R122D/S162E/Q175L; and
x) G13Y/I77S/K99Y/T104W/T110A/Y113D/R122F/K154R/N159D/Q175L
y) G13Y/K99Y/T104W/T110A/Y113D/R122F/N141Q/K154R/N159D/Q175L;
z) G13Y/N54Q/K99Y/T104W/T110A/Y113D/R122F/N141Q/K154R/N159D/Q1 75L;
aa) G13Y/N54W/K99Y/T104W/T110A/Y113D/R122F/141Q/K154R/N159D/17 5L;
bb) G13Y/N54Q/K99Y/T104W/T110A/Y113D/N114F/R122F/K154R/N159D/Q 175L;
cc) G13Y/K99Y/T10404W/T110A/Y113D/N114F/R122F/141Q/K154R/N159D/Q17 5L; and
dd) G13Y/54Q/K99Y/T104W/T110A/Y113D/N114F/R122F/141Q/K154R/N159D/Q175L.

42. The polypeptide according to any one of embodiments 1-41, wherein said polypeptide has an amino acid sequence, which consists of amino acid substitutions selected from the list consisting of:
a) 13Y/110A/113D/122D/154R/159D/175L;
b) 13Y/99Y/104W/110A/113D/122F/154R/159D/166F/175L;
c) 13Y/99Y/104W/110A/113D/114F/122F/154R/159D/175L;
d) 13Y/110A/113D/122F/175L;
e) 13Y/99Y/104W/110A/113D/122F/154R/159D/175L;
f) 13Y/99Y/104W/110A/113D/122F/154R/159D/175K;
g) 13Y/99Y/104W/110A/113D/114D/122F/154R/159D/175K;
h) 13Y/99Y/104W/110A/113D/114Y/122F/154R/159D/175L;

i) 13Y/99Y/104W/110A/113D/114D/122F/154R/159D/175L;
j) 13Y/99Y/104W/110A/113D/114Y/122F/154R/159D/175K;
k) 13Y/77L/99Y/104W/110A/113D/122F/154R/159D/175L;
l) 13Y/81I/99Y/104W/110A/113D/122F/154R/159D/175L;
m) 13Y/110A/113D/122D/164F/175L;
n) 13Y/110A/113D/122D/162D/175L;
o) 13Y/110A/113D/122D122D/175L;
p) 11F/122D/110A/113A;
q) 13Y/77Y/99Y/104W/110A/113D/122F/154R/159D/175L;
r) 11F/122D/110A;
s) 13Y/34K/110A/113D/122D122D/175L;
t) 13Y/77V/99Y/104W/110A/113D/122F/154R/159D/175L;
u) 13Y/77M/99Y/104W/110A/113D/122F/154R/159D/175L;
v) 13Y/99Y/104W/110A/113D/118V/122F/154R/159D/175L;
w) 13Y/110A/113D/122D122D/162E/175L; and
x) 13Y/77S/99Y/104W/110A/113D/122F/154R/159D/175L
y) 13Y/99Y/104W/110A/113D/122F/141Q/154R/159D/175L;
z) 13Y/54Q/99Y/104W/110A/113D/122F/141Q/154R/159D/175L;
aa) 13Y/54W/99Y/104W/110A/113D/122F/141Q/154R/159D/175L;
bb) 13Y/54Q/99Y/104W/110A/113D/114F/122F/154R/159D/175L;
cc) 13Y/99Y/104W/110A/113D/114F/122F/141Q/154R/159D/175L; and
dd) 13Y/54Q/99Y/104W/110A/113D/114F/122F/141Q/154R/159D/175L, the position(s) being determined as the corresponding position of *subtilis* amino acid sequence shown as SEQ ID No. 1.

43. The polypeptide according to any one of embodiments 1-42, wherein said polypeptide has an amino acid sequence of SEQ ID No. 1, which consists of amino acid substitutions selected from the list consisting of
a) G13Y/T110A/Y113D/R122D/K154R/N159D/Q175L;
b) G13Y/K99Y/T104W/T110A/Y113D/R122F/K154R/N159D/Y166F/Q175L;
c) G13Y/K99Y/T104W/T110A/Y113D/N114F/R122F/K154R/N159D/Q175L;
d) G13Y/T110A/Y113D/R122F/Q175L;
e) G13Y/K99Y/T104W/T110A/Y113D/R122F/K154R/N159D/Q175L;
f) G13Y/K99Y/T104W/T110A/Y113D/R122F/K154R/N159D/Q175K;
g) G13Y/K99Y/T104W/T110A/Y113D/N114D/R122F/K154R/N159D/Q175K;
h) G13Y/K99Y/T104W/T110A/Y113D/N114Y/R122F/K154R/N159D/Q175L;
i) G13Y/K99Y/T104W/T110A/Y113D/N114D/R122F/K154R/N159D/Q175L;
j) G13Y/K99Y/T104W/T110A/Y113D/N114Y/R122F/K154R/N159D/Q175K;
k) G13Y/I77L/K99Y/T104W/T110A/Y113D/R122F/K154R/N159D/Q175L;
l) G13Y/V81I/K99Y/T104W/T110A/Y113D/R122F/K154R/N159D/Q175L;
m) G13Y/T110A/Y113D/R122D/W164F/Q175L;
n) G13Y/T110A/Y113D/R122D/S162D/Q175L;
o) G13Y/T110A/Y113D/R122D/Q175L;
p) D11F/R122D/T110A/Y113A;
q) G13Y/I77Y/K99Y/T104W/T110A/Y113D/R122F/K154R/N159D/Q175L;
r) D11F/R122D/T110A;
s) G13Y/G34K/T110A/Y113D/R122D/Q175L;
t) G13Y/I77V/K99Y/T104W/T110A/Y113D/R122F/K154R/N159D/Q175L;
u) G13Y/I77M/K99Y/T104W/T110A/Y113D/R122F/K154R/N159D/Q175L;
v) G13Y/K99Y/T104W/T110A/Y113D/I118V/R122F/K154R/N159D/Q175L;
w) G13Y/T110A/Y113D/R122D/S162E/Q175L; and
x) G13Y/I77S/K99Y/T104W/T110A/Y113D/R122F/K154R/N159D/Q175L
y) G13Y/K99Y/T104W/T110A/Y113D/R122F/N141Q/K154R/N159D/Q175L;
z) G13Y/N54Q/K99Y/T104W/T110A/Y113D/R122F/N141Q/K154R/N159D/Q1 75L;
aa) G13Y/N54W/K99Y/T104W/T110A/Y113D/R122F/141Q/K154R/N159D/17 5L;
bb) G13Y/N54Q/K99Y/T104W/T110A/Y113D/N114F/R122F/K154R/N159D/Q 175L;
cc) G13Y/K99Y/T10404W/T110A/Y113D/N114F/R122F/141Q/K154R/N159D/Q17 5L; and
dd) G13Y/54Q/K99Y/T104W/T110A/Y113D/N114F/R122F/141Q/K154R/N159D/Q175L.

44. The polypeptide according to any one of embodiments 1-43, which is not SEQ ID No. 25.

45. A method of identifying a polypeptide according to any one of the embodiments 1-44, said method comprising:
(i) preparing a polypeptide having at least 88% identity with SEQ ID No. 1 or having at least 75% identity with an amino acid sequence selected from SEQ ID No. 2-22, and which polypeptide has an amino acid modification in position 110, wherein said position 110 is determined as the position corresponding to position 110 of *B. subtilis* xylanase sequence shown as SEQ ID No. 1 by alignment;
(ii) comparing the bran solubilisation and/or xylanase activity of said polypeptide with the bran solubilisation and/or xylanase activity of the amino acid sequence selected among SEQ ID NOs: 1-22 with which is has the highest percentage of identity; and
(iii) selecting the polypeptide if it has improved bran solubilisation and/or improved xylanase activity compared to the amino acid sequence selected among SEQ ID NOs: 1-22 with which is has the highest percentage of identity.

46. A method of preparing a polypeptide according to any one of embodiments 1-44, said method comprising expressing a nucleotide sequence encoding said polypeptide; and optionally isolating and/or purifying the polypeptide after expression.

47. The method according to embodiment 46, wherein said polypeptide is prepared by modifying either a polypeptide amino acid sequence at position 110 or a codon that encodes an amino acid residue at position 110 in a nucleotide sequence encoding a polypeptide amino acid sequence, wherein position 110 is determined with reference to the *B. subtilis* xylanase sequence shown as SEQ ID No. 1.

48. A nucleotide sequence encoding a polypeptide according to any one of embodiments 1 to 44.

49. A vector comprising the nucleotide sequence according to embodiment 48.

50. A cell that has been transformed with the nucleotide sequence of embodiment 48 or the vector of embodiment 49.

51. A host organism that has been transformed with the nucleotide sequence of embodiment 48 or the vector of embodiment 49.

52. A composition comprising the polypeptide according to any one of embodiments 1-44 or a polypeptide identified according to any embodiment 45 or a polypeptide prepared according to embodiments 46-47 or the nucleotide sequence according to embodiment 48 or the vector according to embodiment 49 or the cell according to embodiment 50 or the organism according to embodiment 51 admixed with a non toxic component.

53. A dough comprising the polypeptide according to any one of embodiments 1-44 or a polypeptide identified according to embodiment 45 or a polypeptide prepared according to embodiments 46-47 or the nucleotide sequence according to embodiment 48 or the vector according to embodiment 49 or the cell according to embodiment 50 or the organism according to embodiment 51 admixed with a non toxic component or a composition according to embodiment 52.

54. A bakery product comprising the polypeptide according to any one of embodiments 1-44 or a polypeptide identified according to embodiment 45 or a polypeptide prepared according to embodiments 46-47 or the nucleotide sequence according to embodiment 48 or the vector according to embodiment 49 or the cell according to embodiment 50 or the organism according to embodiment 51 admixed with a non toxic component or a composition according to embodiment 52 or a dough according to embodiment 53.

55. Animal feed comprising the polypeptide according to any one of embodiments 1-44 or a polypeptide identified according to embodiment 45 or a polypeptide prepared according to embodiments 46-47 or the nucleotide sequence according to embodiment 48 or the vector according to embodiment 49 or the cell according to embodiment 50 or the organism according to embodiment 51 admixed with a non toxic component or a composition according to embodiment 52.

56. A cleaning compositions comprising the polypeptide according to any one of embodiments 1-44 or a polypeptide identified according to embodiment 45 or a polypeptide prepared according to embodiments 46-47.

57. A method of degrading or modifying a plant cell wall which method comprises contacting said plant cell wall with the polypeptide according to any one of embodiments 1-44 or a polypeptide identified according to embodiment 45 or a polypeptide prepared according to embodiments 46-47 or the nucleotide sequence according to embodiment 48 or the vector according to embodiment 49 or the cell according to embodiment 50 or the organism according to embodiment 51 admixed with a non toxic component or a composition according to embodiment 52.

58. A method of processing a plant material which method comprises contacting said plant material with the polypeptide according to any one of embodiments 1-44 or a polypeptide identified according to embodiment 45 or a polypeptide prepared according to embodiments 46-47 or the nucleotide sequence according to embodiment 47 or the vector according to embodiment 49 or the cell according to embodiment 50 or the organism according to embodiment 51 admixed with a non toxic component or a composition according to embodiment 52.

59. Use of the polypeptide according to any one of embodiments 1-44 or a polypeptide identified according to embodiment 45 or a polypeptide prepared according to embodiments 46-47 or the nucleotide sequence according to embodiment 48 or the vector according to embodiment 49 or the cell according to embodiment 50 or the organism according to embodiment 51 admixed with a non toxic component or a composition according to embodiment 52 in a method of modifying plant materials.

60. Use of the polypeptide according to any one of embodiments 1-44 or a polypeptide identified according to embodiment 45 or a polypeptide prepared according to embodiments 46-47 or the nucleotide sequence according to embodiment 48 or the vector according to embodiment 49 or the cell according to embodiment 50 or the organism according to embodiment 51 admixed with a non toxic component or a composition according to embodiment 52 in any one or more independently selected from: baking, processing cereals, starch liquefaction, production of Bio-ethanol from cellulosic material, animal feed, in processing wood, enhancing the bleaching of wood pulp, and as a cleaning composition.

61. A polypeptide or fragment thereof substantially as hereinbefore described with reference to the Examples and drawings.

62. A method substantially as hereinbefore described with reference to the Examples and drawings.

63. A composition substantially as hereinbefore described with reference to the Examples and drawings.

64. A use substantially as hereinbefore described with reference to the Examples and drawings.

References

Collins, T., Gerday, C. and Feller, G. (2005) *FEMS Microbiol Rev.*, 29 (1), 3-23.

Courtin, C., Roelants, A. and Delcour, J. (1999). Fractionation-reconstitution experiments provide insight into the role of endoxylanases in bread-making. Journal of Agricultural and Food Chemistry. 47. 1870-1877.

Coutinho, P. M. and Henrissat, B. (1999) Carbohydrate-Active Enzymes server at URL: //afmb.cnrs-mrs.fr/CAZY/.

D'Appolonia, B. L. and MacArthur, L. A. (1976). Comparison of bran and endosperm pentosans in immature and mature wheat. Cereal Chem. 53. 711-718.

Debyser, W. and Delcour, J. A. (1998). Inhibitors of cellolytic, xylanolytic and β-glucanolytic enzymes. WO 98/49278.

Hazlewood, G. P. and Gelbert, H. J. (1993). Recombinant xylanases. PCT application. WO 93/25693.

Henrissat, B. (1991) *Biochem. J.* 280, 309-316.

Ingelbrecht, J. A., Verwimp, T. and Delcour, J. A. (1999). Endoxylanases in *durum* wheat semolina processing: solubilisation of arabinoxylans, action of endogenous inhibitors and effects on rheological properties. J. *Agri.* Food Chem.

Jacobsen, T. S., Heldt-Hansen, H. P., Kofod, L. V., Bagger, C. and Mtllertz, A. (1995). Processing plant material with xylanase. PCT application. WO 95/23514.

Kormelink, F. J. M. (1992). Characterisation and mode of action of xylanases and some accessory enzymes. Ph.D. Thesis, Agricultural University Wageningen, Holland (175 pp., English and Dutch summaries).

Lever, M. (1972). A new reaction for colorimetric determination of carbohydrates. Analytical Biochemistry. 47, 273-279.

McLauchlan, R., Garcia-Conesa, M. T., Williamson, G., Roza, M., Ravestein, P. and MacGregor, A. W. (1999a). A novel class of protein from wheat which inhibits xylanases. Biochem. J. 338. 441-446.

McLauchlan, R, Flatman, R et al (1999) Poster Presentation from meeting at University of Newcastle (1999) April 11$^{th}$-April 17$^{th}$. Xylanase inhibitors, a novel class of proteins from cereals.

Montgomery, R. and Smith, F. (1955). The Carbohydrates of the Gramineae. VIII. The constitution of a water soluble hemicellulose of the endosperm of wheat (*Triticum vulgare*). J. Am. Chem. Soc. 77. 3325-3328.

Paice, M. G., Bourbonnais, R., Desrochers, M., Jurasek, L. and Yaguchi, M. (1986): A Xylanase Gene from *Bacillus subtilis*: Nucleotide Sequence and Comparison with *B. pumilus* Gene. *Arch. Microbiol*. 144, 201-206.)

Rouau, X. (1993). Investigations into the effects of an enzyme preparation for baking on wheat flour dough pentosans. J. Cereal Science. 18. 145-157.

Rouau, X., El-Hayek, M-L. and Moreau, D. (1994). Effect of an enzyme preparation containing pentosanases on the bread-making quality of flour in relation to changes in pentosan properties. J. Cereal Science. 19. 259-272.

Slade, L., Levine, H., Craig, S., Arciszewski, H. and Saunders, S. (1993). Enzyme treated low moisture content comestible products. U.S. Pat. No. 5,200,215 by Nabisco.

Soerensen, J. F. and Sibbesen, O. (1999). Bacterial xylanase. UK A 9828599.2.

The invention claimed is:

1. A recombinant polypeptide having xylanase activity and comprising an amino acid sequence, said amino acid sequence having at least 85% identity with SEQ ID No. 2 and an amino acid substitution in position 110, with any one different amino acid residue selected from the group consisting of:
asparagine (N), glutamic acid (E), tryptophan (W), alanine (A) and cysteine (C), wherein said position 110 is determined as the position within said polypeptide that corresponds to position 110 of B. subtilis xylanase sequence shown as SEQ ID No. 1 by alignment.

2. A recombinant polypeptide having xylanase activity and comprising an amino acid sequence, said amino acid sequence having at least 85% identity with SEQ ID No. 3 and an amino acid substitution in position 110, with any one different amino acid residue selected from the group consisting of:
asparagine (N), glutamic acid (E), tryptophan (W), alanine (A) and cysteine (C), wherein said position 110 is determined as the position within said polypeptide that corresponds to position 110 of B. subtilis xylanase sequence shown as SEQ ID No. 1 by alignment.

3. The recombinant polypeptide according claim 1, wherein said polypeptide has at least 90% identity with SEQ ID No. 2.

4. The recombinant polypeptide according claim 2, wherein said polypeptide has at least 90% identity with SEQ ID No. 3.

5. The recombinant polypeptide according to claim 1, having a β-jelly roll fold.

6. The recombinant polypeptide according to claim 1, wherein the amino acid substitution in position 110 is a substitution to alanine.

7. The recombinant polypeptide according to claim 1, comprising one or more modification(s) at any one or more of amino acid positions: 11, 12, 13, 34, 54, 77, 81, 99, 104, 113, 114, 118, 122, 141, 154, 159, 162, 164, 166 and 175, the position(s) being determined as the corresponding position of B. subtilis amino acid sequence shown as SEQ ID No. 1.

8. The recombinant polypeptide according claim 1, comprising one or more amino acid substitutions selected from the group consisting of: 11F, 12F, 122D, 113A, 13Y, 54Q, 54W, 113D, 141Q, 175L, 122F, 34K, 99Y, 104W, 154R, 159D, 175K, 81I, 166F, 162E, 162D, 164F, 114D, 114Y, 114F, 118V, 175K, 77L, 77M, 77S, 77V, and 77Y, the position(s) being determined as the corresponding position of B. subtilis amino acid sequence shown as SEQ ID No. 1.

9. A method of preparing a recombinant polypeptide according to claim 1, said method comprising expressing a nucleotide sequence encoding said polypeptide; and optionally isolating and/or purifying the polypeptide after expression.

10. A nucleotide sequence encoding a recombinant polypeptide according to claim 1.

11. A composition comprising a recombinant polypeptide prepared according to claim 9 admixed with a non-toxic component.

12. A composition comprising the nucleotide sequence according to claim 10 admixed with a non-toxic component.

13. The recombinant polypeptide of claim 3, wherein said polypeptide has at least 95% identity with SEQ ID No. 2.

14. The recombinant polypeptide of claim 4, wherein said polypeptide has at least 95% identity with SEQ ID No. 3.

15. The recombinant polypeptide according to claim 2, wherein the amino acid substitution in position 110 is a substitution to alanine.

16. The recombinant polypeptide according to claim 2, comprising one or more modification(s) at any one or more of amino acid positions: 11, 12, 13, 34, 54, 77, 81, 99, 104, 113, 114, 118, 122, 141, 154, 159, 162, 164, 166 and 175, the position(s) being determined as the corresponding position of B. subtilis amino acid sequence shown as SEQ ID No. 1.

17. The recombinant polypeptide according claim 2, comprising one or more amino acid substitutions selected from the group consisting of: 11F, 12F, 122D, 113A, 13Y, 54Q, 54W, 113D, 141Q, 175L, 122F, 34K, 99Y, 104W, 154R, 159D, 175K, 81I, 166F, 162E, 162D, 164F, 114D, 114Y, 114F, 118V, 175K, 77L, 77M, 77S, 77V, and 77Y, the position(s) being determined as the corresponding position of *B. subtilis* amino acid sequence shown as SEQ ID No. 1.

18. A method of preparing a recombinant polypeptide according to claim 2, said method comprising expressing a nucleotide sequence encoding said polypeptide; and optionally isolating and/or purifying the polypeptide after expression.

19. A nucleotide sequence encoding a recombinant polypeptide according to claim 2.

20. A composition comprising a recombinant polypeptide prepared according to claim 18 admixed with a non-toxic component.

21. A composition comprising the nucleotide sequence according to claim 19 admixed with a non-toxic component.

* * * * *

SEQUENCE LISTING

```
<160> NUMBER OF SEQ ID NOS: 27

<210> SEQ ID NO 1
<211> LENGTH: 185
<212> TYPE: PRT
<213> ORGANISM: Bacillus subtilis

<400> SEQUENCE: 1

Ala Ser Thr Asp Tyr Trp Gln Asn Trp Thr Asp Gly Gly Gly Ile Val
1               5                   10                  15

Asn Ala Val Asn Gly Ser Gly Gly Asn Tyr Ser Val Asn Trp Ser Asn
            20                  25                  30

Thr Gly Asn Phe Val Val Gly Lys Gly Trp Thr Thr Gly Ser Pro Phe
        35                  40                  45

Arg Thr Ile Asn Tyr Asn Ala Gly Val Trp Ala Pro Asn Gly Asn Gly
    50                  55                  60

Tyr Leu Thr Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
                85                  90                  95

Thr Val Lys Ser Asp Gly Gly Thr Tyr Asp Ile Tyr Thr Thr Thr Arg
            100                 105                 110

Tyr Asn Ala Pro Ser Ile Asp Gly Asp Arg Thr Thr Phe Thr Gln Tyr
        115                 120                 125

Trp Ser Val Arg Gln Ser Lys Arg Pro Thr Gly Ser Asn Ala Thr Ile
    130                 135                 140

Thr Phe Ser Asn His Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

<210> SEQ ID NO 2
<211> LENGTH: 191
<212> TYPE: PRT
<213> ORGANISM: Trichoderma reesei

<400> SEQUENCE: 2

Gln Cys Ile Gln Pro Gly Thr Gly Tyr Asn Asn Gly Tyr Phe Tyr Ser
1               5                   10                  15

Tyr Trp Asn Asp Gly His Gly Gly Val Thr Tyr Cys Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Arg Val Ile Asn Phe Ser Gly
    50                  55                  60

Ser Tyr Asn Pro Asn Gly Asn Ser Tyr Leu Ser Val Tyr Gly Trp Ser
```

```
                65                  70                  75                  80
Arg Asn Pro Leu Ile Glu Tyr Tyr Ile Val Glu Asn Phe Gly Thr Tyr
                    85                  90                  95

Asn Pro Ser Thr Gly Ala Thr Lys Leu Gly Glu Val Thr Ser Asp Gly
                100                 105                 110

Ser Val Tyr Asp Ile Tyr Arg Thr Gln Arg Val Asn Gln Pro Ser Ile
            115                 120                 125

Ile Gly Thr Ala Thr Phe Tyr Gln Tyr Trp Ser Val Arg Arg Asn His
        130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser Asp
                180                 185                 190

<210> SEQ ID NO 3
<211> LENGTH: 194
<212> TYPE: PRT
<213> ORGANISM: Thermomyces lanuginosus

<400> SEQUENCE: 3

Gln Thr Thr Pro Asn Ser Glu Gly Trp His Asp Gly Tyr Tyr Tyr Ser
1               5                   10                  15

Trp Trp Ser Asp Gly Gly Ala Gln Ala Thr Tyr Thr Asn Leu Glu Gly
                20                  25                  30

Gly Thr Tyr Glu Ile Ser Trp Gly Asp Gly Gly Asn Leu Val Gly Gly
            35                  40                  45

Lys Gly Trp Asn Pro Gly Leu Asn Ala Arg Ala Ile His Phe Glu Gly
        50                  55                  60

Val Tyr Gln Pro Asn Gly Asn Ser Tyr Leu Ala Val Tyr Gly Trp Thr
65                  70                  75                  80

Arg Asn Pro Leu Val Glu Tyr Tyr Ile Val Glu Asn Phe Gly Thr Tyr
                    85                  90                  95

Asp Pro Ser Ser Gly Ala Thr Asp Leu Gly Thr Val Glu Cys Asp Gly
                100                 105                 110

Ser Ile Tyr Arg Leu Gly Lys Thr Thr Arg Val Asn Ala Pro Ser Ile
            115                 120                 125

Asp Gly Thr Gln Thr Phe Asp Gln Tyr Trp Ser Val Arg Gln Asp Lys
        130                 135                 140

Arg Thr Ser Gly Thr Val Gln Thr Gly Cys His Phe Asp Ala Trp Ala
145                 150                 155                 160

Arg Ala Gly Leu Asn Val Asn Gly Asp His Tyr Tyr Gln Ile Val Ala
                165                 170                 175

Thr Glu Gly Tyr Phe Ser Ser Gly Tyr Ala Arg Ile Thr Val Ala Asp
                180                 185                 190

Val Gly

<210> SEQ ID NO 4
<211> LENGTH: 169
<212> TYPE: PRT
<213> ORGANISM: Streptomyces viridosporus

<400> SEQUENCE: 4

Trp Thr Asp Ala Gln Gly Thr Val Ser Met Asp Leu Gly Ser Gly Gly
1               5                   10                  15
```

Thr Tyr Ser Thr Gln Trp Arg Asn Thr Gly Asn Phe Val Ala Gly Lys
            20                  25                  30

Gly Trp Ser Thr Gly Gly Arg Lys Thr Val Asn Tyr Ser Gly Thr Phe
        35                  40                  45

Asn Pro Ser Gly Asn Ala Tyr Leu Thr Leu Tyr Gly Trp Thr Thr Gly
50                  55                  60

Pro Leu Ile Glu Tyr Tyr Ile Val Asp Asn Trp Gly Thr Tyr Arg Pro
65                  70                  75                  80

Thr Gly Lys Tyr Lys Gly Thr Val Thr Ser Asp Gly Gly Thr Tyr Asp
                85                  90                  95

Ile Tyr Lys Thr Thr Arg Tyr Asn Ala Pro Ser Ile Glu Gly Thr Lys
            100                 105                 110

Thr Phe Asp Gln Tyr Trp Ser Val Arg Gln Ser Lys Arg Thr Gly Gly
        115                 120                 125

Thr Ile Thr Ser Gly Asn His Phe Asp Ala Trp Ala Arg Asn Gly Met
130                 135                 140

Asn Leu Gly Asn His Asn Tyr Met Ile Met Ala Thr Glu Gly Tyr Gln
145                 150                 155                 160

Ser Ser Gly Ser Ser Thr Ile Thr Val
                165

<210> SEQ ID NO 5
<211> LENGTH: 213
<212> TYPE: PRT
<213> ORGANISM: Bacillus subtilis

<400> SEQUENCE: 5

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala Ala Ser Thr Asp
            20                  25                  30

Tyr Trp Gln Asn Trp Thr Asp Gly Gly Gly Ile Val Asn Ala Val Asn
        35                  40                  45

Gly Ser Gly Gly Asn Tyr Ser Val Asn Trp Ser Asn Thr Gly Asn Phe
50                  55                  60

Val Val Gly Lys Gly Trp Thr Thr Gly Ser Pro Phe Arg Thr Ile Asn
65                  70                  75                  80

Tyr Asn Ala Gly Val Trp Ala Pro Asn Gly Asn Gly Tyr Leu Thr Leu
                85                  90                  95

Tyr Gly Trp Thr Arg Ser Pro Leu Ile Glu Tyr Tyr Val Val Asp Ser
            100                 105                 110

Trp Gly Thr Tyr Arg Pro Thr Gly Thr Tyr Lys Gly Thr Val Lys Ser
        115                 120                 125

Asp Gly Gly Thr Tyr Asp Ile Tyr Thr Thr Thr Arg Tyr Asn Ala Pro
130                 135                 140

Ser Ile Asp Gly Asp Arg Thr Thr Phe Thr Gln Tyr Trp Ser Val Arg
145                 150                 155                 160

Gln Ser Lys Arg Pro Thr Gly Ser Asn Ala Thr Ile Thr Phe Ser Asn
                165                 170                 175

His Val Asn Ala Trp Lys Ser His Gly Met Asn Leu Gly Ser Asn Trp
            180                 185                 190

Ala Tyr Gln Val Met Ala Thr Glu Gly Tyr Gln Ser Ser Gly Ser Ser
        195                 200                 205

Asn Val Thr Val Trp

<210> SEQ ID NO 6
<211> LENGTH: 248
<212> TYPE: PRT
<213> ORGANISM: Unknown
<220> FEATURE:
<223> OTHER INFORMATION: unnamed protein product

<400> SEQUENCE: 6

Met Arg Gln Lys Lys Leu Thr Leu Ile Leu Ala Phe Leu Val Cys Phe
1               5                   10                  15

Ala Leu Thr Leu Pro Ala Glu Ile Ile Gln Ala Gln Ile Val Thr Asp
            20                  25                  30

Asn Ser Ile Gly Asn His Asp Gly Tyr Asp Tyr Glu Phe Trp Lys Asp
        35                  40                  45

Ser Gly Gly Ser Gly Thr Met Ile Leu Asn His Gly Gly Thr Phe Ser
    50                  55                  60

Ala Gln Trp Asn Asn Val Asn Asn Ile Leu Phe Arg Lys Gly Lys Lys
65                  70                  75                  80

Phe Asn Glu Thr Gln Thr His Gln Gln Val Gly Asn Met Ser Ile Asn
                85                  90                  95

Tyr Gly Ala Asn Phe Gln Pro Asn Gly Asn Ala Tyr Leu Cys Val Tyr
            100                 105                 110

Gly Trp Thr Val Asp Pro Leu Val Glu Tyr Tyr Ile Val Asp Ser Trp
        115                 120                 125

Gly Asn Trp Arg Pro Pro Gly Ala Thr Pro Lys Gly Thr Ile Thr Val
    130                 135                 140

Asp Gly Gly Thr Tyr Asp Ile Tyr Glu Thr Leu Arg Val Asn Gln Pro
145                 150                 155                 160

Ser Ile Lys Gly Ile Ala Thr Phe Lys Gln Tyr Trp Ser Val Arg Arg
                165                 170                 175

Ser Lys Arg Thr Ser Gly Thr Ile Ser Val Ser Asn His Phe Arg Ala
            180                 185                 190

Trp Glu Asn Leu Gly Met Asn Met Gly Lys Met Tyr Glu Val Ala Leu
        195                 200                 205

Thr Val Glu Gly Tyr Gln Ser Ser Gly Ser Ala Asn Val Tyr Ser Asn
    210                 215                 220

Thr Leu Arg Ile Asn Gly Asn Pro Leu Ser Thr Ile Ser Asn Asp Glu
225                 230                 235                 240

Ser Ile Thr Leu Asp Lys Asn Asn
                245

<210> SEQ ID NO 7
<211> LENGTH: 222
<212> TYPE: PRT
<213> ORGANISM: Unknown
<220> FEATURE:
<223> OTHER INFORMATION: Sequence 5 from patent US 7314743

<400> SEQUENCE: 7

Met Val Ser Phe Thr Ser Leu Leu Ala Ala Ser Pro Pro Ser Arg Ala
1               5                   10                  15

Ser Cys Arg Pro Ala Ala Glu Val Glu Ser Val Ala Val Glu Lys Arg
            20                  25                  30

Gln Thr Ile Gln Pro Gly Thr Gly Tyr Asn Asn Gly Tyr Phe Tyr Ser
        35                  40                  45

```
Tyr Trp Asn Asp Gly His Gly Gly Val Thr Tyr Thr Asn Gly Pro Gly
    50              55                  60

Gly Gln Phe Ser Val Asn Trp Ser Asn Ser Gly Asn Phe Val Gly Gly
65              70                  75                  80

Lys Gly Trp Gln Pro Gly Thr Lys Asn Lys Val Ile Asn Phe Ser Gly
                85                  90                  95

Ser Tyr Asn Pro Asn Gly Asn Ser Tyr Leu Ser Val Tyr Gly Trp Ser
            100                 105                 110

Arg Asn Pro Leu Ile Glu Tyr Tyr Ile Val Glu Asn Phe Gly Thr Tyr
                115                 120                 125

Asn Pro Ser Thr Gly Ala Thr Lys Leu Gly Val Thr Ser Asp Gly
            130                 135                 140

Ser Val Tyr Asp Ile Tyr Arg Thr Gln Arg Val Asn Gln Pro Ser Ile
145                 150                 155                 160

Ile Gly Thr Ala Thr Phe Tyr Gln Tyr Trp Ser Val Arg Arg Asn His
                    165                 170                 175

Arg Ser Ser Gly Ser Val Asn Thr Ala Asn His Phe Asn Ala Trp Ala
            180                 185                 190

Gln Gln Gly Leu Thr Leu Gly Thr Met Asp Tyr Gln Ile Val Ala Val
            195                 200                 205

Glu Gly Tyr Phe Ser Ser Gly Ser Ala Ser Ile Thr Val Ser
210                 215                 220

<210> SEQ ID NO 8
<211> LENGTH: 225
<212> TYPE: PRT
<213> ORGANISM: Unknown
<220> FEATURE:
<223> OTHER INFORMATION: Sequence 2 from patent US 5817500

<400> SEQUENCE: 8

Met Val Gly Phe Thr Pro Val Ala Leu Ala Ala Leu Ala Ala Thr Gly
1               5                   10                  15

Ala Leu Ala Phe Pro Ala Gly Asn Ala Thr Glu Leu Glu Lys Arg Gln
                20                  25                  30

Thr Thr Pro Asn Ser Glu Gly Trp His Asp Gly Tyr Tyr Tyr Ser Trp
                35                  40                  45

Trp Ser Asp Gly Gly Ala Gln Ala Thr Tyr Thr Asn Leu Glu Gly Gly
    50                  55                  60

Thr Tyr Glu Ile Ser Trp Gly Asp Gly Gly Asn Leu Val Gly Gly Lys
65              70                  75                  80

Gly Trp Asn Pro Gly Leu Asn Ala Arg Ala Ile His Phe Glu Gly Val
                85                  90                  95

Tyr Gln Pro Asn Gly Asn Ser Tyr Leu Ala Val Tyr Gly Trp Thr Arg
            100                 105                 110

Asn Pro Leu Val Glu Tyr Tyr Ile Val Glu Asn Phe Gly Thr Tyr Asp
                115                 120                 125

Pro Ser Ser Gly Ala Thr Asp Leu Gly Thr Val Glu Cys Asp Gly Ser
            130                 135                 140

Ile Tyr Arg Leu Gly Lys Thr Thr Arg Val Asn Ala Pro Ser Ile Asp
145                 150                 155                 160

Gly Thr Gln Thr Phe Asp Gln Tyr Trp Ser Val Arg Gln Asp Lys Arg
                    165                 170                 175

Thr Ser Gly Thr Val Gln Thr Gly Cys His Phe Asp Ala Trp Ala Arg
            180                 185                 190
```

Ala Gly Leu Asn Val Asn Gly Asp His Tyr Tyr Gln Ile Val Ala Thr
            195                 200                 205

Glu Gly Tyr Phe Ser Ser Gly Tyr Ala Arg Ile Thr Val Ala Asp Val
    210                 215                 220

Gly
225

<210> SEQ ID NO 9
<211> LENGTH: 210
<212> TYPE: PRT
<213> ORGANISM: Paenibacillus pabuli

<400> SEQUENCE: 9

Met Phe Lys Phe Gly Lys Lys Leu Leu Thr Val Val Leu Ala Ala Ser
1               5                   10                  15

Met Ser Phe Gly Val Phe Ala Ala Thr Thr Gly Ala Thr Asp Tyr Trp
            20                  25                  30

Gln Asn Trp Thr Asp Gly Gly Gly Thr Val Asn Ala Val Asn Gly Ser
        35                  40                  45

Gly Gly Asn Tyr Ser Val Asn Trp Gln Asn Thr Gly Asn Phe Val Val
    50                  55                  60

Gly Lys Gly Trp Thr Tyr Gly Thr Pro Asn Arg Val Val Asn Tyr Asn
65                  70                  75                  80

Ala Gly Val Phe Ser Pro Ser Gly Asn Gly Tyr Leu Thr Phe Tyr Gly
                85                  90                  95

Trp Thr Arg Asn Ala Leu Ile Glu Tyr Tyr Val Val Asp Asn Trp Gly
            100                 105                 110

Thr Tyr Arg Pro Thr Gly Thr Tyr Lys Gly Thr Val Thr Ser Asp Gly
        115                 120                 125

Gly Thr Tyr Asp Ile Tyr Thr Thr Met Arg Tyr Asn Gln Pro Ser Ile
    130                 135                 140

Asp Gly Tyr Ser Thr Phe Pro Gln Tyr Trp Ser Val Arg Gln Ser Lys
145                 150                 155                 160

Arg Pro Ile Gly Val Asn Ser Gln Ile Thr Phe Gln Asn His Val Asn
                165                 170                 175

Ala Trp Ala Ser Lys Gly Met Tyr Leu Gly Asn Ser Trp Ser Tyr Gln
            180                 185                 190

Val Met Ala Thr Glu Gly Tyr Gln Ser Ser Gly Ser Ser Asn Val Thr
        195                 200                 205

Val Trp
    210

<210> SEQ ID NO 10
<211> LENGTH: 210
<212> TYPE: PRT
<213> ORGANISM: Bacillus halodurans

<400> SEQUENCE: 10

Met Phe Lys Phe Val Thr Lys Val Leu Thr Val Val Ile Ala Ala Thr
1               5                   10                  15

Ile Ser Phe Cys Leu Ser Ala Val Pro Ala Ser Ala Asn Thr Tyr Trp
            20                  25                  30

Gln Tyr Trp Thr Asp Gly Gly Gly Thr Val Asn Ala Thr Asn Gly Pro
        35                  40                  45

Gly Gly Asn Tyr Ser Val Thr Trp Arg Asp Thr Gly Asn Phe Val Val
    50                  55                  60

```
Gly Lys Gly Trp Glu Ile Gly Ser Pro Asn Arg Thr Ile His Tyr Asn
 65                  70                  75                  80

Ala Gly Val Trp Glu Pro Ser Gly Asn Gly Tyr Leu Thr Leu Tyr Gly
                 85                  90                  95

Trp Thr Arg Asn Gln Leu Ile Glu Tyr Tyr Val Val Asp Asn Trp Gly
            100                 105                 110

Thr Tyr Arg Pro Thr Gly Thr His Arg Gly Thr Val Ser Asp Gly
            115                 120                 125

Gly Thr Tyr Asp Ile Tyr Thr Thr Met Arg Tyr Asn Ala Pro Ser Ile
            130                 135                 140

Asp Gly Thr Gln Thr Phe Gln Gln Phe Trp Ser Val Arg Gln Ser Lys
145                 150                 155                 160

Arg Pro Thr Gly Asn Asn Val Ser Ile Thr Phe Ser Asn His Val Asn
                165                 170                 175

Ala Trp Arg Asn Ala Gly Met Asn Leu Gly Ser Ser Trp Ser Tyr Gln
            180                 185                 190

Val Leu Ala Thr Glu Gly Tyr Gln Ser Ser Gly Arg Ser Asn Val Thr
            195                 200                 205

Val Trp
    210

<210> SEQ ID NO 11
<211> LENGTH: 248
<212> TYPE: PRT
<213> ORGANISM: unknown
<220> FEATURE:
<223> OTHER INFORMATION: unnamed protein product

<400> SEQUENCE: 11

Met Arg Gln Lys Lys Leu Thr Phe Ile Leu Ala Phe Leu Val Cys Phe
  1               5                  10                  15

Ala Leu Thr Leu Pro Ala Glu Ile Ile Gln Ala Gln Ile Val Thr Asp
                 20                  25                  30

Asn Ser Ile Gly Asn His Asp Gly Tyr Asp Tyr Glu Phe Trp Lys Asp
             35                  40                  45

Ser Gly Gly Ser Gly Thr Met Ile Leu Asn His Gly Thr Phe Ser
     50                  55                  60

Ala Gln Trp Asn Asn Val Asn Asn Ile Leu Phe Arg Lys Gly Lys Lys
 65                  70                  75                  80

Phe Asn Glu Thr Gln Thr His Gln Gln Val Gly Asn Met Ser Ile Asn
                 85                  90                  95

Tyr Gly Ala Asn Phe Gln Pro Asn Gly Asn Ala Tyr Leu Cys Val Tyr
            100                 105                 110

Gly Trp Thr Val Asp Pro Leu Val Glu Tyr Tyr Ile Val Asp Ser Trp
            115                 120                 125

Gly Asn Trp Arg Pro Pro Gly Ala Thr Pro Lys Gly Thr Ile Thr Val
            130                 135                 140

Asp Gly Gly Thr Tyr Asp Ile Tyr Glu Thr Leu Arg Val Asn Gln Pro
145                 150                 155                 160

Ser Ile Lys Gly Ile Ala Thr Phe Lys Gln Tyr Trp Ser Val Arg Arg
                165                 170                 175

Ser Lys Arg Thr Ser Gly Thr Ile Ser Val Ser Asn His Phe Arg Ala
            180                 185                 190

Trp Glu Asn Leu Gly Met Asn Met Gly Lys Met Tyr Glu Val Ala Leu
            195                 200                 205
```

```
Thr Val Glu Gly Tyr Gln Ser Ser Gly Ser Ala Asn Val Tyr Ser Asn
210                 215                 220

Thr Leu Arg Ile Asn Gly Asn Pro Leu Ser Thr Ile Ser Asn Asp Lys
225                 230                 235                 240

Ser Ile Thr Leu Asp Lys Asn Asn
                245

<210> SEQ ID NO 12
<211> LENGTH: 213
<212> TYPE: PRT
<213> ORGANISM: Bacillus subtilis

<400> SEQUENCE: 12

Met Phe Lys Phe Lys Lys Lys Phe Leu Val Gly Leu Thr Ala Ala Phe
1               5                   10                  15

Met Ser Ile Ser Met Phe Ser Ala Thr Ala Ser Ala Ala Gly Thr Asp
            20                  25                  30

Tyr Trp Gln Asn Trp Thr Asp Gly Gly Gly Thr Val Asn Ala Val Asn
        35                  40                  45

Gly Ser Gly Gly Asn Tyr Ser Val Asn Trp Ser Asn Thr Gly Asn Phe
    50                  55                  60

Val Val Gly Lys Gly Trp Thr Thr Gly Ser Pro Phe Arg Thr Ile Asn
65                  70                  75                  80

Tyr Asn Ala Gly Val Trp Ala Pro Asn Gly Asn Gly Tyr Leu Thr Leu
                85                  90                  95

Tyr Gly Trp Thr Arg Ser Pro Leu Ile Glu Tyr Tyr Val Val Asp Ser
            100                 105                 110

Trp Gly Thr Tyr Arg Pro Thr Gly Thr Tyr Lys Gly Thr Val Lys Ser
        115                 120                 125

Asp Gly Gly Thr Tyr Asp Ile Tyr Thr Thr Thr Arg Tyr Asn Ala Pro
    130                 135                 140

Ser Ile Asp Gly Asp Asn Thr Thr Phe Thr Gln Tyr Trp Ser Val Arg
145                 150                 155                 160

Gln Ser Lys Arg Pro Thr Gly Ser Asn Ala Ala Ile Thr Phe Ser Asn
                165                 170                 175

His Val Asn Ala Trp Lys Ser His Gly Met Asn Leu Gly Ser Asn Trp
            180                 185                 190

Ala Tyr Gln Val Leu Ala Thr Glu Gly Tyr Lys Ser Ser Gly Ser Ser
        195                 200                 205

Asn Val Thr Val Trp
    210

<210> SEQ ID NO 13
<211> LENGTH: 228
<212> TYPE: PRT
<213> ORGANISM: Unknown
<220> FEATURE:
<223> OTHER INFORMATION: Sequence 14 from patent US 6682923

<400> SEQUENCE: 13

Met Asn Leu Arg Lys Leu Arg Leu Leu Phe Val Met Cys Ile Gly Leu
1               5                   10                  15

Thr Leu Ile Leu Thr Ala Val Pro Ala His Ala Arg Thr Ile Thr Asn
            20                  25                  30

Asn Glu Met Gly Asn His Ser Gly Tyr Asp Tyr Glu Leu Trp Lys Asp
        35                  40                  45

Tyr Gly Asn Thr Ser Met Thr Leu Asn Asn Gly Gly Ala Phe Ser Ala
```

```
Gly Trp Asn Asn Ile Gly Asn Ala Leu Phe Arg Lys Gly Lys Lys Phe
 65                  70                  75                  80

Asp Ser Thr Arg Thr His His Gln Leu Gly Asn Ile Ser Ile Asn Tyr
                 85                  90                  95

Asn Ala Ser Phe Asn Pro Gly Gly Asn Ser Tyr Leu Cys Val Tyr Gly
            100                 105                 110

Trp Thr Gln Ser Pro Leu Ala Glu Tyr Tyr Ile Val Asp Ser Trp Gly
        115                 120                 125

Thr Tyr Arg Pro Thr Gly Ala Tyr Lys Gly Ser Phe Tyr Ala Asp Gly
    130                 135                 140

Gly Thr Tyr Asp Ile Tyr Glu Thr Thr Arg Val Asn Gln Pro Ser Ile
145                 150                 155                 160

Ile Gly Ile Ala Thr Phe Lys Gln Tyr Trp Ser Val Arg Gln Thr Lys
                165                 170                 175

Arg Thr Ser Gly Thr Val Ser Val Ser Ala His Phe Arg Lys Trp Glu
            180                 185                 190

Ser Leu Gly Met Pro Met Gly Lys Met Tyr Glu Thr Ala Phe Thr Val
        195                 200                 205

Glu Gly Tyr Gln Ser Ser Gly Ser Ala Asn Val Met Thr Asn Gln Leu
    210                 215                 220

Phe Ile Gly Asn
225

<210> SEQ ID NO 14
<211> LENGTH: 223
<212> TYPE: PRT
<213> ORGANISM: Penicillium funiculosum

<400> SEQUENCE: 14

Met Lys Leu Phe Leu Ala Ala Ile Val Leu Cys Ala Thr Ala Ala Thr
 1               5                  10                  15

Ala Phe Pro Ser Glu Leu Ala Gln Arg Ala Ala Gly Asp Leu Ser Lys
                20                  25                  30

Arg Gln Ser Ile Thr Thr Ser Gln Thr Gly Thr Asn Asn Gly Tyr Tyr
            35                  40                  45

Tyr Ser Phe Trp Thr Asn Gly Gly Gly Glu Val Thr Tyr Thr Asn Gly
        50                  55                  60

Asp Asn Gly Glu Tyr Ser Val Thr Trp Val Asp Cys Gly Asp Phe Thr
 65                  70                  75                  80

Ser Gly Lys Gly Trp Asn Pro Ala Asn Ala Gln Thr Val Thr Tyr Ser
                 85                  90                  95

Gly Glu Phe Asn Pro Ser Gly Asn Ala Tyr Leu Ala Val Tyr Gly Trp
            100                 105                 110

Thr Thr Asp Pro Leu Val Glu Tyr Tyr Ile Leu Glu Ser Tyr Gly Thr
        115                 120                 125

Tyr Asn Pro Ser Ser Gly Leu Thr Ser Leu Gly Gln Val Thr Ser Asp
    130                 135                 140

Gly Gly Thr Tyr Asp Ile Tyr Ser Thr Gln Arg Val Asn Gln Pro Ser
145                 150                 155                 160

Ile Glu Gly Thr Ser Thr Phe Asn Gln Tyr Trp Ser Val Arg Thr Glu
                165                 170                 175

Lys Arg Val Gly Gly Thr Val Thr Thr Ala Asn His Phe Ala Ala Trp
            180                 185                 190
```

```
Lys Ala Leu Gly Leu Glu Met Gly Thr Tyr Asn Tyr Met Ile Val Ser
            195                 200                 205

Thr Glu Gly Tyr Glu Ser Ser Gly Ser Ser Thr Ile Thr Val Ser
    210                 215                 220

<210> SEQ ID NO 15
<211> LENGTH: 221
<212> TYPE: PRT
<213> ORGANISM: unknown
<220> FEATURE:
<223> OTHER INFORMATION: unnamed protein product

<400> SEQUENCE: 15

Gln Ile Val Thr Asp Asn Ser Ile Gly Asn His Asp Gly Tyr Asp Tyr
1               5                   10                  15

Glu Phe Trp Lys Asp Ser Gly Gly Ser Gly Thr Met Ile Leu Asn His
            20                  25                  30

Gly Gly Thr Phe Ser Ala Gln Trp Asn Asn Val Asn Asn Ile Leu Phe
        35                  40                  45

Arg Lys Gly Lys Lys Phe Asn Glu Thr Gln Thr His Gln Gln Val Gly
    50                  55                  60

Asn Met Ser Ile Asn Tyr Gly Ala Asn Phe Gln Pro Asn Gly Asn Ala
65                  70                  75                  80

Tyr Leu Cys Val Tyr Gly Trp Thr Val Asp Pro Leu Val Glu Tyr Tyr
                85                  90                  95

Ile Val Asp Ser Trp Gly Asn Trp Arg Pro Pro Gly Ala Thr Pro Lys
            100                 105                 110

Gly Thr Ile Thr Val Asp Gly Gly Thr Tyr Asp Ile Tyr Glu Thr Leu
        115                 120                 125

Arg Val Asn Gln Pro Ser Ile Lys Gly Ile Ala Thr Phe Lys Gln Tyr
    130                 135                 140

Trp Ser Val Arg Arg Ser Lys Arg Thr Ser Gly Thr Ile Ser Val Ser
145                 150                 155                 160

Asn His Phe Arg Ala Trp Glu Asn Leu Gly Met Asn Met Gly Lys Met
                165                 170                 175

Tyr Glu Val Ala Leu Thr Val Glu Gly Tyr Gln Ser Ser Gly Ser Ala
            180                 185                 190

Asn Val Tyr Ser Asn Thr Leu Arg Ile Asn Gly Asn Pro Leu Ser Thr
        195                 200                 205

Ile Ser Asn Asp Glu Ser Ile Thr Leu Asp Lys Asn Asn
    210                 215                 220

<210> SEQ ID NO 16
<211> LENGTH: 190
<212> TYPE: PRT
<213> ORGANISM: unknown
<220> FEATURE:
<223> OTHER INFORMATION: Sequence 5 from patent US7314743

<400> SEQUENCE: 16

Gln Thr Ile Gln Pro Gly Thr Gly Tyr Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60
```

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
            115                 120                 125

Ile Gly Thr Ala Thr Phe Tyr Gln Tyr Trp Ser Val Arg Arg Asn His
            130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 17
<211> LENGTH: 182
<212> TYPE: PRT
<213> ORGANISM: Paenibacillus pabuli

<400> SEQUENCE: 17

Thr Asp Tyr Trp Gln Asn Trp Thr Asp Gly Gly Gly Thr Val Asn Ala
1               5                   10                  15

Val Asn Gly Ser Gly Gly Asn Tyr Ser Val Asn Trp Gln Asn Thr Gly
                20                  25                  30

Asn Phe Val Val Gly Lys Gly Trp Thr Tyr Gly Thr Pro Asn Arg Val
            35                  40                  45

Val Asn Tyr Asn Ala Gly Val Phe Ser Pro Ser Gly Asn Gly Tyr Leu
        50                  55                  60

Thr Phe Tyr Gly Trp Thr Arg Asn Ala Leu Ile Glu Tyr Tyr Val Val
65                  70                  75                  80

Asp Asn Trp Gly Thr Tyr Arg Pro Thr Gly Thr Tyr Lys Gly Thr Val
                85                  90                  95

Thr Ser Asp Gly Gly Thr Tyr Asp Ile Tyr Thr Thr Met Arg Tyr Asn
            100                 105                 110

Gln Pro Ser Ile Asp Gly Tyr Ser Thr Phe Pro Gln Tyr Trp Ser Val
            115                 120                 125

Arg Gln Ser Lys Arg Pro Ile Gly Val Asn Ser Gln Ile Thr Phe Gln
            130                 135                 140

Asn His Val Asn Ala Trp Ala Ser Lys Gly Met Tyr Leu Gly Asn Ser
145                 150                 155                 160

Trp Ser Tyr Gln Val Met Ala Thr Glu Gly Tyr Gln Ser Ser Gly Ser
                165                 170                 175

Ser Asn Val Thr Val Trp
            180

<210> SEQ ID NO 18
<211> LENGTH: 182
<212> TYPE: PRT
<213> ORGANISM: Bacillus halodurans

<400> SEQUENCE: 18

Asn Thr Tyr Trp Gln Tyr Trp Thr Asp Gly Gly Gly Thr Val Asn Ala
1               5                   10                  15

Thr Asn Gly Pro Gly Gly Asn Tyr Ser Val Thr Trp Arg Asp Thr Gly
            20                  25                  30

Asn Phe Val Val Gly Lys Gly Trp Glu Ile Gly Ser Pro Asn Arg Thr
        35                  40                  45

Ile His Tyr Asn Ala Gly Val Trp Glu Pro Ser Gly Asn Gly Tyr Leu
    50                  55                  60

Thr Leu Tyr Gly Trp Thr Arg Asn Gln Leu Ile Glu Tyr Tyr Val Val
65                  70                  75                  80

Asp Asn Trp Gly Thr Tyr Arg Pro Thr Gly Thr His Arg Gly Thr Val
                85                  90                  95

Val Ser Asp Gly Gly Thr Tyr Asp Ile Tyr Thr Thr Met Arg Tyr Asn
            100                 105                 110

Ala Pro Ser Ile Asp Gly Thr Gln Thr Phe Gln Gln Phe Trp Ser Val
        115                 120                 125

Arg Gln Ser Lys Arg Pro Thr Gly Asn Asn Val Ser Ile Thr Phe Ser
130                 135                 140

Asn His Val Asn Ala Trp Arg Asn Ala Gly Met Asn Leu Gly Ser Ser
145                 150                 155                 160

Trp Ser Tyr Gln Val Leu Ala Thr Glu Gly Tyr Gln Ser Ser Gly Arg
                165                 170                 175

Ser Asn Val Thr Val Trp
            180

<210> SEQ ID NO 19
<211> LENGTH: 221
<212> TYPE: PRT
<213> ORGANISM: unknown
<220> FEATURE:
<223> OTHER INFORMATION: unnamed protein product

<400> SEQUENCE: 19

Gln Ile Val Thr Asp Asn Ser Ile Gly Asn His Asp Gly Tyr Asp Tyr
1               5                   10                  15

Glu Phe Trp Lys Asp Ser Gly Gly Ser Gly Thr Met Ile Leu Asn His
            20                  25                  30

Gly Gly Thr Phe Ser Ala Gln Trp Asn Asn Val Asn Asn Ile Leu Phe
        35                  40                  45

Arg Lys Gly Lys Lys Phe Asn Glu Thr Gln Thr His Gln Gln Val Gly
    50                  55                  60

Asn Met Ser Ile Asn Tyr Gly Ala Asn Phe Gln Pro Asn Gly Asn Ala
65                  70                  75                  80

Tyr Leu Cys Val Tyr Gly Trp Thr Val Asp Pro Leu Val Glu Tyr Tyr
                85                  90                  95

Ile Val Asp Ser Trp Gly Asn Trp Arg Pro Pro Gly Ala Thr Pro Lys
            100                 105                 110

Gly Thr Ile Thr Val Asp Gly Gly Thr Tyr Asp Ile Tyr Glu Thr Leu
        115                 120                 125

Arg Val Asn Gln Pro Ser Ile Lys Gly Ile Ala Thr Phe Lys Gln Tyr
130                 135                 140

Trp Ser Val Arg Arg Ser Lys Arg Thr Ser Gly Thr Ile Ser Val Ser
145                 150                 155                 160

Asn His Phe Arg Ala Trp Glu Asn Leu Gly Met Asn Met Gly Lys Met
                165                 170                 175

Tyr Glu Val Ala Leu Thr Val Glu Gly Tyr Gln Ser Ser Gly Ser Ala
            180                 185                 190

```
Asn Val Tyr Ser Asn Thr Leu Arg Ile Asn Gly Asn Pro Leu Ser Thr
            195                 200                 205

Ile Ser Asn Asp Lys Ser Ile Thr Leu Asp Lys Asn Asn
    210                 215                 220

<210> SEQ ID NO 20
<211> LENGTH: 185
<212> TYPE: PRT
<213> ORGANISM: Bacillus subtilis

<400> SEQUENCE: 20

Ala Gly Thr Asp Tyr Trp Gln Asn Trp Thr Asp Gly Gly Gly Thr Val
1               5                   10                  15

Asn Ala Val Asn Gly Ser Gly Gly Asn Tyr Ser Val Asn Trp Ser Asn
            20                  25                  30

Thr Gly Asn Phe Val Val Gly Lys Gly Trp Thr Thr Gly Ser Pro Phe
        35                  40                  45

Arg Thr Ile Asn Tyr Asn Ala Gly Val Trp Ala Pro Asn Gly Asn Gly
    50                  55                  60

Tyr Leu Thr Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
                85                  90                  95

Thr Val Lys Ser Asp Gly Gly Thr Tyr Asp Ile Tyr Thr Thr Thr Arg
            100                 105                 110

Tyr Asn Ala Pro Ser Ile Asp Gly Asp Asn Thr Thr Phe Thr Gln Tyr
        115                 120                 125

Trp Ser Val Arg Gln Ser Lys Arg Pro Thr Gly Ser Asn Ala Ala Ile
    130                 135                 140

Thr Phe Ser Asn His Val Asn Ala Trp Lys Ser His Gly Met Asn Leu
145                 150                 155                 160

Gly Ser Asn Trp Ala Tyr Gln Val Leu Ala Thr Glu Gly Tyr Lys Ser
                165                 170                 175

Ser Gly Ser Ser Asn Val Thr Val Trp
            180                 185

<210> SEQ ID NO 21
<211> LENGTH: 201
<212> TYPE: PRT
<213> ORGANISM: unknown
<220> FEATURE:
<223> OTHER INFORMATION: Sequence 14 from patent US6682923

<400> SEQUENCE: 21

Arg Thr Ile Thr Asn Asn Glu Met Gly Asn His Ser Gly Tyr Asp Tyr
1               5                   10                  15

Glu Leu Trp Lys Asp Tyr Gly Asn Thr Ser Met Thr Leu Asn Asn Gly
            20                  25                  30

Gly Ala Phe Ser Ala Gly Trp Asn Asn Ile Gly Asn Ala Leu Phe Arg
        35                  40                  45

Lys Gly Lys Lys Phe Asp Ser Thr Arg Thr His His Gln Leu Gly Asn
    50                  55                  60

Ile Ser Ile Asn Tyr Asn Ala Ser Phe Asn Pro Gly Gly Asn Ser Tyr
65                  70                  75                  80

Leu Cys Val Tyr Gly Trp Thr Gln Ser Pro Leu Ala Glu Tyr Tyr Ile
                85                  90                  95
```

```
Val Asp Ser Trp Gly Thr Tyr Arg Pro Thr Gly Ala Tyr Lys Gly Ser
            100                 105                 110

Phe Tyr Ala Asp Gly Gly Thr Tyr Asp Ile Tyr Glu Thr Thr Arg Val
        115                 120                 125

Asn Gln Pro Ser Ile Ile Gly Ile Ala Thr Phe Lys Gln Tyr Trp Ser
    130                 135                 140

Val Arg Gln Thr Lys Arg Thr Ser Gly Thr Val Ser Val Ser Ala His
145                 150                 155                 160

Phe Arg Lys Trp Glu Ser Leu Gly Met Pro Met Gly Lys Met Tyr Glu
                165                 170                 175

Thr Ala Phe Thr Val Glu Gly Tyr Gln Ser Ser Gly Ser Ala Asn Val
            180                 185                 190

Met Thr Asn Gln Leu Phe Ile Gly Asn
        195                 200

<210> SEQ ID NO 22
<211> LENGTH: 207
<212> TYPE: PRT
<213> ORGANISM: Penicillium funiculosum

<400> SEQUENCE: 22

Ala Phe Pro Ser Glu Leu Ala Gln Arg Ala Ala Gly Asp Leu Ser Lys
1               5                   10                  15

Arg Gln Ser Ile Thr Thr Ser Gln Thr Gly Thr Asn Asn Gly Tyr Tyr
            20                  25                  30

Tyr Ser Phe Trp Thr Asn Gly Gly Glu Val Thr Tyr Thr Asn Gly
        35                  40                  45

Asp Asn Gly Glu Tyr Ser Val Thr Trp Val Asp Cys Gly Asp Phe Thr
    50                  55                  60

Ser Gly Lys Gly Trp Asn Pro Ala Asn Ala Gln Thr Val Thr Tyr Ser
65                  70                  75                  80

Gly Glu Phe Asn Pro Ser Gly Asn Ala Tyr Leu Ala Val Tyr Gly Trp
                85                  90                  95

Thr Thr Asp Pro Leu Val Glu Tyr Tyr Ile Leu Glu Ser Tyr Gly Thr
            100                 105                 110

Tyr Asn Pro Ser Ser Gly Leu Thr Ser Leu Gly Gln Val Thr Ser Asp
        115                 120                 125

Gly Gly Thr Tyr Asp Ile Tyr Ser Thr Gln Arg Val Asn Gln Pro Ser
    130                 135                 140

Ile Glu Gly Thr Ser Thr Phe Asn Gln Tyr Trp Ser Val Arg Thr Glu
145                 150                 155                 160

Lys Arg Val Gly Gly Thr Val Thr Thr Ala Asn His Phe Ala Ala Trp
                165                 170                 175

Lys Ala Leu Gly Leu Glu Met Gly Thr Tyr Asn Tyr Met Ile Val Ser
            180                 185                 190

Thr Glu Gly Tyr Glu Ser Ser Gly Ser Ser Thr Ile Thr Val Ser
        195                 200                 205

<210> SEQ ID NO 23
<211> LENGTH: 185
<212> TYPE: PRT
<213> ORGANISM: Bacillus subtilis

<400> SEQUENCE: 23

Ala Ser Thr Asp Tyr Trp Gln Asn Trp Thr Phe Gly Gly Gly Ile Val
1               5                   10                  15
```

-continued

Asn Ala Val Asn Gly Ser Gly Gly Asn Tyr Ser Val Asn Trp Ser Asn
            20                  25                  30

Thr Gly Asn Phe Val Val Gly Lys Gly Trp Thr Thr Gly Ser Pro Phe
        35                  40                  45

Arg Thr Ile Asn Tyr Asn Ala Gly Val Trp Ala Pro Asn Gly Asn Gly
    50                  55                  60

Tyr Leu Thr Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
                85                  90                  95

Thr Val Lys Ser Asp Gly Gly Thr Tyr Asp Ile Tyr Thr Thr Thr Arg
            100                 105                 110

Tyr Asn Ala Pro Ser Ile Asp Gly Asp Thr Thr Phe Thr Gln Tyr
        115                 120                 125

Trp Ser Val Arg Gln Ser Lys Arg Pro Thr Gly Ser Asn Ala Thr Ile
    130                 135                 140

Thr Phe Ser Asn His Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

<210> SEQ ID NO 24
<211> LENGTH: 402
<212> TYPE: PRT
<213> ORGANISM: Triticum

<400> SEQUENCE: 24

Met Pro Pro Val Leu Leu Leu Val Leu Ala Ala Ser Leu Val Ala Leu
1               5                   10                  15

Pro Ser Cys Gln Ser Leu Pro Val Leu Ala Pro Val Thr Lys Asp Pro
            20                  25                  30

Ala Thr Ser Leu Tyr Thr Ile Pro Phe His Asp Gly Ala Ser Leu Val
        35                  40                  45

Leu Asp Val Ala Gly Pro Leu Val Trp Ser Thr Cys Asp Gly Gly Gln
    50                  55                  60

Pro Pro Ala Glu Ile Pro Cys Ser Ser Pro Thr Cys Leu Leu Ala Asn
65                  70                  75                  80

Ala Tyr Pro Ala Pro Gly Cys Pro Ala Pro Ser Cys Gly Ser Asp Lys
                85                  90                  95

His Asp Lys Pro Cys Thr Ala Tyr Pro Tyr Asn Pro Val Ser Gly Ala
            100                 105                 110

Cys Ala Ala Gly Ser Leu Ser His Thr Arg Phe Val Ala Asn Thr Thr
        115                 120                 125

Asp Gly Ser Lys Pro Val Ser Lys Val Asn Val Gly Val Leu Ala Ala
    130                 135                 140

Cys Ala Pro Ser Lys Leu Leu Ala Ser Leu Pro Arg Gly Ser Thr Gly
145                 150                 155                 160

Val Ala Gly Leu Ala Asn Ser Gly Leu Ala Leu Pro Ala Gln Val Ala
                165                 170                 175

Ser Ala Gln Lys Val Ala Asn Arg Phe Leu Leu Cys Leu Pro Thr Gly
            180                 185                 190

Gly Pro Gly Val Ala Ile Phe Gly Gly Gly Pro Val Pro Trp Pro Gln
        195                 200                 205

```
Phe Thr Gln Ser Met Pro Tyr Thr Pro Leu Val Thr Lys Gly Gly Ser
        210                 215                 220
Pro Ala His Tyr Ile Ser Ala Arg Ser Ile Val Val Gly Asp Thr Arg
225                 230                 235                 240
Val Pro Val Pro Glu Gly Ala Leu Ala Thr Gly Gly Val Met Leu Ser
                245                 250                 255
Thr Arg Leu Pro Tyr Val Leu Leu Arg Pro Asp Val Tyr Arg Pro Leu
            260                 265                 270
Met Asp Ala Phe Thr Lys Ala Leu Ala Ala Gln His Ala Asn Gly Ala
        275                 280                 285
Pro Val Ala Arg Ala Val Glu Ala Val Ala Pro Phe Gly Val Cys Tyr
    290                 295                 300
Asp Thr Lys Thr Leu Gly Asn Asn Leu Gly Gly Tyr Ala Val Pro Asn
305                 310                 315                 320
Val Gln Leu Gly Leu Asp Gly Gly Ser Asp Trp Thr Met Thr Gly Lys
                325                 330                 335
Asn Ser Met Val Asp Val Lys Gln Gly Thr Ala Cys Val Ala Phe Val
            340                 345                 350
Glu Met Lys Gly Val Ala Ala Gly Asp Gly Arg Ala Pro Ala Val Ile
        355                 360                 365
Leu Gly Gly Ala Gln Met Glu Asp Phe Val Leu Asp Phe Asp Met Glu
    370                 375                 380
Lys Lys Arg Leu Gly Phe Ser Arg Leu Pro His Phe Thr Gly Cys Gly
385                 390                 395                 400
Gly Leu

<210> SEQ ID NO 25
<211> LENGTH: 185
<212> TYPE: PRT
<213> ORGANISM: unknown
<220> FEATURE:
<223> OTHER INFORMATION: sequence 11 of US 6,682,923

<400> SEQUENCE: 25

Ala Ser Thr Asp Trp Trp Glu Asn Trp Thr Ile Gly Gly Gly Ile Val
1               5                   10                  15
Asn Ala Val Asn Gly Ser Gly Gly Asn Tyr Ser Val Asn Trp Ser Asn
            20                  25                  30
Thr Gly Asn Phe Asp Val Ala Lys Gly Trp Thr Thr Gly Ser Pro Phe
        35                  40                  45
Arg Thr Ile Asn Tyr Asn Ala Gly Val Trp Ala Pro Asn Gly Trp Gly
    50                  55                  60
Glu Leu Glu Leu Tyr Gly Trp Thr Arg Ser Pro Leu Ile Glu Tyr Leu
65                  70                  75                  80
Val Val Asp Ser Trp Gly Thr Asn Arg Pro Thr Gly Thr Tyr Lys Gly
                85                  90                  95
Thr Val Lys Ser Asp Gly Gly Thr Tyr Asp Ile Tyr Thr Asp Thr Arg
            100                 105                 110
Tyr Asn Tyr Pro Ser Glu Asp Gly Asp Arg Thr Thr Met Thr Gln Tyr
        115                 120                 125
Ser Ser Val Arg Gln Ser Lys Arg Pro Thr Gly Ser Asn Ala Thr Ile
    130                 135                 140
Thr Phe Thr Asn His Val Asn Ala Trp Lys Ser His Gly Met Asn Leu
145                 150                 155                 160
```

-continued

```
Gly Ser Asn Trp Ala Tyr Gln Asp Met Ala Thr Glu Gly Tyr Gln Ser
                165                 170                 175

Ser Gly Ser Ser Asn Val Thr Val Trp
            180                 185

<210> SEQ ID NO 26
<211> LENGTH: 41
<212> TYPE: DNA
<213> ORGANISM: Artificial Sequence
<220> FEATURE:
<223> OTHER INFORMATION: construct comprising the ribosome binding site
      from pET24a

<400> SEQUENCE: 26
ctagaaataa ttttgtttaa ctttaagaag gagatataca t                          41

<210> SEQ ID NO 27
<211> LENGTH: 24
<212> TYPE: DNA
<213> ORGANISM: Artificial Sequence
<220> FEATURE:
<223> OTHER INFORMATION: N-term of wild type xylanase gene without
      signal sequence

<400> SEQUENCE: 27
atggctagca cagactactg gcaa                                             24
```